United States Patent
Valdez et al.

(10) Patent No.: US 10,745,492 B1
(45) Date of Patent: Aug. 18, 2020

(54) ANTIBODIES TO SYMMETRICALLY DIMETHYLATED ARGININE ANALYTES AND USE THEREOF

(71) Applicant: ARK Diagnostics, Inc., Fremont, CA (US)

(72) Inventors: Johnny Valdez, Fremont, CA (US); Byung Sook Moon, Palo Alto, CA (US); Ki Chung, Fremont, CA (US); Yunfei Chen, Fremont, CA (US)

(73) Assignee: ARK Diagnostics, Inc., Fremont, CA (US)

( * ) Notice: Subject to any disclaimer, the term of this patent is extended or adjusted under 35 U.S.C. 154(b) by 0 days.

(21) Appl. No.: 16/414,553

(22) Filed: May 16, 2019

Related U.S. Application Data

(60) Provisional application No. 62/828,769, filed on Apr. 3, 2019.

(51) Int. Cl.
| | |
|---|---|
| *C07K 16/44* | (2006.01) |
| *C07C 279/14* | (2006.01) |
| *G01N 33/563* | (2006.01) |
| *G01N 33/535* | (2006.01) |
| *A61K 9/19* | (2006.01) |

(52) U.S. Cl.
CPC ............... *C07K 16/44* (2013.01); *A61K 9/19* (2013.01); *C07C 279/14* (2013.01); *G01N 33/535* (2013.01); *G01N 33/563* (2013.01); *C07K 2317/14* (2013.01); *C07K 2317/20* (2013.01); *C07K 2317/34* (2013.01); *C07K 2317/565* (2013.01); *C12Y 101/01049* (2013.01)

(58) Field of Classification Search
CPC .................................................. C07C 279/14
See application file for complete search history.

(56) References Cited

U.S. PATENT DOCUMENTS

| | | |
|---|---|---|
| 3,817,837 A | 6/1974 | Rubenstein |
| 4,391,904 A | 7/1983 | Litman et al. |
| 4,435,504 A | 3/1984 | Zuk et al. |
| 4,492,762 A | 1/1985 | Wang et al. |
| 4,593,089 A | 6/1986 | Wang et al. |
| 4,668,640 A | 5/1987 | Wang et al. |
| 4,751,190 A | 6/1988 | Chiapetta et al. |
| 4,847,209 A | 7/1989 | Lewis et al. |
| 4,959,324 A | 9/1990 | Ramel et al. |
| 5,061,381 A | 10/1991 | Burd |
| 5,122,284 A | 6/1992 | Braynin et al. |
| 5,173,193 A | 12/1992 | Schembri |
| 5,186,844 A | 2/1993 | Burd et al. |
| 5,264,180 A | 11/1993 | Allen et al. |
| 5,340,539 A | 8/1994 | Allen et al. |
| 5,413,732 A | 5/1995 | Buhl et al. |
| 5,416,000 A | 5/1995 | Allen et al. |
| 5,571,728 A | 11/1996 | Kraus |
| 5,985,281 A | 11/1999 | Taylorson et al. |
| 6,033,890 A | 3/2000 | Jakobovits et al. |
| 6,090,567 A | 7/2000 | Jakobovits et al. |
| 6,248,597 B1 | 6/2001 | Eda et al. |
| 6,455,288 B1 | 9/2002 | Jakobovits et al. |
| 6,514,770 B1 | 2/2003 | Sorin |
| 7,998,411 B2 | 8/2011 | Kopf-Sill et al. |
| 2016/0245801 A1 | 8/2016 | Yerramilli et al. |

OTHER PUBLICATIONS

Garske et al. Biochemistry 2006, 45, 94-101 (Year: 2006).*
Martens-Lobenhoffer et al. Journal of Chromatography B 2015, 975, 59-64 (Year: 2015).*
Cuatrecasa (1970) "Protein Purification by Affinity Chromatography Derivatizations of Agarose and Polyacrylamide Beads," J. Biol. Chem. 245(12): 3059-3065.
Lefranc et al., (2005) "IMGT, the international ImMunoGeneTics information system," Nucleic Acids Research 33: D593-D597.
Ullman et al (1996) "Luminescent oxygen channeling assay (LOCI): sensitive, broadly applicable homogeneous immunoassay method," Clinical Chemistry 42(9) 1518-1526.
May et al. (2003) "Antibodies to Keyhole Limpet Hemocyanin Cross-React with an Epitope on the Polysaccharide Capsule of Cryptococcus neoformans and Oth Carbohydrates: Implications for Vaccine Development." The Journal of Immunology 171(9): 4905-4912.
Pubchem. 5-[(N,N'-Dimethylcarbamimidoyl)amlno]-2-(methylamino)pentanoic acid. Aug. 20, 2012, pp. 1-9 [online], [retrieved on Dec. 13, 2019]. Retrieved from the Internet <URL: https:J/pubchem.ncbl.nlm.nih.gov/compound/60104172#sectIon=2D-Structure>; p. 2.

* cited by examiner

Primary Examiner — Matthew P Coughlin
(74) Attorney, Agent, or Firm — Rudy J. Ng; Brian E. Davy; Bozicevic, Field & Francis LLP

(57) ABSTRACT

Disclosed is an antibody which binds to a symmetrically dimethylated arginine analyte that can be used to detect a symmetrically dimethylated arginine analyte in a sample, such as in a homogeneous enzyme immunoassay method.

5 Claims, 13 Drawing Sheets

Specification includes a Sequence Listing.

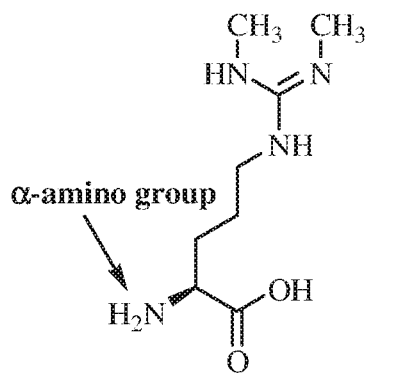
Symmetric dimethylarginine
(SDMA)
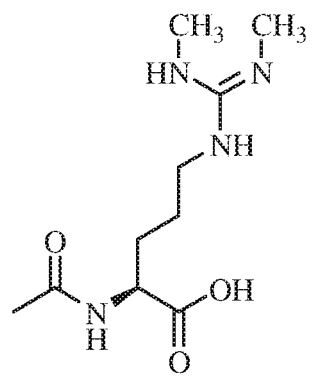
Symmetric Nα–acetyl–dimethylarginine
(Ac–SDMA metabolite)
**FIG. 1
(RELATED ART)**
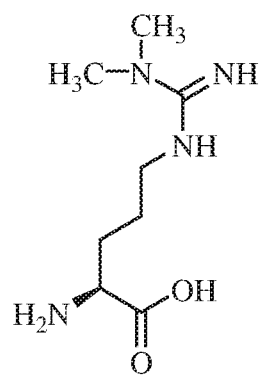
Asymmetric dimethylarginine
(ADMA)
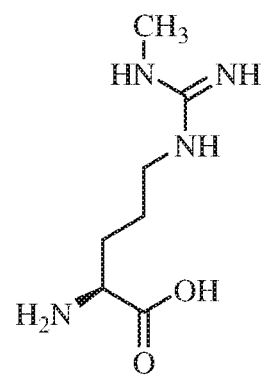
Monomethylarginine
(MMA)
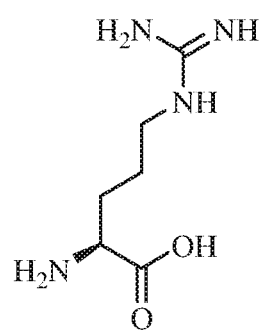
Arginine (ARG)
**FIG. 2
(RELATED ART)**

SDMA–Gly–Gly Dipeptide

SDMA–M
(Nα–alkyl–SDMA)

SDMA–SBAP
(Nα–acyl–SDMA)

A. Inhibition

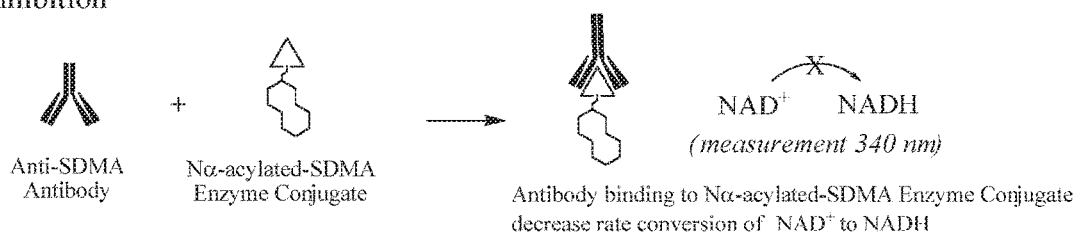

Anti-SDMA Antibody  Nα-acylated-SDMA Enzyme Conjugate

Antibody binding to Nα-acylated-SDMA Enzyme Conjugate decrease rate conversion of NAD⁺ to NADH B. Modulation

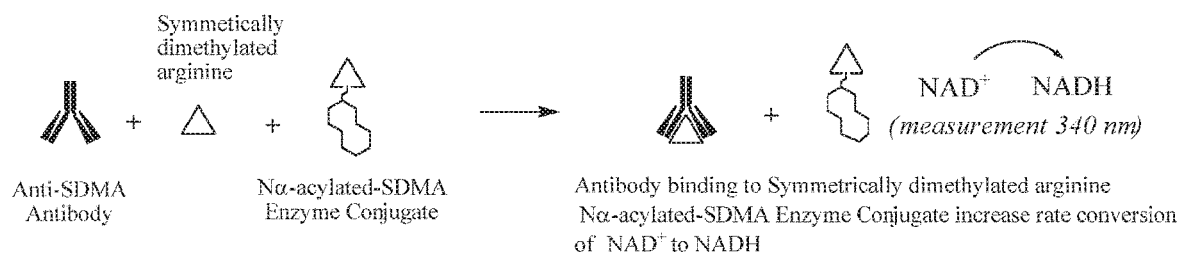

Anti-SDMA Antibody  Nα-acylated-SDMA Enzyme Conjugate

Antibody binding to Symmetrically dimethylated arginine Nα-acylated-SDMA Enzyme Conjugate increase rate conversion of NAD⁺ to NADH

FIG. 10

ANTIBODIES TO SYMMETRICALLY DIMETHYLATED ARGININE ANALYTES AND USE THEREOF

CROSS-REFERENCE TO RELATED APPLICATIONS

This application claims priority pursuant to 35 U.S.C. § 119(e) to the filing date of U.S. Provisional Application Ser. No. 62/828,769 filed on Apr. 3, 2019, the disclosure of which is herein incorporated by reference.

FIELD OF THE INVENTION

The present invention relates to the field of immunoassays, and in particular to antibodies which bind to a symmetrically dimethylated arginine analyte that can be used in immunoassays for detection of a symmetrically dimethylated arginine analyte.

INTRODUCTION

Chronic kidney disease (CKD) is a common problem in dogs and cats. There is no cure available for CKD, but medical management is available for patients with this disease. Research has focused on earlier detection of CKD with the goal of instituting medical management and monitoring as early in the disease course as possible. Symmetric dimethylarginine has recently emerged as a novel renal excretory biomarker that may aid in early detection of CKD in cats and dogs.

Symmetric dimethylarginine (SDMA; FIG. 1), in addition to asymmetric dimethylarginine (ADMA; FIG. 2) and monomethylarginine (MMA, or N-methylarginine; FIG. 2) are derived from posttranslational modification (methylation) of proteins containing arginine residues within almost every cell. After proteolysis, or protein breakdown, these protein residues are released into the circulation. The potential use of serum symmetric dimethylarginine as a marker for evaluation of kidney disease, cardiovascular health, atherosclerosis, rheumatoid arthritis, and other diseases, has been extensively studied.

Symmetric dimethylarginine is eliminated from the body primarily via renal excretion. Unlike creatinine, symmetric dimethylarginine is unaffected by non-renal factors including lean body mass. Symmetric dimethylarginine does not bind to protein, unlike asymmetric dimethylarginine, which is partially bound to plasma proteins. Correlations between asymmetric dimethylarginine and glomerular filtration rate (GFR) have been shown to be much weaker, likely due to the protein-bound fraction of asymmetric dimethylarginine, which hinders glomerular filtration.

Serum concentrations of symmetric dimethylarginine are also increased in human patients with CKD. It has been shown that serum symmetric dimethylarginine concentrations are inversely correlated with GFR.

A circulating metabolite of symmetric dimethylarginine and symmetric Nα-acetyl-dimethylarginine (FIG. 1) has also been identified and it may also correlate with GRF. The acetylation reaction of symmetric dimethylarginine occurs outside the cell resulting in the metabolite.

Because symmetric dimethylarginine is almost exclusively eliminated by the kidneys, this makes it an ideal candidate for a GFR biomarker. Thus, symmetric dimethylarginine is an emerging endogenous biomarker of kidney function that is already widely used in veterinary medicine.

Enzyme-linked immunosorbent assay (ELISA) to quantify symmetric dimethylarginine is commercially available. These methods involve a sample preparation step that includes the addition of an acylating derivatizing reagent to a sample suspected of containing symmetrical dimethylarginine prior to quantifying symmetric dimethylarginine. Symmetric dimethylarginine is quantitatively converted into Nα-acyl-SDMA by the acylation reagent. The antibody used in the ELISA product binds only the Nα-acylated form of symmetric dimethylarginine and not to free symmetric dimethylarginine.

More recently, a competitive immunoassay has been developed for free symmetric dimethylarginine using antibodies that detect only free symmetric dimethylarginine but do not cross-react with Nα-acylated symmetric dimethylarginine. The antibodies used in the competitive immunoassay are developed against a particular immunogen that produce antibodies specific to only free symmetric dimethylarginine. Haptens were used that are derivatives involving the chemical modification of the acidic carboxyl group (—COOH) of symmetric dimethylarginine. Antibodies were used to detect free symmetric dimethylarginine (i.e., symmetric dimethylarginine not part of a polypeptide chain) and show no or substantially no cross-reactivity with asymmetric dimethylarginine, L-arginine, and N-methylarginine.

Measurement of symmetric dimethylarginine can also be performed using liquid chromatography tandem mass spectrometry (LC-MS/MS) instruments. LC-MS/MS technology remains complex and requires a significant level of expertise for test development and operation. In addition, LC-MS/MS assays are not fully automated and require significant sample preparation and time before a result can be produced, increasing its turnaround time in comparison with automated assays for serum creatinine.

There is an ongoing need to develop tools that will enable detection of symmetrically dimethylated arginine analytes.

SUMMARY

The present disclosure provides methods for immunoassay of a symmetrically dimethylated arginine analyte. In particular, the present disclosure relates to the use of derivatives of symmetrical dimethylarginine in a signal producing immunoassay system. The present disclosure also relates to the use of immunogens of symmetrical dimethylarginine used for producing antibodies for capture of such analytes. As used herein, the term "symmetrically dimethylated arginine analyte" refers to analytes having an antibody binding epitope which is common to symmetric dimethylarginine. Analytes included in the symmetrically dimethylated arginine analytes include symmetric dimethylarginine (SDMA), symmetric Nα-acylated-dimethylarginine, such as symmetric Nα-acetyl-dimethylarginine, and SDMA-peptide derivatives, such as SDMA-Gly-Gly dipeptide.

In some embodiments, the present disclosure provides symmetric dimethylarginine haptens alkylated on the nitrogen atom of the α-amino group of symmetric dimethylarginine (FIG. 1). In certain embodiments, such haptens are used to produce antibodies specific for symmetrically dimethylated arginine analytes.

In some embodiments, the present disclosure provides symmetric dimethylarginine derivatives acylated on the nitrogen atom of the α-amino group of symmetric dimethylarginine (FIG. 1). In certain embodiments, such derivatives are used to produce conjugates useful in the immunoassays described herein.

In some embodiments, the present disclosure provides a polyclonal or monoclonal antibody that specifically binds to a symmetric dimethylarginine metabolite, such as symmetric Nα-acetyl-dimethylarginine (FIG. 1).

In some embodiments, the present disclosure provides a polyclonal or monoclonal antibody that specifically binds to free symmetric dimethylarginine, and symmetric Nα-acetylated-dimethylarginine protein (FIG. 1).

In some embodiments, the antibody may specifically bind to one or more of asymmetric dimethylarginine, L-arginine, and N-methylarginine (FIG. 2).

In some embodiments, the present disclosure provides a polyclonal or monoclonal antibody that specifically binds to free symmetric dimethylarginine and a SDMA-peptide derivative, such as SDMA-Gly-Gly dipeptide (FIG. 3).

In some embodiments, the present disclosure provides methods for the syntheses of symmetrical dimethylarginine haptens, immunogens and conjugates starting from symmetrical dimethylarginine. In some embodiments, the synthesis includes coupling through the nitrogen atom of the α-amino group of symmetrical dimethylarginine with a linking group to a protein or a label (e.g., a label enzyme).

An example of an embodiment of the present disclosure is a compound of Formula 1 shown below:

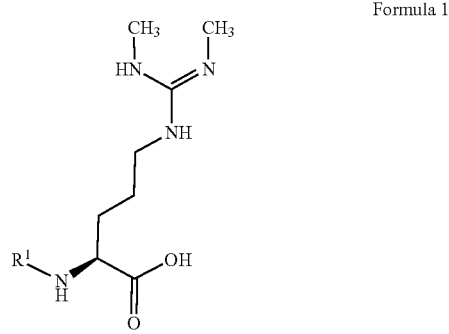

Formula 1 wherein:
R$^1$ is —Y—Z; and
Y is a linking group and Z is selected from hydrogen, OH, SH, S-acyl, O-alkyl, halogen, NH$_2$, epoxy, maleimidyl, haloacetamide, carboxyl, activated carboxyl, an immunogenic carrier, a protein, and a label.

Aspects of the present disclosure include antibodies. In some embodiments, an antibody of the present disclosure specifically binds to any of the compounds of the present disclosure, including any of the compounds of Formula 1 described elsewhere herein.

Nucleic acids that encode any of the antibodies of the present disclosure are also provided, as are expression vectors comprising such nucleic acids, and cells comprising such nucleic acids and expression vectors.

Also provided are methods of making the antibodies of the present disclosure. The methods include culturing a cell of the present disclosure under conditions suitable for the cell to express the antibody, wherein the antibody is produced.

Aspects of the present disclosure further include compositions. A composition of the present disclosure may include any of the antibodies, nucleic acids, expression vectors, and/or cells of the present disclosure.

Also provided are methods for determining an amount of at least one symmetrically dimethylated arginine analyte in a medium. In certain embodiments, such methods include combining in a medium a sample suspected of containing at least one symmetrically dimethylated arginine analyte, and an antibody of the present disclosure. Such methods further include determining the presence or absence of a complex comprising the symmetrically dimethylated arginine analyte and the antibody, wherein the presence of the complex indicates the presence of the symmetrically dimethylated arginine analyte in the sample.

Aspects of the present disclosure further include kits. According to some embodiments, the kits find use in determining an amount of at least one symmetrically dimethylated arginine analyte in a sample. In certain embodiments, a kit of the present disclosure includes any of the antibodies of the present disclosure, and instructions for using the antibody to determine an amount of at least one symmetrically dimethylated arginine analyte in a sample. Such kits may further include any of the compounds of Formula 1 of the present disclosure. According to some embodiments, a kit of the present disclosure includes any of the compounds of Formula 1 of the present disclosure, and instructions for using the compound to determine an amount of at least one symmetrically dimethylated arginine analyte in a sample. Such kits may further include any of the antibodies of the present disclosure.

BRIEF DESCRIPTION OF THE DRAWINGS

The present disclosure will be more fully understood from the following detailed description thereof taken in connection with the accompanying drawings which form a part of this application and in which:

FIG. 1 shows the chemical structures for symmetric dimethylarginine and symmetric Nα-acetyl-dimethylarginine.

FIG. 2 shows the chemical structures for asymmetric dimethylarginine, monomethylarginine and arginine.

FIG. 4 (right) shows the SDMA-SBAP (Nα-acyl-SDMA) hapten which is modified on the α-amino nitrogen atom of symmetric dimethylarginine, according to embodiments of the present disclosure.

FIG. 10 shows an antibody screening technique, according to embodiments of the present disclosure.

3K3, and monoclonal antibody 5H1/5K1, according to embodiments of the present disclosure.

Figure 12:
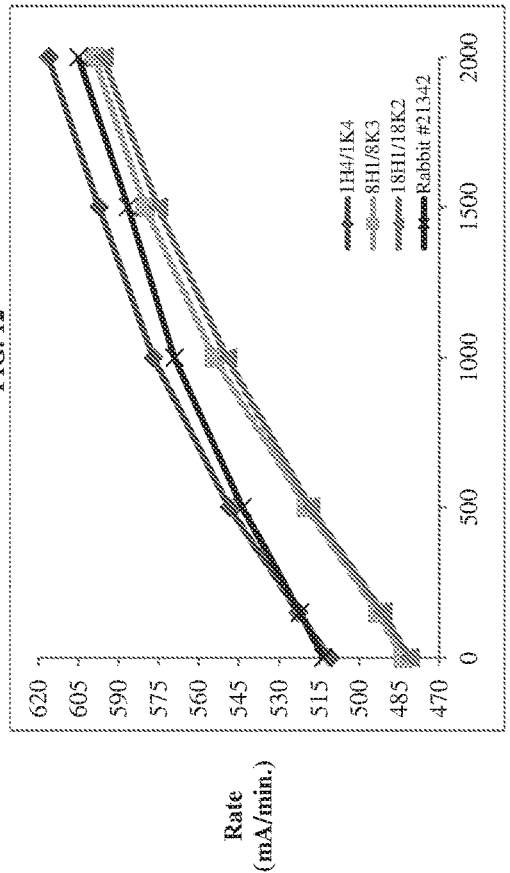

FIG. 12 shows a graph of a symmetric dimethylarginine calibration curve using rabbit polyclonal antibody #21342, monoclonal antibody 1H4/1K4, monoclonal antibody 8H1/8K3, and monoclonal antibody 18H1/18K2, according to embodiments of the present disclosure.

Figure 13:
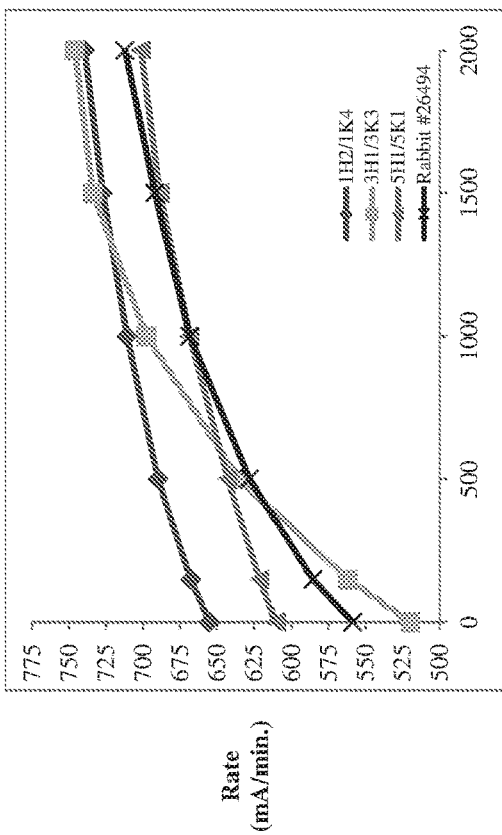

FIG. 13 shows a graph of a symmetric Nα-acetyl-dimethylarginine calibration curve using rabbit polyclonal antibody #26494, monoclonal antibody 1H2/1K4, monoclonal antibody 3H1/3K3, monoclonal antibody 5H1/5K1, according to embodiments of the present disclosure.

Figure 14:
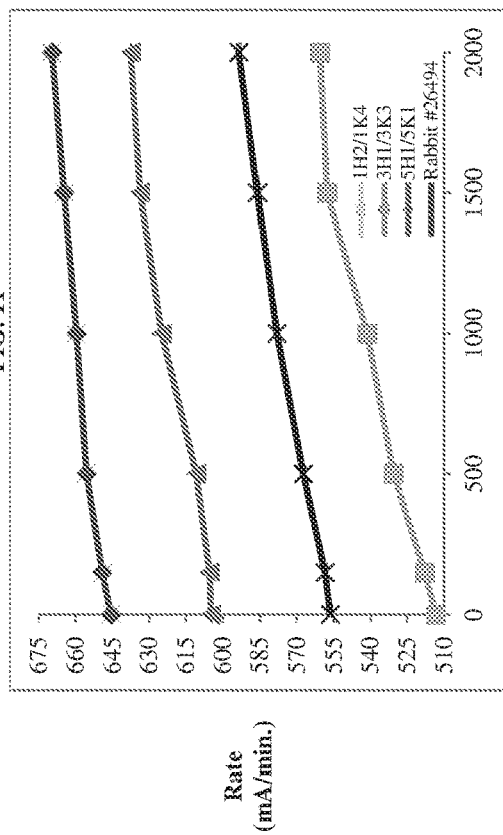

FIG. 14 shows a graph of a symmetric Nα-acetyl-dimethylarginine calibration curve using rabbit polyclonal antibody #21342, monoclonal antibody 1H4/1K4, monoclonal antibody 8H1/8K3, and monoclonal antibody 18H1/18K2, according to embodiments of the present disclosure.

Figure 15:
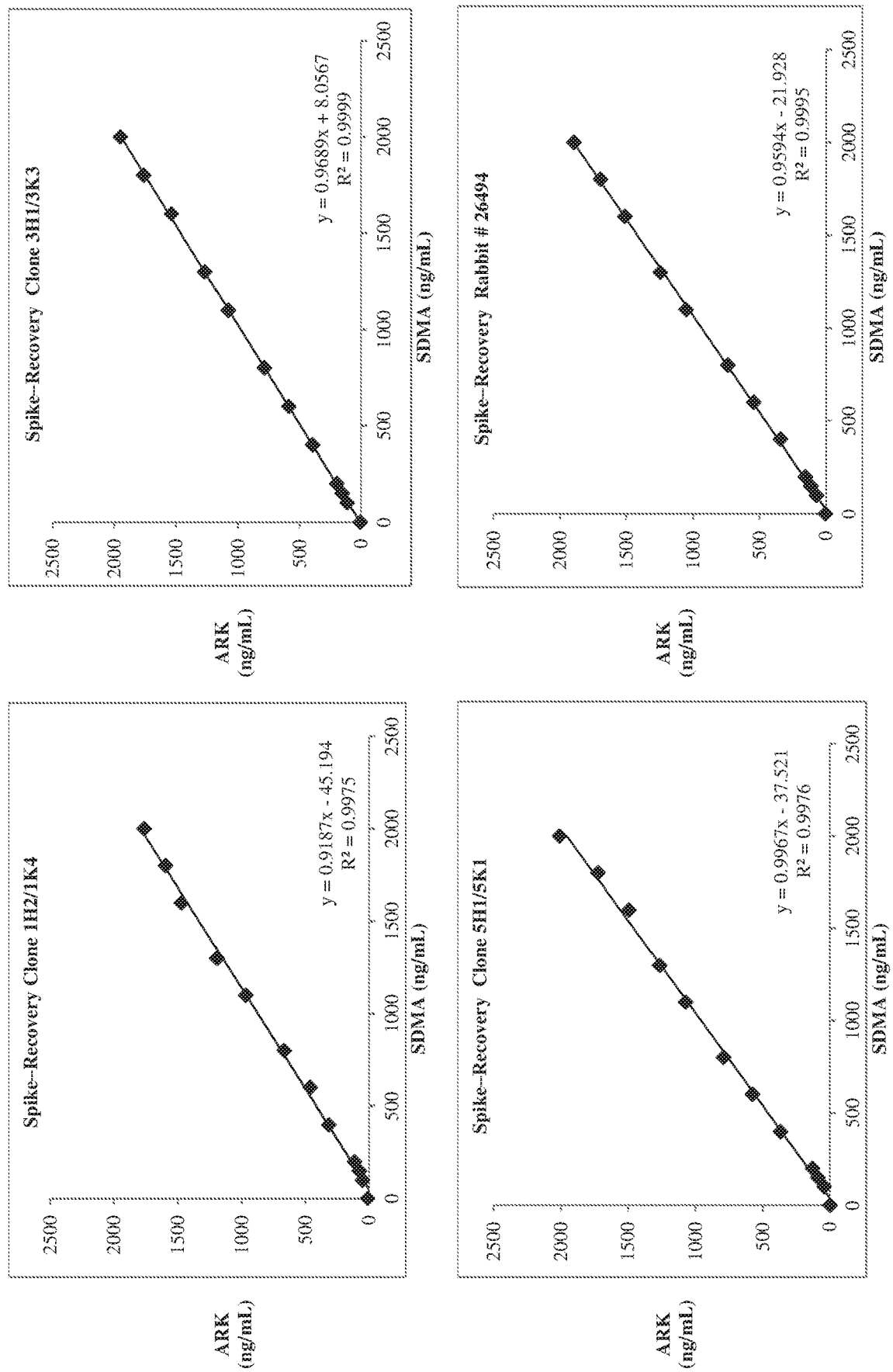

FIG. 15 shows graphs of spike-recovery experiments of symmetric dimethylarginine using rabbit polyclonal antibody #26494 (bottom right), monoclonal antibody 1H2/1K4 (top left), monoclonal antibody 3H1/3K3 (top right), and monoclonal antibody 5H1/5K1 (bottom left), according to embodiments of the present disclosure.

Figure 16:
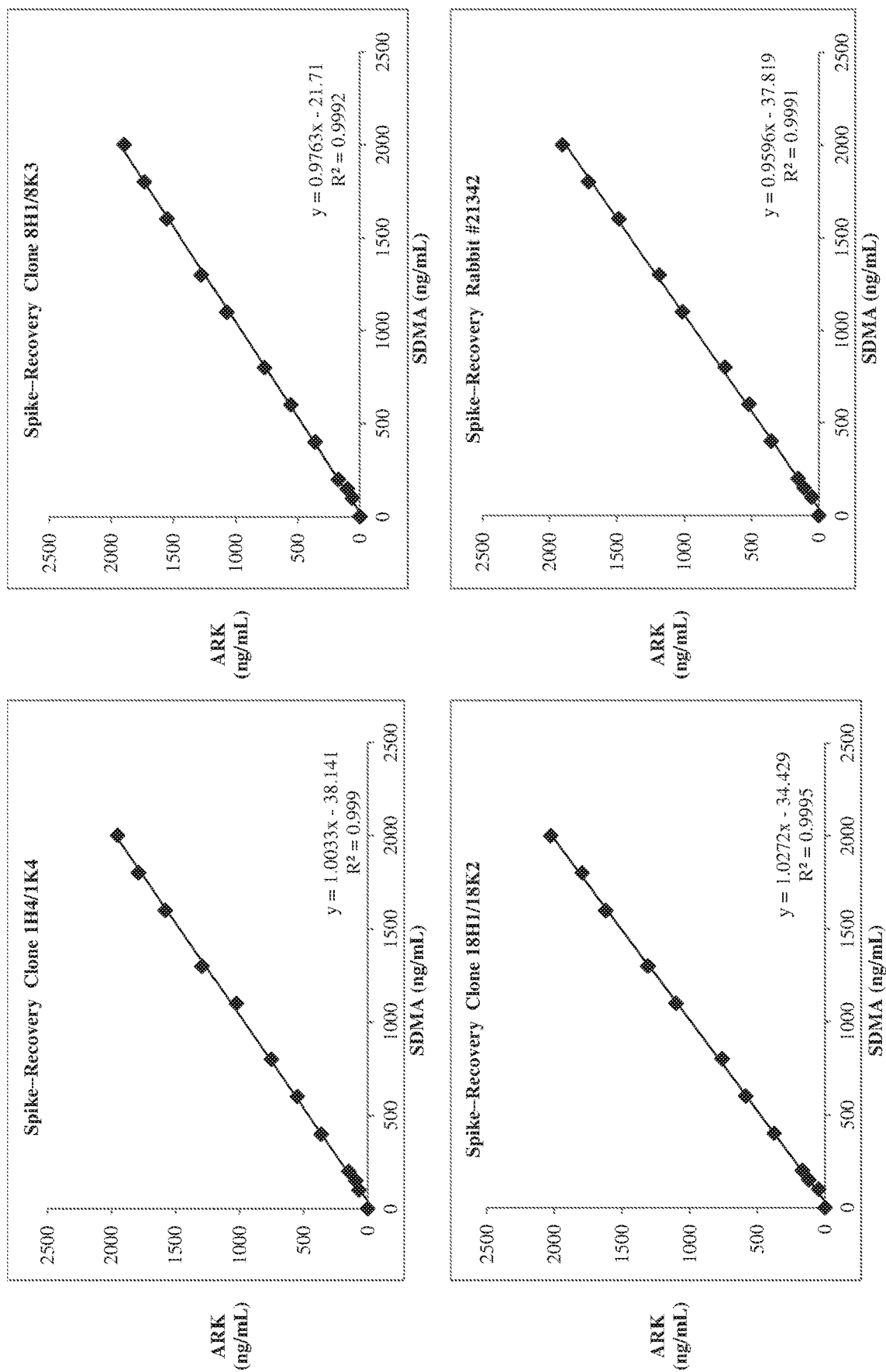

FIG. 16 shows graphs of spike-recovery experiments of symmetric dimethylarginine using rabbit polyclonal antibody #21342 (bottom right), monoclonal antibody 1H4/1K4 (top left), monoclonal antibody 8H1/8K3 (top right), and monoclonal antibody 18H1/18K2 (bottom left), according to embodiments of the present disclosure.

Figure 17:
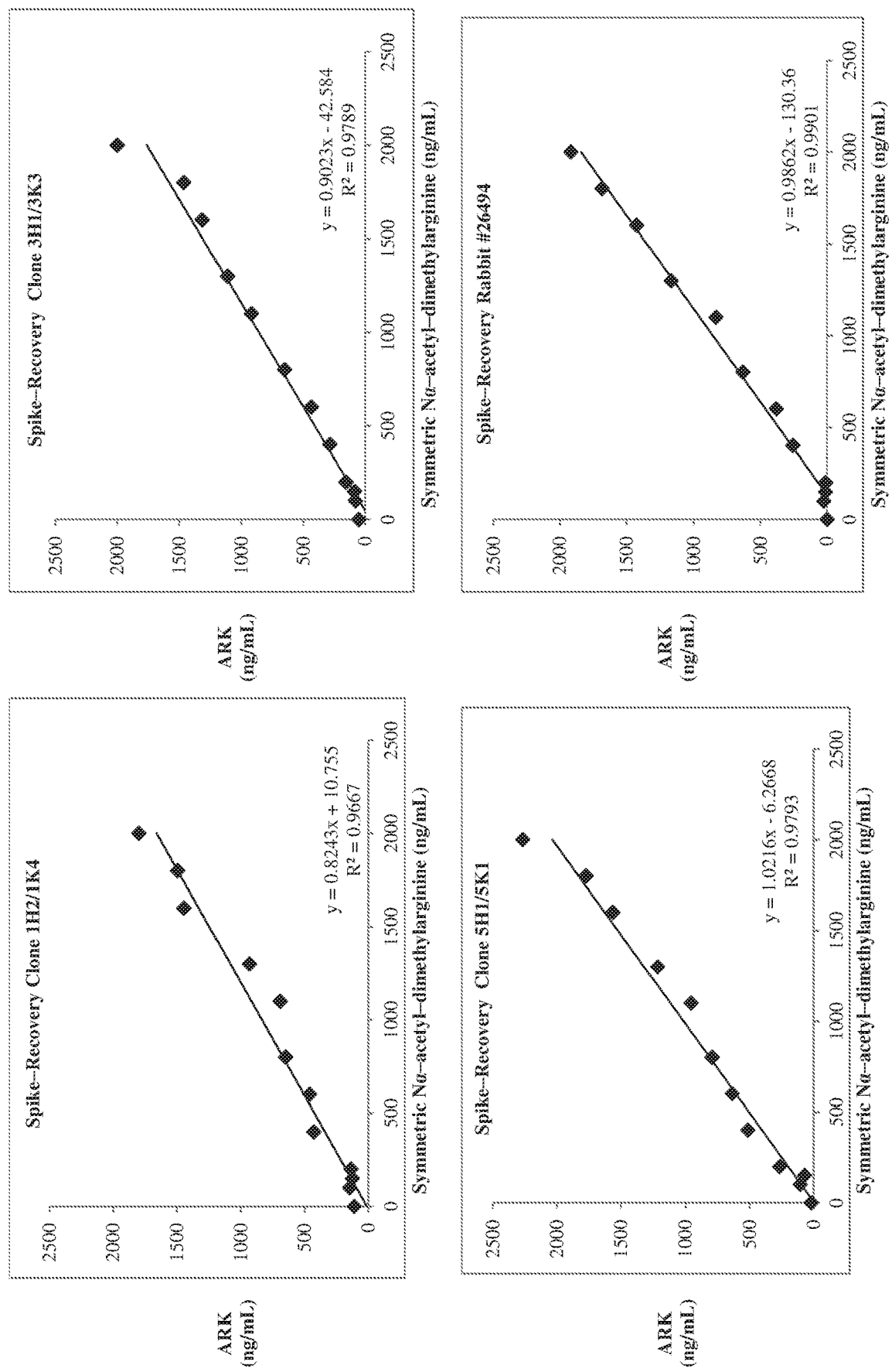

FIG. 17 shows graphs of spike-recovery experiments of symmetric Nα-acetyl-dimethylarginine using rabbit polyclonal antibody #26494 (bottom right), monoclonal antibody 1H2/1K4 (top left), monoclonal antibody 3H1/3K3 (top right), monoclonal antibody 5H1/5K1 (bottom left), according to embodiments of the present disclosure.

Figure 18:
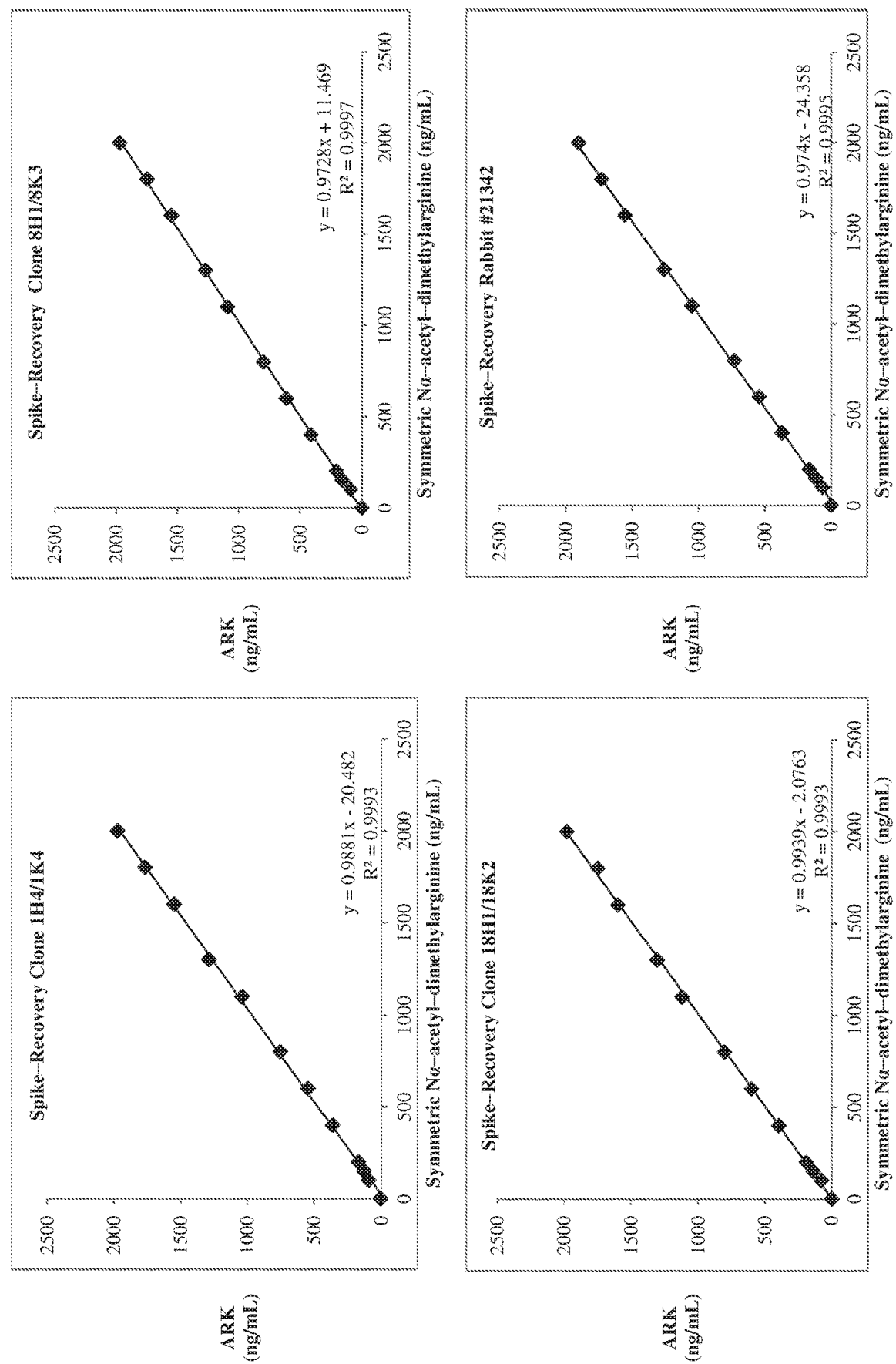

FIG. 18 shows graphs of spike-recovery experiments of symmetric Nα-acetyl-dimethylarginine using rabbit polyclonal antibody #21342 (bottom right), monoclonal antibody 1H4/1K4 (top left), monoclonal antibody 8H1/8K3 (top right), and monoclonal antibody 18H1/18K2 (bottom left), according to embodiments of the present disclosure.

Figure 19:
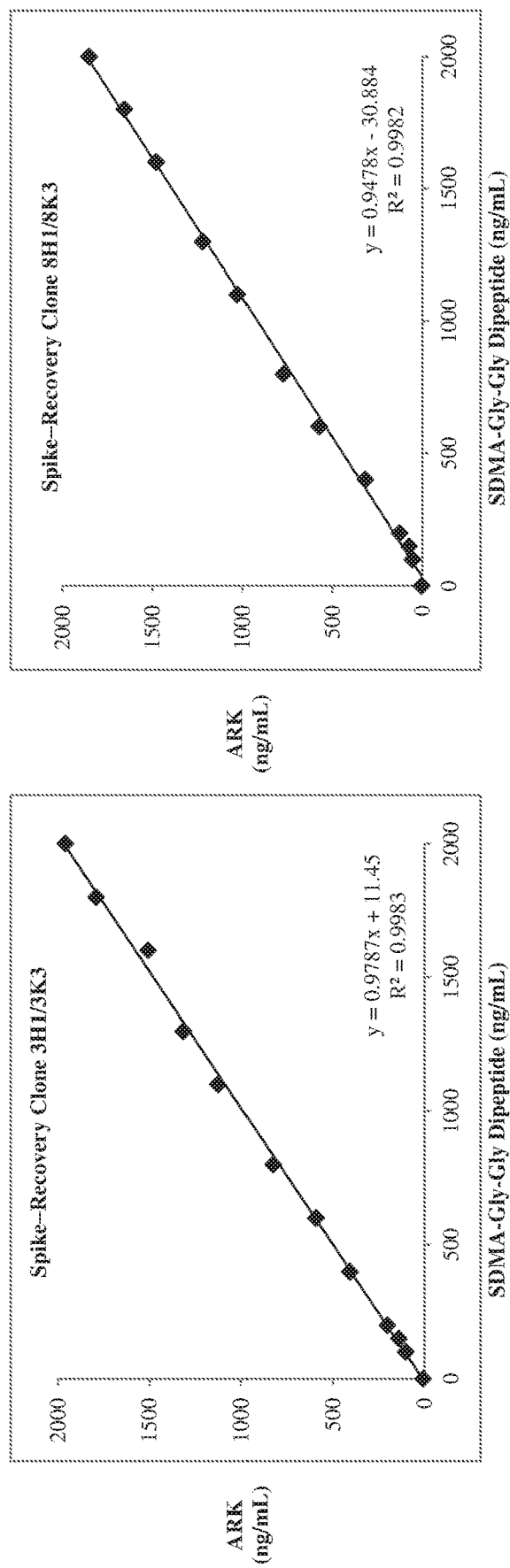

FIG. 19 shows graphs of spike-recovery experiments of SDMA-Gly-Gly dipeptide using monoclonal antibody 3H1/3K3 (left) and monoclonal antibody 8H1/8K3 (right), according to embodiments of the present disclosure.

Figure 20:
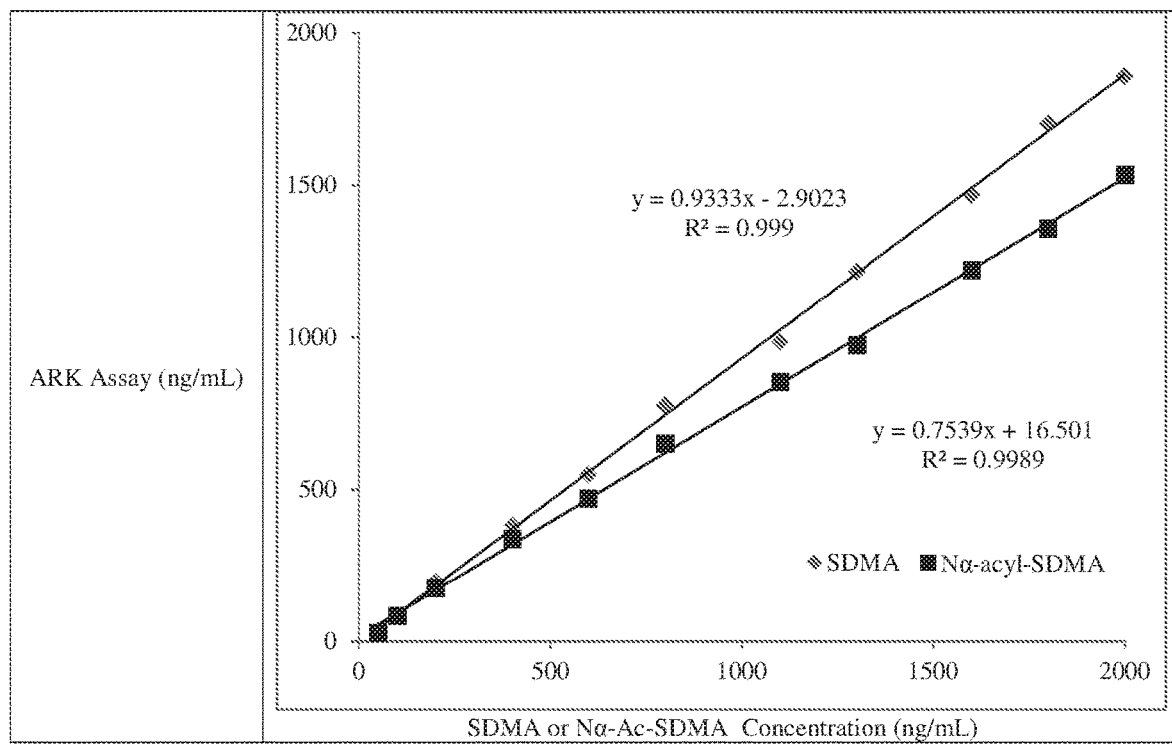

FIG. 20 shows a graph of spike-recovery experiments of SDMA and symmetric Nα-acetyl-dimethylarginine using rabbit polyclonal antibody #27410, according to embodiments of the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Before proceeding further with the description of the specific embodiments of the present disclosure, a number of terms will be defined.

Definitions

Analyte

A compound or composition to be measured, the material of interest. The analyte is a member of a specific binding pair (sbp) and may be a ligand, which is mono- or polyvalent, usually antigenic or haptenic, and is a single compound or plurality of compounds which share at least one common epitopic or determinant site.

Sample Suspected of Containing Analyte

Any sample which is reasonably suspected of containing analyte can be analyzed by the methods of the present disclosure. Such samples can include human, animal or man-made samples. The sample can be prepared in any convenient medium which does not interfere with the assay. Typically, the sample is an aqueous solution or a natural fluid, such as, but not limited to, urine, whole blood, serum, plasma, cerebral-spinal fluid, or saliva. In some instances, the sample is serum.

Measuring the Amount of Analyte

Quantitative, semiquantitative, and qualitative methods as well as all other methods for determining analyte are considered to be methods of measuring the amount of analyte. For example, a method which merely detects the presence or absence of analyte in a sample suspected of containing an analyte is considered to be included within the scope of the present disclosure.

Synonyms for the phrase "measuring the amount of analyte" which are contemplated within the scope of the present disclosure include, but are not limited to, detecting, measuring, or determining analyte; detecting, measuring, or determining the presence of analyte; detecting, or determining the amount of analyte; and detecting, measuring or determining the concentration of analyte.

Member of a Specific Binding Pair

A member of a specific binding pair (sbp member) is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, or the like. These will usually be members of an immunological pair such as antigen-antibody.

Ligand

Any organic compound for which a receptor naturally exists or can be prepared. For example, in one context of the present disclosure, the analyte is a ligand and the present disclosure provides methods for determining the amount or concentration of the analyte which is a ligand.

Receptor

A receptor is any compound or composition capable of recognizing a particular spatial and polar organization of a molecule. These organized areas of a molecule are referred to as epitopic or determinant sites. Illustrative naturally occurring receptors include antibodies and enzymes.

Epitope

"Epitope" is a molecular region on the surface of an antigen capable of eliciting an immune response and of combining with the specific antibody produced by such a response, also called determinant, antigenic determinant. In reference to a hapten (such as symmetric dimethylarginine) an antibody can be generated against the non-antigenic hapten molecule by conjugating the hapten to an immunogenic carrier. An antibody is then generated which recognizes an "epitope" defined by the hapten.

Linking Group

A linking group is a portion of a structure which connects two or more substructures. A linking group has at least one uninterrupted chain of atoms extending between the substructures. The atoms of a linking group are themselves connected by chemical bonds. The number of atoms in a linking group is determined by counting the atoms other than hydrogen.

Conjugate

A conjugate is a molecule comprised of two or more substructures bound together through a linking group to form a single structure. The binding can be made by connecting the subunits through a linking group. Within the context of the present disclosure, a conjugate can include a glucose-6-phosphate dehydrogenase (G6PDH) enzyme attached to a hapten, sbp member or analyte analog, such as a conjugate where a G6PDH mutant enzyme is used (e.g., recombinant G6PDH as described in U.S. Pat. Nos. 6,455,288, 6,090,567, and 6,033,890). Within the context of the present disclosure, G6PDH may also be referred to as an enzyme, such as a G6PDH enzyme, or a label, such as a G6PDH label. In some cases, a conjugate can include a label (e.g., a label protein) including, but not limited to, G6PDH, alkaline phosphatase, β-galactosidase, and horse radish peroxidase, or a chemical label such as a fluorescent, luminescent or colorimetric molecule attached to a hapten, sbp member or analyte analog.

Conjugation

Conjugation is any process where two subunits are linked together to form a conjugate. The conjugation process can be comprised of any number of steps, for example as described herein.

Hapten

Haptens are capable of binding specifically to corresponding antibodies, but usually do not themselves act as immunogens for preparation of the antibodies. Antibodies which recognize a hapten can be prepared against compounds comprised of the hapten linked to an immunogenic carrier.

Symmetrically Dimethylated Arginine Analyte

"Symmetrically dimethylated arginine analyte" refers to analytes having an antibody-binding epitope which is common to symmetric dimethylarginine. Analytes included in symmetrically dimethylated arginine analytes include symmetric dimethylarginine (SDMA), symmetric Nα-acylated-dimethylarginine, such as symmetric Nα-acetyl-dimethylarginine, and SDMA-peptide derivatives, such as SDMA-Gly-Gly dipeptide.

Derivative

The term "derivative" refers to a chemical compound or molecule made from a parent compound by one or more chemical reactions.

Analog

The term "analog" is a compound having a structure similar to that of another compound, but differing from it in respect to a certain component. It can differ in one or more atoms, functional groups, or substructures, which are replaced with other atoms, groups, or substructures.

Label

A "label," "detector molecule," "reporter" or "detectable marker" is any molecule which produces, or can be induced to produce, a detectable signal. The label can be conjugated to an analyte, immunogen, antibody, or to another molecule such as a receptor or a molecule that can bind to a receptor such as a ligand, particularly a hapten or antibody. A label can be attached directly or indirectly by a linking group. Non-limiting examples of labels include radioactive isotopes (e.g., $^{125}$I), enzymes (e.g. β-galactosidase, peroxidase), G6PDH (e.g., mutant G6PDH, such as recombinant G6PDH as described in U.S. Pat. Nos. 6,455,288, 6,090,567, and 6,033,890), enzyme fragments, enzyme substrates, enzyme inhibitors, coenzymes, catalysts, fluorophores (e.g., rhodamine, fluorescein isothiocyanate or FITC, or Dylight 649), dyes, chemiluminescers and luminescers (e.g., dioxetanes, luciferin), or sensitizers.

Immunogen

The term "immunogen" refers to a substance capable of eliciting, producing, or generating an immune response in an organism.

Immunogenic Carrier

An "immunogenic carrier," as used herein, is an immunogenic substance, commonly a protein, that can join at one or more positions with haptens, thereby enabling the production of antibodies that can specifically bind with these haptens. Examples of immunogenic carrier substances include, but are not limited to, proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Protein

The terms "protein", "polypeptide" and "peptide" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, polypeptides having modified peptide backbones, and fusion proteins.

Signal Producing System

The "signal producing system" is utilized in assays for analytes and may have one or more components, at least one component being a detectable label (e.g., G6PDH, such as a mutant G6PDH). The signal producing system generates a signal that relates to the presence or amount of analyte in a sample. The signal producing system includes all of the reagents required to produce a measurable signal. For purposes of the present disclosure, typically, the G6PDH or a label protein (e.g., alkaline phosphatase, β-galactosidase or horse radish peroxidase) is conjugated to a sbp member analogous to the analyte.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, such as by measurement of electromagnetic radiation, e.g., by visual examination. In some instances, the signal producing system includes a chromophoric substrate and an enzyme label (e.g., mutant G6PDH enzyme), where chromophoric substrates are enzymatically converted to dyes which absorb light in the ultraviolet or visible region.

Isolated

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated", but the same antibody separated from the coexisting materials of its natural state is "isolated", as the term is employed herein. Antibodies may occur in a composition, such as an immunoassay reagent, which are not naturally occurring compositions, and therein remain isolated antibodies within the meaning of that term as it is employed herein.

Cross-Reactivity

"Cross-reactivity" refers to the reaction of an antibody with an antigen that was not used to induce that antibody. "Cross-reactivity" may be determined in a quantitative immunoassay by establishing a standard curve using known dilutions of the target analyte. The standard curve is then used to calculate the apparent concentration of the interfering substance present in various known amounts in samples assayed under similar condition. The cross-reactivity is the apparent concentration divided by the actual concentration multiplied by 100.

Calibration and Control Material

The phrase "calibration and control material" refers to any standard or reference material containing a known amount of an analyte. A sample suspected of containing an analyte and the corresponding calibration material are assayed under similar conditions. The concentration of analyte is calculated by comparing the results obtained for the unknown specimen or sample containing known concentration of analyte with the results obtained for the standard. This is commonly done by constructing or generating a calibration curve.

Sensitivity

Is used in the sense of detection limit, i.e., the smallest amount of an analyte giving a signal that is distinguishable from the signal obtained in the absence of analyte.

Spike-Recovery

"Spike-recovery" refers to an assay measuring the amount of analyte (recovery) in a sample mixture compared to a known amount of the analyte added (spiked) to the sample mixture. The measuring the amount of analyte may be expressed in terms of concentration (ng/mL) or a percentage (%).

Substantial Change in Enzyme Activity

A change in activity of an enzyme sufficient to allow detection of an analyte when the enzyme is used as a label in an assay for the analyte. Typically, the enzyme's activity is reduced 10 to 100%, such as 20 to 99%, or 30 to 95%.

Inhibitory Antibody

An antibody capable of inhibiting the activity of an enzyme or an enzyme-ligand conjugate upon binding an epitope present on the enzyme. Such antibodies are distinguished from anti-ligand antibodies capable of inhibiting the enzyme activity of enzyme-ligand conjugates upon binding to the ligand.

Modulation

In an assay experiment "modulation" refers to hapten or analyte attached to a label such as an enzyme and an analyte in a sample suspected of containing the analyte competing for analyte-antibody binding sites, thus modulating the amount of enzymatic product formed (see FIG. 10).

Maximum Inhibition

"Maximum inhibition" refers to an antibody capable of inhibiting the activity of an enzyme or an enzyme-ligand conjugate upon binding an epitope present on the enzyme when excess antibody is added to the assay and the signal obtained in the absence of analyte.

Ancillary Materials

Various ancillary materials will frequently be employed in an assay in accordance with the present disclosure. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Compounds, Conjugates and Syntheses Thereof

Homogeneous enzyme immunoassays depend on the availability of enzyme-sbp member conjugates whose enzyme activity can be strongly modulated on binding of the sbp partner. The present disclosure provides enzyme-sbp member conjugates and antibodies for conducting assays that are useful in homogeneous immunoassays.

In certain embodiments, protein immunogens are synthesized and used to prepare antibodies specific for compounds, such as a symmetically dimethylated arginine analyte. The antibodies may be used in methods for detecting a symmetically dimethylated arginine analyte in a sample suspected of containing the analyte. Label conjugates are prepared and may be employed in the above methods. Effective screening of samples for the presence of one or more symmetrically dimethylated arginine analytes as referred to above may be realized.

The immunogens and label conjugates may involve a derivative of symmetric dimethylarginine linked through the nitrogen atom of the α-amino group of symmetric dimethylarginine to a protein or a label. In some instances, the conjugate may be referred to herein as a protein conjugate or a label conjugate, respectively.

Compounds of the present disclosure include compounds useful for producing antibodies according to the present disclosure. In addition, compounds of the present disclosure include conjugates useful for the immunoassays described herein. In certain embodiments, the compounds include a compound of Formula 1:

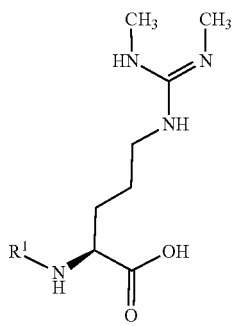

wherein:
$R^1$ is —Y—Z;
Y is a linking group; and
Z is selected from the group consisting of hydrogen, OH, SH, S-acyl, O-alkyl, halogen, $NH_2$, epoxy, maleimidyl, haloacetamide, carboxyl, activated carboxyl, an immunogenic carrier, a protein, and a label.

In some embodiments, Z is a protein. For example, the protein can be an immunogenic carrier. The immunogenic carrier can be conjugated to a symmetric dimethylarginine hapten, thereby enabling the production of antibodies that can specifically bind with the hapten. For example, the immunogenic carrier can be selected from a hemocyanin, a globulin, an albumin, and a polysaccharide. In some instances, the immunogenic carrier is bovine serum albumin (BSA). In some instances, the immunogenic carrier is keyhole limpet hemocyanin (KLH). In certain embodiments, the immunogenic carrier may be modified to include one or more functional groups. The functional group on the modified immunogenic carrier can be a reactive functional group that facilitates attachment of the immunogenic carrier to the linking group in the compound of Formula 1.

In some embodiments, a symmetric dimethylarginine hapten is alkylated on the nitrogen atom of the α-amino group of symmetric dimethylarginine (FIG. 1). As such, in some cases, the linking group comprises an alkyl or substituted alkyl group attached to the nitrogen atom of the α-amino group of symmetric dimethylarginine (i.e., attached to the $R^1$-nitrogen atom). In certain embodiments, such haptens are used to produce antibodies specific for symmetrically dimethylated arginine analytes.

In certain embodiments, Z is a label. The label is a molecule which produces, or can be induced to produce, a detectable signal. For example, the label can be an enzyme, such as an enzyme selected from an alkaline phosphatase, a β-galactosidase and a horse radish peroxidase. In some embodiments, the label is an enzyme, where the enzyme is glucose-6-phosphate dehydrogenase (G6PDH). In some instances, the G6PDH is a mutant G6PDH, which includes one or more amino acid residue substitutions relative to the wild-type form. For example, the mutant G6PDH can include a cysteine substitution, e.g., a cysteine substitution in each subunit of the G6PDH enzyme. In some cases, the linking group can be attached to the G6PDH enzyme at the cysteine residue. In certain embodiments, the label may be modified to include one or more functional groups. The functional group on the modified label can be a reactive functional group that facilitates attachment of the label to the linking group in the compound of Formula 1.

In some embodiments, a symmetric dimethylarginine derivative is acylated on the nitrogen atom of the α-amino group of symmetric dimethylarginine (FIG. 1). As such, in some cases, the linking group comprises an acyl or substituted acyl group attached to the nitrogen atom of the α-amino group of symmetric dimethylarginine (i.e., attached to the $R^1$-nitrogen atom). In certain embodiments, such derivatives are used to produce conjugates useful in the immunoassays described herein.

In certain embodiments, Z is a protein. The protein can be any convenient protein, which includes amino acid residues, such as a dipeptide, tripeptide, and the like, in any number of such amino acid residues, such as 2 or more, 3 or more, 4 or more, 5 or more, 6 or more, 7 or more, 8 or more, 9 or more, 10 or more, etc. In certain embodiments, the protein may be modified to include one or more functional groups. The functional group on the modified protein can be a reactive functional group that facilitates attachment of the protein to the linking group in the compound of Formula 1. In some instances, the protein is acylated. In some instances, the protein is alkylated.

The linking group may include about 1 to 25 atoms (excluding hydrogen atoms) and may include a chain of from 2 to 15 atoms (excluding hydrogen atoms), each independently selected from carbon, oxygen, sulfur, nitrogen, halogen and phosphorous. In some embodiments, the linking group includes 1 to 15 carbon atoms and/or 0 to 6 heteroatoms. Examples of linking groups include, but are not limited to, —$(CH_2)_nC(O)$—, —$C(O)(CH_2)_n$—, —$C(O)(CH_2)_nNHC(O)$—, —$C(O)(CH_2)_nNHC(O)(CH_2)_n$—, —$(CH_2)_nSCH_2C(O)$—, —$(CH_2)_nC(O)NH(CH_2)_n$—, —$(CH_2)_nNHC(O)$—, —$(CH_2)_nNHC(O)(CH_2)_n$—, —$NH(CH_2)_nC(O)$—, —$(CH_2)_n$—, and —$(CH_2)_n$(heterocyclyl)S$(CH_2)_nC(O)$—, and n is an integer from 1 to 10, and including acid salts thereof. In certain embodiments, the linking group is —$C(O)(CH_2)_nNHC(O)(CH_2)_n$—, such as —$C(O)(CH_2CH_2)NHC(O)(CH_2)$—. In certain embodiments, the linking group is —$(CH_2)_n$(heterocyclyl)S$(CH_2)_nC(O)$—, such as —$(CH_2CH_2CH_2CH_2)$(2,5-dioxopyrrolidin-1-yl)S$(CH_2)C(O)$—.

The number of heteroatoms in the linking group may range from 0 to 6, such as from about 1 to 5, or from 2 to 5, or from 3 to 5. The linking agents may be aliphatic or aromatic. When heteroatoms are present, oxygen may be present as oxo or oxy, bonded to carbon, sulfur, nitrogen or phosphorous; nitrogen may be present as nitro, nitroso or amino, bonded to carbon, oxygen, sulfur or phosphorous; sulfur can be analogous to oxygen; phosphorous can be bonded to carbon, sulfur, oxygen or nitrogen, such as phosphonate and phosphate mono or di-ester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

In certain embodiments, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities can be linked to amine groups, carboxyl groups, active olefins, alkylating agents, e.g., bromoacetyl. Where an amine and carboxylic acid or its nitrogen derivative or phosphoric acid is linked, amides, amidines and phosphoramides can be formed. Where mercaptan and activated olefin are linked, thioethers can be formed. Where a mercaptan and an alkylating agent are linked, thioethers can be formed. Where aldehyde and an amine are linked under reducing conditions, an alkylamine can be formed. Where a carboxylic acid or phosphate acid and an alcohol are linked, esters can be formed. Various linking groups are described, see, for example, Cautrecasas, *J. Biol. Chem.* (1970) 245:3059.

To develop an assay for symmetric dimethylarginine, the chemical structure of symmetric dimethylated arginine analytes is used. For example, asymmetric dimethylarginine has two methyl groups added to one of the terminal nitrogen atoms of the guanidium group (see FIG. 2). Monomethyl arginine has a single methyl group on one of the terminal nitrogen atoms (FIG. 2). Symmetric dimethylarginine has two methyl groups, one methyl group added to each of the terminal nitrogen atoms of the guanidine group (FIG. 1). The specific symmetrical methylation of the chemical structures are retained to prepare immunogens and raise antibodies accordingly.

Figure 3:
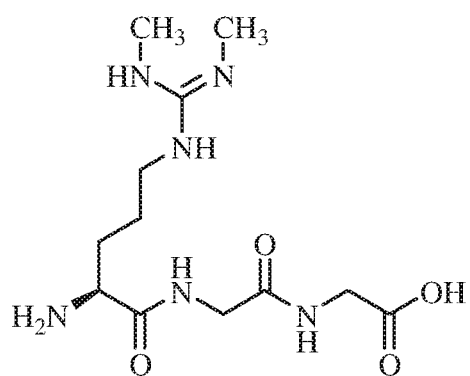
FIG. 3 shows chemical structures for an SDMA-Gly-Gly dipeptide.
Figure 4:
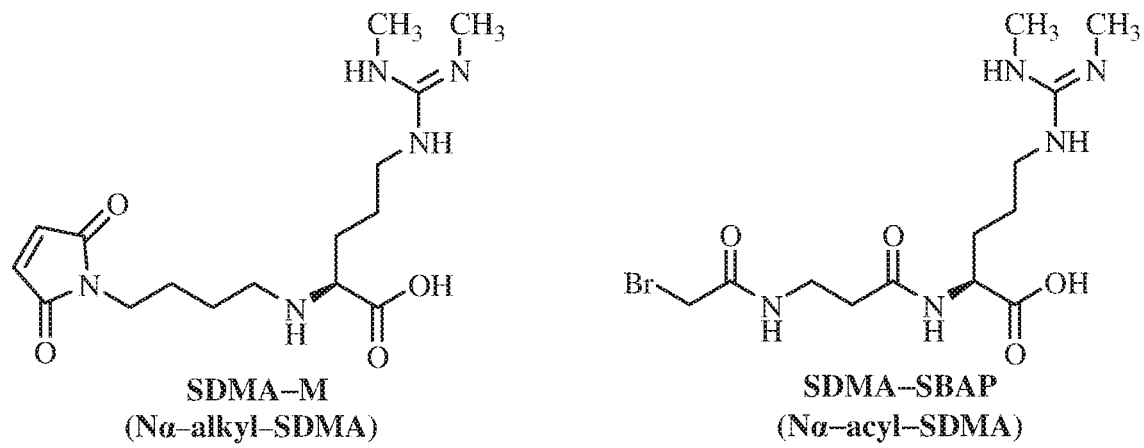
FIG. 4 (left) shows the SDMA-M (Nα-alkyl-SDMA) hapten which is modified on the α-amino nitrogen atom of symmetric dimethylarginine, according to embodiments of the present disclosure.

The present disclosure provides for the design of symmetric dimethylarginine haptens and immunogens by modification of the nitrogen atom of the α-amino group of symmetric dimethylarginine. Haptens SDMA-M and SDMA-SBAP of the present disclosure are shown in FIG. 4. Placement of a linking group at the amine nitrogen of symmetric dimethylarginine provides for antibodies that may specifically react with a symmetrically dimethylated arginine analyte because the analytes share the symmetric dimethylated guanidine group. The present disclosure thus provides symmetric dimethylarginine derivatives (i.e., symmetrically dimethylated arginine analytes) and immunogens useful with the various types of immunoassays described herein (see, e.g., FIG. 10).

Compounds useful for producing antibodies and conjugates according to the present disclosure can be synthesized in accordance with the general synthetic methods described below. Compounds of Formula 1 can be prepared by standard methods. The following reaction schemes are only meant to represent examples of the methods and are in no way meant to limit the present disclosure.

a) Haptens

Attachment of maleimide functionality to the nitrogen atom of the α-amino group of symmetric dimethylarginine may be accomplished through use of 4-maleimido-1-butanal (4) shown in Scheme 1, the preparation of which is described in Example 1. For the alkylation reaction on the nitrogen atom of the α-amino group of symmetric dimethylarginine, AcOH and $NaBH_3CN$ can be added to a solution of 4-maleimido-1-butanal (4) and symmetric dimethylarginine in MeOH. The resulting mixture can be stirred at room temperature for 3 hours. The reaction can be quenched with water and purified by reverse phase chromatography to give the hapten SDMA-M (FIG. 4).

Attachment of a linking group to the nitrogen atom of the α-amino group of symmetric dimethylarginine may be accomplished through use of N-tert-(butoxycarbonyl)-3-alanine (6) shown in Scheme 2, the preparation of which is described in Example 2. Acylation of symmetrical dimethylarginine with N-tert-(butoxycarbonyl)-3-alanine (6) is also described in Example 2. Deprotection as described in Example 2 may provide the compound (8) which may be further elaborated by reacting with N-succinimidyl bromoacetate (9) and DIPEA in DMF. Solvent can be removed under vacuum. The crude product can be dissolved in MeCN and water and then purified with reverse phase chromatography to give the product SDMA-SBAP (FIG. 4). The resulting product (SDMA-SBAP) can be linked to thiol containing proteins.

Removal of the t-Boc protecting group from the linking group can produce the compound (8). Suitable protecting groups are described in detail in patents and articles in the technical literature. See, for example, "Principles of Peptide Synthesis" (M. Bodanszky, Springer Verlag, Berlin, Heidelberg, N.Y., Tokyo (1984)). Examples of such protecting groups, by way of example and not limitation, are t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentylethoxycarbonyl, bromobenzyloxy, carbamyl, formyl, and the like. The particular protecting group chosen may depend on the nature of the reaction to be performed and the conditions of such reaction such as temperature, pH, and so forth.

b) Immunogen

Maleimide functionalized haptens (e.g. SDMA-M) may be conjugated to proteins. Activation of protein lysine residues by acylation of the epsilon-nitrogen with N-succinimidyl S-acetylthioacetate (SATA), followed by subsequent hydrolysis of the S-acetyl group with hydroxylamine produces a nucleophilic sulfhydryl group. Conjugation of the sulfhydryl activated protein with the maleimide derivatized hapten proceeds via a Michael addition reaction. Suitable proteins (immunogenic carriers) include, but are not limited to, keyhole limpet hemocyanin, bovine thyroglobulin, and ovalbumin.

Figure 5:
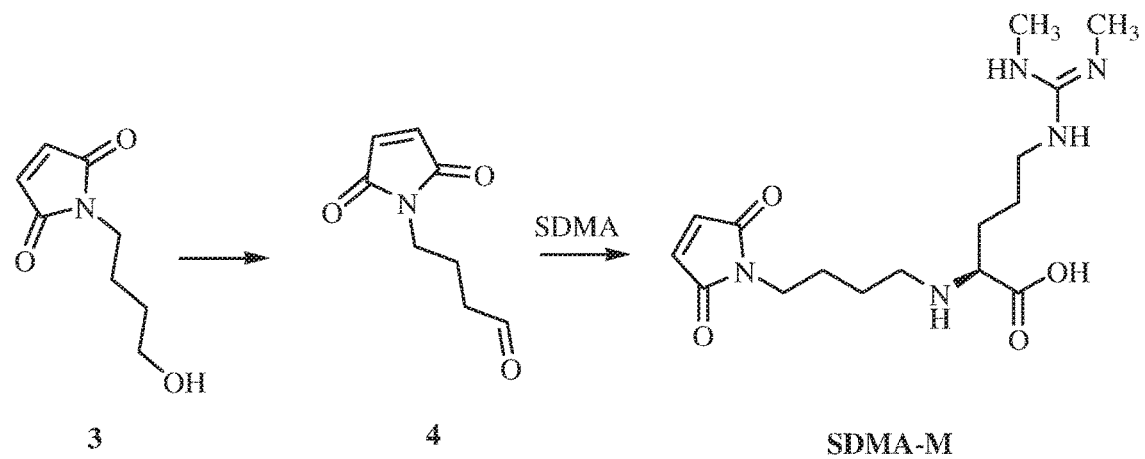
FIG. 5 shows the synthesis scheme for the SDMA-M (Nα-alkyl-SDMA) hapten, according to embodiments of the present disclosure.

Compound SDMA-M includes the maleimide functionality for thiol modification of thiol containing proteins. The synthesis of symmetric dimethylarginine immunogen SDMA-M-SH-KLH with a linking group on the nitrogen atom of the α-amino group of symmetric dimethylarginine begins with the synthesis of SDMA-M as shown in FIG. 5, the preparation of which is described in Example 1. Reaction of amines from keyhole limpet hemocyanin (KLH) with N-succinimidyl S-acetylthioacetate can produce protected sulfhydryls that can be subsequently deprotected by hydroxylamine for reaction with SDMA-M. Reaction of thiol modified KLH with SDMA-M in sodium phosphate (0.1 M, pH=8.0) buffer solution can produce the desired immunogen SDMA-M-SH-KLH as show in FIG. 8. The immunogen SDMA-M-SH-KLH can be purified by chromatography, such as on a Sephadex G-25 column with buffer solution. The concentration of immunogen SDMA-M-SH-KLH can be measured using a protein assay, such as, but not limited to a Pierce™ Rapid Gold BCA protein assay kit. The immunogen SDMA-M-SH-KLH can be used for the immunization of rabbits for antibody production.

c) Enzyme Conjugate

Figure 7:
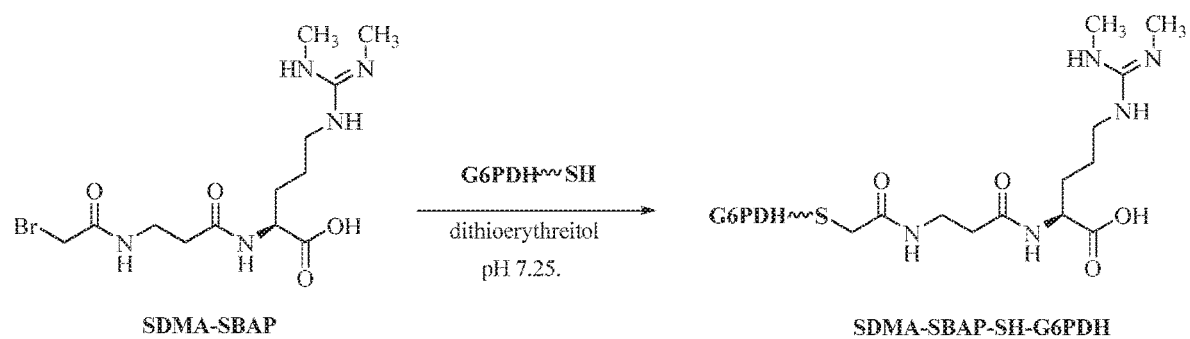
FIG. 7 shows the synthesis scheme for SDMA-M-SH-G6PDH, according to embodiments of the present disclosure.

Hapten SDMA-SBAP with bromoacetamide functionality can be used for reaction with proteins containing a thiol group. Conjugation of SDMA-SBAP to cysteine containing G6PDH is shown in FIG. 7, the preparation of which is described in Example 2.

Hapten SDMA-M can be used to prepare immunogen. Hapten SDMA-SBAP can be used to prepare a G6PDH conjugate. The immunogen SDMA-M-SH-KLH can be used for elicitation of antibodies. In certain embodiments, in an enzyme-based assay format, antibodies produced can show good modulation with a symmetrically dimethylated arginine analyte. In some embodiments, the immunogen SDMA-M-SH-KLH can be used to successfully raise antibodies, which may provide an indication that such antibodies have potential use in an enzyme-based symmetric dimethylarginine immunoassay as described hereinafter.

Antibodies and Preparation Thereof

Aspects of the present disclosure include antibodies, which specifically bind to symmetrically dimethylated arginine analytes. In some instances, that antibodies specifically bind one or more of asymmetric dimethylarginine, L-arginine, and N-methylarginine. In some embodiments, an antibody of the present disclosure specifically binds to any of the compounds of the present disclosure, including any of the compounds of Formula 1 described elsewhere herein.

The term "antibody" (also used interchangeably with "immunoglobulin") encompasses polyclonal (e.g., rabbit polyclonal) and monoclonal antibody preparations where the antibody may be an antibody or immunoglobulin of any isotype (e.g., IgG (e.g., IgG1, IgG2, IgG3, or IgG4), IgE, IgD, IgA, IgM, etc.), whole antibodies (e.g., antibodies composed of a tetramer which in turn is composed of two dimers of a heavy and light chain polypeptide); single chain antibodies (e.g., scFv); fragments of antibodies (e.g., fragments of whole or single chain antibodies) which retain specific binding to the compound, including, but not limited to single chain Fv (scFv), Fab, (Fab')$_2$, (scFv')$_2$, and diabodies; chimeric antibodies; monoclonal antibodies; human antibodies; and fusion proteins comprising an antigen-binding portion of an antibody and a non-antibody protein. In some embodiments, the antibody is selected from an IgG, Fv, single chain antibody, scFv, Fab, F(ab')2, or Fab'. The antibodies may be further conjugated to other moieties, such as members of specific binding pairs, e.g., biotin (member of biotin-avidin specific binding pair), and the like.

Immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (usually of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 150 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, (1991 and Lefranc et al. IMGT, the international ImMunoGeneTics information System®. Nucl. Acids Res., 2005, 33, D593-D597)). A detailed discussion of the IMGT system, including how the IMGT system was formulated and how it compares to other systems, is provided on the World Wide Web at imgt.cines.fr/textes/IMGTScientificChart/Numbering/IMGTnumberingsTable.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to IMGT, supra, unless otherwise indicated.

An "antibody" thus encompasses a protein having one or more polypeptides that can be genetically encodable, e.g., by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies encompass intact immunoglobulins as well as a number of well characterized fragments which may be genetically encoded or produced by digestion with various peptidases. Thus, for example, pepsin digests an antibody below the disulfide linkages in the hinge region to produce F(ab')$_2$, a dimer of Fab which itself is a light chain joined to VH-CHI by a disulfide bond. The F(ab)'$_2$ may be reduced under mild conditions to break the disulfide linkage in the hinge region thereby converting the (Fab')$_2$ dimer into an Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, scFv, dAb, nanobodies, unibodies, and diabodies. In certain embodiments, an antibody of the present disclosure is selected from an IgG, Fv, single chain antibody, scFv, Fab, F(ab')$_2$, and Fab'.

The phrases "specifically binds", "specific for", "immunoreactive" and "immunoreactivity", and "antigen binding specificity", when referring to an antibody, refer to a binding reaction with an antigen which is highly preferential to the antigen or a fragment thereof, so as to be determinative of the presence of the antigen in the presence of a heterogeneous population of antigens. Thus, under designated immunoassay conditions, the specified antibodies bind to a particular antigen and do not bind in a significant amount to other antigens present in the sample. Specific binding to an antigen under such conditions may require an antibody that is selected for its specificity for a particular antigen. For example, the antibodies may specifically bind to the compound, and do not exhibit comparable binding to other molecules present in a sample.

In some embodiments, an antibody of the present disclosure "specifically binds" to the compound if it binds to or associates with the compound with an affinity or $K_a$ (that is, an equilibrium association constant of a particular binding interaction with units of 1/M) of, for example, greater than or equal to about $10^5$ M$^{-1}$. In certain embodiments, the antibody binds to the compound with a $K_a$ greater than or equal to about $10^6$ M$^{-1}$, $10^7$ M$^{-1}$, $108$ M$^{-1}$, $10^9$ M$^{-1}$, $10^{10}$ M$^{-1}$, $10^{11}$ M$^{-1}$, $10^{12}$ M$^{-1}$, or $10^{13}$ M$^{-1}$. "High affinity" binding refers to binding with a $K_a$ of at least $10^7$ M$^{-1}$, at least $108$ M$^{-1}$, at least $10^9$ M$^{-1}$, at least $10^{10}$ M$^{-1}$, at least $10^{11}$ M$^{-1}$, at least $10^{12}$ M$^{-1}$, at least $10^{13}$ M$^{-1}$, or greater. Alternatively, affinity may be defined as an equilibrium dissociation constant ($K_D$) of a particular binding interaction with units of M (e.g., $10^{-5}$ M to $10^{-13}$ M, or less). In some embodiments, specific binding means the antibody binds to the compound with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$ M, or $10^{-12}$ M or less. The binding affinity of the antibody for the compound can be readily determined using conventional techniques, e.g., by competitive ELISA (enzyme-linked immunosorbent assay), equilibrium dialysis, by using surface plasmon resonance (SPR) technology (e.g., the BIAcore 2000 instrument, using general procedures outlined by the manufacturer); by radioimmunoassay; or the like.

Whether a first antibody "competes with" a second antibody for binding to the compound may be readily determined using competitive binding assays known in the art. Competing antibodies may be identified, for example, via an antibody competition assay. For example, a sample of a first antibody can be bound to a solid support. Then, a sample of a second antibody suspected of being able to compete with such first antibody is then added. One of the two antibodies is labelled. If the labeled antibody and the unlabeled antibody bind to separate and discrete sites on the compound, the labeled antibody will bind to the same level whether or not the suspected competing antibody is present. However, if the sites of interaction are identical or overlapping, the unlabeled antibody will compete, and the amount of labeled antibody bound to the compound will be lowered. If the unlabeled antibody is present in excess, very little, if any, labeled antibody will bind.

For purposes of the present disclosure, competing antibodies are those that decrease the binding of an antibody to the compound by about 50% or more, about 60% or more, about 70% or more, about 80% or more, about 85% or more, about 90% or more, about 95% or more, or about 99% or more. Details of procedures for carrying out such competition assays are well known in the art and can be found, for example, in Harlow and Lane, Antibodies, A Laboratory Manual, Cold Spring Harbor Laboratory Press, Cold Spring Harbor, N.Y., 1988, 567-569, 1988, ISBN 0-87969-314-2. Such assays can be made quantitative by using purified antibodies. A standard curve may be established by titrating one antibody against itself, i.e., the same antibody is used for both the label and the competitor. The capacity of an unlabeled competing antibody to inhibit the binding of the labeled antibody to the plate may be titrated. The results may be plotted, and the concentrations necessary to achieve the desired degree of binding inhibition may be compared.

According to some embodiments, an antibody of the present disclosure competes for binding to the compound of Formula 1 with an antibody comprising:
  a variable heavy chain ($V_H$) polypeptide comprising
    a $V_H$ CDR1 comprising the amino acid sequence GFSLSSY (SEQ ID NO:2),
    a $V_H$ CDR2 comprising the amino acid sequence DIKTGDR (SEQ ID NO:3), and
    a $V_H$ CDR3 comprising the amino acid sequence ARVYVSGNDHYDL (SEQ ID NO:4); and
  a variable light chain ($V_L$) polypeptide comprising
    a $V_L$ CDR1 comprising the amino acid sequence QSISNY (SEQ ID NO:6),
    a $V_L$ CDR2 comprising the amino acid sequence RAS (SEQ ID NO:7), and
    a $V_L$ CDR3 comprising the amino acid sequence QLGYTYSNVENA (SEQ ID NO:8).

In certain embodiments, such an antibody comprises the six CDRs set forth in SEQ ID NO:2, SEQ ID NO:3, SEQ ID NO:4, SEQ ID NO:6, SEQ ID NO:7, and SEQ ID NO:8. According to some embodiments, the antibody comprises: a variable heavy chain ($V_H$) polypeptide comprising an amino acid sequence having 70% or greater, 75% or greater, 80% or greater, 85% or greater, 90% or greater, or 95% or greater identity to the amino acid sequence set forth in SEQ ID NO:1; and a variable light chain ($V_L$) polypeptide comprising an amino acid sequence having 70% or greater, 75% or greater, 80% or greater, 85% or greater, 90% or greater, or 95% or greater identity to the amino acid sequence set forth in SEQ ID NO:5.

According to some embodiments, an antibody of the present disclosure competes for binding to the compound of Formula 1 with an antibody comprising:
  a variable heavy chain ($V_H$) polypeptide comprising
    a $V_H$ CDR1 comprising the amino acid sequence GFSLSSY (SEQ ID NO:2),
    a $V_H$ CDR2 comprising the amino acid sequence DIKTGDR (SEQ ID NO:3), and
    a $V_H$ CDR3 comprising the amino acid sequence ARVYVSGNDHYDL (SEQ ID NO:4); and
  a variable light chain ($V_L$) polypeptide comprising
    a $V_L$ CDR1 comprising the amino acid sequence QSISNY (SEQ ID NO:6),
    a $V_L$ CDR2 comprising the amino acid sequence RAS (SEQ ID NO:7), and
    a $V_L$ CDR3 comprising the amino acid sequence QLGYTYTNVENA (SEQ ID NO:10).

In certain embodiments, such an antibody comprises the six CDRs set forth in SEQ ID NO:2, SEQ ID NO:3, SEQ ID NO:4, SEQ ID NO:6, SEQ ID NO:7, and SEQ ID NO:10. According to some embodiments, the antibody comprises: a variable heavy chain ($V_H$) polypeptide comprising an amino acid sequence having 70% or greater, 75% or greater, 80% or greater, 85% or greater, 90% or greater, or 95% or greater identity to the amino acid sequence set forth in SEQ ID NO: 1; and a variable light chain (V$_L$) polypeptide comprising an amino acid sequence having 70% or greater, 75% or greater, 80% or greater, 85% or greater, 90% or greater, or 95% or greater identity to the amino acid sequence set forth in SEQ ID NO:9.

According to some embodiments, an antibody of the present disclosure competes for binding to the compound of Formula 1 with an antibody comprising:
  a variable heavy chain (V$_H$) polypeptide comprising
    a V$_H$ CDR1 comprising the amino acid sequence GFSF-SSTK (SEQ ID NO:12),
    a V$_H$ CDR2 comprising the amino acid sequence CIGTDT (SEQ ID NO: 13), and
    a V$_H$ CDR3 comprising the amino acid sequence ARSSSTGYYNL (SEQ ID NO: 14); and
  a variable light chain (V$_L$) polypeptide comprising
    a V$_L$ CDR1 comprising the amino acid sequence QSIRSY (SEQ ID NO: 16),
    a V$_L$ CDR2 comprising the amino acid sequence YAS (SEQ ID NO: 17), and
    a V$_L$ CDR3 comprising the amino acid sequence HDYYT-FTDND (SEQ ID NO: 18).

In certain embodiments, such an antibody comprises the six CDRs set forth in SEQ ID NO:12, SEQ ID NO:13, SEQ ID NO:14, SEQ ID NO:16, SEQ ID NO:17, and SEQ ID NO:18. According to some embodiments, the antibody comprises: a variable heavy chain (V$_H$) polypeptide comprising an amino acid sequence having 70% or greater, 75% or greater, 80% or greater, 85% or greater, 90% or greater, or 95% or greater identity to the amino acid sequence set forth in SEQ ID NO: 11; and a variable light chain (V$_L$) polypeptide comprising an amino acid sequence having 70% or greater, 75% or greater, 80% or greater, 85% or greater, 90% or greater, or 95% or greater identity to the amino acid sequence set forth in SEQ ID NO: 15.

According to some embodiments, an antibody of the present disclosure competes for binding to the compound of Formula 1 with an antibody comprising:
  a variable heavy chain (V$_H$) polypeptide comprising
    a V$_H$ CDR1 comprising the amino acid sequence GFSF-SSTK (SEQ ID NO:12);
    a V$_H$ CDR2 comprising the amino acid sequence CIGVG-SRGS (SEQ ID NO:20); and
    a V$_H$ CDR3 comprising the amino acid sequence ARSST-TGYYIL (SEQ ID NO:21); and
  a variable light chain (V$_L$) polypeptide comprising
    a V$_L$ CDR1 comprising the amino acid sequence ESIYSY (SEQ ID NO:23);
    a V$_L$ CDR2 comprising the amino acid sequence KAS (SEQ ID NO:24); and
    a V$_L$ CDR3 comprising the amino acid sequence QNYYT-FTEND (SEQ ID NO:25).

In certain embodiments, such an antibody comprises the six CDRs set forth in SEQ ID NO:12, SEQ ID NO:20, SEQ ID NO:21, SEQ ID NO:23, SEQ ID NO:24, and SEQ ID NO:25. According to some embodiments, the antibody comprises: a variable heavy chain (V$_H$) polypeptide comprising an amino acid sequence having 70% or greater, 75% or greater, 80% or greater, 85% or greater, 90% or greater, or 95% or greater identity to the amino acid sequence set forth in SEQ ID NO:19; and a variable light chain (V$_L$) polypeptide comprising an amino acid sequence having 70% or greater, 75% or greater, 80% or greater, 85% or greater, 90% or greater, or 95% or greater identity to the amino acid sequence set forth in SEQ ID NO:22.

According to some embodiments, an antibody of the present disclosure competes for binding to the compound of Formula 1 with an antibody comprising:
  a variable heavy chain (V$_H$) polypeptide comprising
    a V$_H$ CDR1 comprising the amino acid sequence GFSFWR (SEQ ID NO:27);
    a V$_H$ CDR2 comprising the amino acid sequence CIDG-GNTNR (SEQ ID NO:28); and
    a V$_H$ CDR3 comprising the amino acid sequence ARVR-LGNNDYIDL (SEQ ID NO:29); and
  a variable light chain (V$_L$) polypeptide comprising
    a V$_L$ CDR1 comprising the amino acid sequence QSISNY (SEQ ID NO:6);
    a V$_L$ CDR2 comprising the amino acid sequence RAS (SEQ ID NO:7); and
    a V$_L$ CDR3 comprising the amino acid sequence QQGY-NWDLDGA (SEQ ID NO:31).

In certain embodiments, such an antibody comprises the six CDRs set forth in SEQ ID NO:27, SEQ ID NO:28, SEQ ID NO:29, SEQ ID NO:6, SEQ ID NO:7, and SEQ ID NO:31. According to some embodiments, the antibody comprises: a variable heavy chain (V$_H$) polypeptide comprising an amino acid sequence having 70% or greater, 75% or greater, 80% or greater, 85% or greater, 90% or greater, or 95% or greater identity to the amino acid sequence set forth in SEQ ID NO:26; and a variable light chain (V$_L$) polypeptide comprising an amino acid sequence having 70% or greater, 75% or greater, 80% or greater, 85% or greater, 90% or greater, or 95% or greater identity to the amino acid sequence set forth in SEQ ID NO:30.

The amino acid sequences of the above-referenced variable heavy chain (V$_H$) polypeptides, variable light chain (V$_L$) polypeptides, and CDRs are provided in Table 1 below.

TABLE 1

| | VH, VL, and CDR Amino Acid Sequences |
|---|---|
| 1H4/1K4 V$_H$ (SEQ ID NO: 1) | METGLRWLLLVAVLKGVQCQSVEESGGRLVTPGTPLTLTCTVSGFSLSSY TMGWVRQAPGKGLEWIGDIKTGDRTYYANWAKGRFTISRTSTTVDLKMT SLTTEDTATYFCARVYVSGNDHYDLWGQGTLVTVSS |
| 1H4/1K4 V$_H$CDR1 (SEQ ID NO: 2) | GFSLSSY |
| 1H4/1K4 V$_H$CDR2 (SEQ ID NO: 3) | DIKTGDR |
| 1H4/1K4 V$_H$CDR3 (SEQ ID NO: 4) | ARVYVSGNDHYDL |
| 1H4/1K4 V$_L$ (SEQ ID NO: 5) | MDTRAPTQLLGLLLLWLPGARCAYDMTQTPASVEVAVGGTVTIKCQASQ SISNYLAWYQQKPGQPPKLLIYRASTLASGVPSRFKGSGRGTEFTLTISGVE CADAATYYCQLGYTYSNVENAFGGGTEVVVK |

TABLE 1-continued

VH, VL, and CDR Amino Acid Sequences

| | |
|---|---|
| 1H4/1K4 V$_L$CDR1 (SEQ ID NO: 6) | QSISNY |
| 1H4/1K4 V$_L$CDR2 (SEQ ID NO: 7) | RAS |
| 1H4/1K4 V$_L$ CDR3 (SEQ ID NO: 8) | QLGYTYSNVENA |
| 8H1/8K3 V$_H$ (SEQ ID NO: 1) | METGLRWLLLVAVLKGVQCQSVEESGGRLVTPGTPLTLTCTVSGFSLSSYTMGWVRQAPGKGLEWIGDIKTGDRTYYANWAKGRFTISRTSTTVDLKMTSLTTEDTATYFCARVYVSGNDHYDLWGQGTLVTVSS |
| 8H1/8K3 V$_H$CDR1 (SEQ ID NO: 2) | GFSLSSY |
| 8H1/8K3 V$_H$CDR2 (SEQ ID NO: 3) | DIKTGDR |
| 8H1/8K3 V$_H$CDR3 (SEQ ID NO: 4) | ARVYVSGNDHYDL |
| 8H1/8K3 V$_L$ (SEQ ID NO: 9) | MDTRAPTQLLGLLLLWLPGARCAYDMTQTPASVEVAVGGTVTIKCQASQSISNYLAWYQQKPGQPPKLLIYRASNLASGVSSRFKGSRGTEFTLTISGVECADAATYYCQLGYTYTNVENAFGGGTEVVVK |
| 8H1/8K3 V$_L$CDR1 (SEQ ID NO: 6) | QSISNY |
| 8H1/8K3 VL CDR2 (SEQ ID NO: 7) | RAS |
| 8H1/8K3 V$_L$CDR3 (SEQ ID NO: 10) | QLGYTYTNVENA |
| 1H2/1K4 V$_H$ (SEQ ID NO: 11) | METGLRWLLLVAVLKGVQCQEQLVESGGGLVQSEGSLTLTCTASGFSFSSTKYMCWVRQAPGKRPEWIACIGTDTTYYASWAKGRFTISRTSSTTVTLQMTSLTAADTATYFCARSSTGYYNLWGQGTLVTVSS |
| 1H2/1K4 V$_H$CDR1 (SEQ ID NO: 12) | GFSFSSTK |
| 1H2/1K4 V$_H$CDR2 (SEQ ID NO: 13) | CIGTDT |
| 1H2/1K4 V$_H$CDR3 (SEQ ID NO: 14) | ARSSTGYYNL |
| 1H2/1K4 V$^L$ (SEQ ID NO: 15) | MDTRAPTQLLGLLLLWLPGARCADVVMTQTPASVSEPVGGTVTIKCQASQSIRSYLAWYQQKPGQPPKLLIYYASTLASGVSSRFKGSGSGTEFTLTINGVQCDDAATYYCHDYYTFTDNDFGGGTEVVVK |
| 1H2/1K4 V$_L$CDR1 (SEQ ID NO: 16) | QSIRSY |
| 1H2/1K4 V$_L$CDR2 (SEQ ID NO: 17) | YAS |
| 1H2/1K4 V$_L$CDR3 (SEQ ID NO: 18) | HDYYTFTDND |
| 3H1/3K3 V$_H$ (SEQ ID NO: 19) | METGLRWLLLVAVLKGVQCQEQLVESGGGLVQPEGSLTLTCTASGFSFSSTKYMCWVRQAPGRGPEWVACIGVGSRGSTYYASRAKGRFTISKTSSTTVTLQMTSLTAADTATYFCARSSTTGYYILWGQGTLVTVSS |
| 3H1/3K3 V$_H$CDR1 (SEQ ID NO: 12) | GFSFSSTK |
| 3H1/3K3 V$_H$CDR2 (SEQ ID NO: 20) | CIGVGSRGS |
| 3H1/3K3 V$_H$CDR3 (SEQ ID NO: 21) | ARSSTTGYYIL |
| 3H1/3K3 V$_L$ (SEQ ID NO: 22) | MDTRAPTQLLGLLLLWLPGARCAFEMTQTPSSVSAAVGGTVTIKCQASESIYSYLAWYQQKPGQPPKLLIYKASTLASGVSSRFKGSGSGTEFTLTISGVQCDDAATYYCQNYYTFTENDVGGGTEVVVK |

TABLE 1-continued

| | VH, VL, and CDR Amino Acid Sequences |
|---|---|
| 3H1/3K3 V<sub>L</sub>CDR1 (SEQ ID NO: 23) | ESIYSY |
| 3H1/3K3 V<sub>L</sub>CDR2 (SEQ ID NO: 24) | KAS |
| 3H1/3K3 V<sub>L</sub>CDR3 (SEQ ID NO: 25) | QNYYTFTEND |
| 5H1/5K1 V<sub>H</sub> (SEQ ID NO: 26) | METGPRWLLLVAVLKGVQCQEQLAESGGGLVQPEGSLTLTCTASGFSFW RYMCWVRQAPGKGLEWVACIDGGNTNRLYYASWAKGRFTISKTSSTTV TLHMTSLTVADTATYFSARVRLGNNDYIDLWGQGTLVTVSS |
| 5H1/5K1 V<sub>H</sub>CDR1 (SEQ ID NO: 27) | GFSFWR |
| 5H1/5K1 V<sub>H</sub>CDR2 (SEQ ID NO: 28) | CIDGGNTNR |
| 5H1/5K1 V<sub>H</sub>CDR3 (SEQ ID NO: 29) | ARVRLGNNDYIDL |
| 5H1/5K1 V<sub>L</sub> (SEQ ID NO: 30) | MDTRAPTQLLGLLLLWLPGARCDVVLTQTPASVEAAVGGTVTIKCQASQS ISNYLAWYQQKPGQPPKLLIYRASTLASGVPSRFKGSGSGTQFTLTISDLEC ADAATYYCQQGYNWDLDGAFGGGTEVVVK |
| 5H1/5K1 V<sub>L</sub>CDR1 (SEQ ID NO: 6) | QSISNY |
| 5H1/5K1 V<sub>L</sub>CDR2 (SEQ ID NO: 7) | RAS |
| 5H1/5K1 V<sub>L</sub>CDR3 (SEQ ID NO: 31) | QQGYNWDLDGA |

In certain embodiments, an antibody of the present disclosure further specifically binds to a metabolite of symmetric dimethylarginine. Metabolites of interest include, but are not limited to, symmetric Nα-acetyl-dimethylarginine (Ac-SDMA). According to some embodiments, an antibody of the present disclosure has reactivity of Ac-SDMA of greater than 5%, greater than 10%, greater than 15%, greater than 20%, greater than 25%, greater than 30%, greater than 35%, greater than 40%, greater than 45%, or greater than 50%, of its reactivity for SDMA.

Aspects of the present disclosure further include nucleic acids. In certain embodiments, a nucleic acid of the present disclosure encodes a variable heavy chain ($V_H$) polypeptide, a variable light chain ($V_L$) polypeptide, or both, of any of the antibodies of the present disclosure, including but not limited to a $V_H$ and/or a $V_L$ that includes the CDRs of any of the antibodies set forth in Table 1. Examples of nucleic acids having nucleotide sequences that encode example antibodies of the present disclosure are provided in Table 2 below.

TABLE 2

| | Nucleotide Sequences |
|---|---|
| 1H4/1K4 V<sub>H</sub> (SEQ ID NO: 32) | ATGGAGACTGGGCTGCGCTGGCTTCTCCTGGTCGCTGTGCTCAAAGGTG TCCAGTGTCAGTCGGTGGAGGAGTCCGGGGGTCGCCTGGTCACGCCTG GGACACCCCTGACACTCACCTGCACAGTCTCTGGATTCTCCCTCAGTAG CTATACAATGGGCTGGGTCCGCCAGGCTCCAGGGAAGGGGCTGGAGTG GATCGGAGACATTAAGACTGGTGATAGGACATACTACGCGAACTGGGC AAAAGGCCGATTCACCATCTCCAGAACCTCGACCACGGTGGATCTGAA AATGACCAGTCTGACAACCGAGGACACGGCCACCTATTTCTGTGCCCG AGTGTATGTTAGTGGTAATGATCACTATGACTTGTGGGGCCAGGGCACC CTGGTCACCGTCTCGAGCGGACAGCCGAAA |
| 1H4/1K4 V<sub>L</sub> (SEQ ID NO: 33) | ATGGACACGAGGGCCCCCACTCAGCTGCTGGGGCTCCTGCTGCTCTGGC TCCCAGGTGCCAGATGTGCCTATGATATGACCCAGACTCCAGCCTCTGT GGAGGTAGCTGTGGGAGGCACAGTCACCATCAAGTGCCAGGCCAGTCA GAGTATTAGTAACTACTTAGCCTGGTATCAGCAGAAACCAGGGCAGCC TCCCAAGCTCCTGATCTACAGGGCATCCACTCTGGCATCTGGGGTCCCA TCGCGGTTCAAAGGCAGTGGACGTGGGACAGAGTTCACTCTCACCATC AGCGGCGTGGAGTGTGCCGATGCTGCCACTTACTACTGTCAACTGGGTT ATACTTATAGTAATGTTGAGAATGCTTTCGGCGGAGGGACCGAGGTGG TGGTCAAAGGTGATCCCGTG |
| 8H1/8K3 V<sub>H</sub> (SEQ ID NO: 34) | ATGGAGACCGGGCTGCGCTGGCTTCTCCTGGTCGCTGTGCTCAAAGGTG TCCAGTGTCAGTCGGTGGAGGAGTCCGGGGGTCGCCTGGTCACGCCTG GGACACCCCTGACACTCACCTGCACAGTCTCTGGATTCTCCCTCAGTAG CTATACAATGGGCTGGGTCCGCCAGGCTCCAGGGAAGGGGCTGGAGTG GATCGGAGACATTAAGACTGGTGATAGGACATACTACGCGAACTGGGC |

TABLE 2-continued

Nucleotide Sequences

|  |  |
|---|---|
| | AAAAGGCCGATTCACCATCTCCAGAACCTCGACCACGGTGGATCTGAA<br>AATGACCAGTCTGACAACCGAGGACACGGCCACCTATTTCTGTGCCCG<br>AGTGTATGTTAGTGGTAATGATCACTATGACTTGTGGGGCCAGGGCACC<br>CTGGTCACCGTCTCGAGCGGACAGCCGAAA |
| 8H1/8K3 $V_L$<br>(SEQ ID NO: 35) | ATGGACACGAGGGCCCCCACTCAGCTGCTGGGGCTCCTGCTGCTCTGGC<br>TCCCAGGTGCCAGATGTGCCTATGATATGACCCAGACTCCAGCCTCTGT<br>GGAGGTAGCTGTGGGAGGCACAGTCACCATCAAGTGCCAGGCCAGTCA<br>GAGCATTAGTAACTACTTAGCCTGGTATCAGCAGAAACCAGGGCAGCC<br>TCCCAAGCTCCTGATCTACAGGGCATCCAATCTGGCATCTGGGGTCTCA<br>TCGCGGTTCAAAGGCAGTGGACGTGGGACAGAGTTCACTCTCACCATC<br>AGCGGCGTGGAGTGTGCCGATGCTGCCACTTACTACTGTCAACTGGGTT<br>ATACTTATACTAATGTTGAGAATGCTTTCGGCGGAGGGACCGAGGTGGT<br>GGTCAAAGGTGATCCCGTG |
| 1H2/1K4 $V_H$<br>(SEQ ID NO: 36) | ATGGAGACTGGGCTGCGCTGGCTTCTCCTGGTCGCTGTGCTCAAAGGTG<br>TCCAGTGTCAGGAGCAGCTGGTGGAGTCCGGGGGAGGCCTGGTCCAGT<br>CTGAGGGATCCCTGACACTCACCTGCACAGCTTCTGGATTCTCCTTCAG<br>CAGCACCAAGTACATGTGCTGGGTCCGCCAGGCTCCAGGGAAGAGGCC<br>TGAGTGGATCGCATGCATTGGTACTGATACCACTTACTACGCGAGCTGG<br>GCGAAAGGCCGATTCACCATCTCCAGAACCTCGTCGACCACGGTGACT<br>CTGCAAATGACCAGTCTGACAGCCGCGGACACGGCCACCTATTTCTGTG<br>CGAGAAGTAGTAGTACTGGTTATTATAATTTGTGGGGCCAGGGCACCCT<br>GGTCACCGTCTCGAGCGGACAGCCGAAA |
| 1H2/1K4 $V_L$<br>(SEQ ID NO: 37) | ATGGACACGAGGGCCCCCACTCAGCTGCTGGGGCTCCTGCTGCTCTGGC<br>TCCCAGGTGCCAGATGTGCCGACGTCGTGATGACCCAGACTCCAGCCTC<br>CGTGTCTGAACCTGTGGGAGGCACAGTCACCATCAAGTGCCAGGCCAG<br>TCAGAGCATTCGTAGCTACTTAGCCTGGTATCAGCAGAAACCAGGGCA<br>GCCTCCCAAGCTCCTGATCTATTATGCATCCACTCTGGCATCTGGGGTC<br>TCATCGCGGTTCAAAGGCAGTGGATCTGGGACAGAGTTCACTCTCACCA<br>TCAACGGCGTGCAGTGTGACGATGCTGCCACTTACTACTGTCACGACTA<br>TTATACTTTTACTGATAATGATTTCGGCGGAGGGACCGAGGTGGTGGTC<br>AAAGGTGATCCCGTG |
| 3H1/3K3 $V_H$<br>(SEQ ID NO: 38) | ATGGAGACTGGGCTGCGCTGGCTTCTCCTGGTCGCTGTGCTCAAAGGTG<br>TCCAGTGTCAGGAGCAGCTGGTGGAGTCCGGGGGAGGCCTGGTCCAGC<br>CTGAGGGATCCCTGACACTCACCTGCACAGCTTCTGGATTCTCCTTCAG<br>CAGCACCAAGTACATGTGCTGGGTCCGCCAGGCTCCAGGGAGGGGCC<br>TGAGTGGGTCGCATGTATTGGTGTTGGTAGTCGTGGTAGCACTTACTAC<br>GCGAGCCGGGCGAAAGGCCGATTCACCATCTCCAAAACCTCGTCGACC<br>ACGGTGACTCTGCAAATGACCAGTCTGACAGCCGCGGACACGGCCACC<br>TATTTCTGTGCGAGGAGTAGTACTACTGGTTATTATATTTTATGGGGCC<br>AGGGCACCCTGGTCACCGTCTCGAGCGGACAGCCGAAA |
| 3H1/3K3 $V_L$<br>(SEQ ID NO: 39) | ATGGACACGAGGGCCCCCACTCAGCTGCTGGGGCTCCTGCTGCTCTGGC<br>TCCCAGGTGCCAGGTGTGCATTCGAGATGACCCAGACTCCATCCTCCGT<br>GTCTGCAGCTGTGGGAGGCACAGTCACCATCAAGTGCCAGGCCAGTGA<br>GAGCATTTACAGCTACTTAGCCTGGTATCAGCAGAAACCAGGGCAGCC<br>TCCCAAGCTCCTGATCTACAAGGCATCCACTCTGGCATCTGGGGTCTCA<br>TCGCGGTTCAAAGGAAGTGGATCTGGGACAGAGTTCACTCTCACCATC<br>AGCGGCGTGCAGTGTGACGATGCTGCCACTTACTACTGTCAAAACTATT<br>ATACTTTTACTGAGAATGATGTCGGCGGAGGGACCGAGGTGGTGGTCA<br>AAGGTGATCCCGTG |
| 5H1/5K1 $V_H$<br>(SEQ ID NO: 40) | ATGGAGACTGGGCCGCGCTGGCTTCTCCTGGTCGCTGTGCTCAAAGGTG<br>TCCAGTGTCAGGAGCAGCTGGCGGAGTCCGGGGGAGGCCTGGTCCAGC<br>CTGAGGGATCCCTGACACTCACCTGCACAGCCTCTGGATTCTCCTTCTG<br>GCGCTACATGTGCTGGGTCCGCCAGGCTCCAGGGAAGGGGCTGGAGTG<br>GGTCGCATGTATTGATGGTGGCAATACTAATAGGCTCTATTACGCGAGC<br>TGGGCGAAAGGCCGATTCACCATCTCCAAAACCTCGTCGACCACGGTG<br>ACTCTGCACATGACCAGTCTGACAGTCGCGGACACGGCCACCTATTTCA<br>GTGCGAGAGTTCGGCTTGGTAATAATGATTATATAGACTTGTGGGGCCA<br>GGGCACCCTGGTCACCGTCTCGAGCGGACAGCCGAAA |
| 5H1/5K1 $V_L$<br>(SEQ ID NO: 41) | ATGGACACGAGGGCCCCCACTCAGCTGCTGGGGCTCCTGCTGCTCTGGC<br>TCCCAGGTGCCAGATGTGATGTTGTGCTGACCCAGACTCCAGCCTCCGT<br>GGAGGCAGCTGTGGGAGGCACAGTCACCATCAAGTGCCAGGCCAGTCA<br>GAGCATTAGTAACTACTTAGCCTGGTATCAGCAGAAACCAGGGCAGCC<br>TCCCAAGCTCCTGATCTACAGGGCATCCACTCTGGCATCTGGGGTCCCA<br>TCGCGGTTCAAAGGCAGTGGATCTGGGACACAGTTCACTCTCACCATCA<br>GCGACCTGGAGTGTGCCGATGCTGCCACTTACTACTGTCAACAGGGTTA<br>TAATTGGGATCTTGATGGTGCTTTCGGCGGAGGGACCGAGGTGGTGGTC<br>AAAGGTGATCCCGTG |

Also provided are expression vectors that include any of the nucleic acids of the present disclosure. The expression vectors find use, e.g., for expressing a $V_H$ and/or a $V_L$ of an antibody of the present disclosure in a host cell. The expression of natural or synthetic nucleic acids encoding a $V_H$ and/or a $V_L$ of an antibody of the present disclosure will typically be achieved by operably linking a nucleic acid encoding the $V_H$ and/or $V_L$ to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the $V_H$ and/or $V_L$. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook et al (1989). To obtain high levels of expression of a cloned nucleic acid it is common to construct expression plasmids which typically contain a strong promoter to direct transcription, a ribosome binding site for translational initiation, and a transcription/ translation terminator.

Accordingly, aspects of the present disclosure further include cells, e.g., recombinant host cells. In certain embodiments, provided are cells that include any of the nucleic acids and/or expression vectors of the present disclosure. According to some embodiments, provided are cells that include a first nucleic acid encoding a variable heavy chain ($V_H$) polypeptide of an antibody of the present disclosure, and a second nucleic acid encoding a variable light chain ($V_L$) polypeptide of the antibody. In certain embodiments, provided are cells that include a first expression vector comprising the first nucleic acid, and a second expression vector comprising the second nucleic acid. Cells of the present disclosure may be produced by introducing one or more nucleic acids and/or expression vectors of the present disclosure into host cells via methods known in the art, e.g., electroporation, lipofection, microinjection, or the like.

Also provided are methods of making the antibodies of the present disclosure. In certain embodiments, such methods include culturing a cell (e.g., recombinant host cell) of the present disclosure under conditions suitable for the cell to express the antibody, wherein the antibody is produced. The suitable conditions for culturing the cell such that the antibody is expressed may vary. Such conditions may include culturing the cell in a suitable container (e.g., a cell culture plate or well thereof), in suitable medium (e.g., cell culture medium, such as DMEM, RPMI, MEM, IMDM, DMEM/F-12, or the like) at a suitable temperature (e.g., 32° C.-42° C., such as 37° C.) and pH (e.g., pH 7.0-7.7, such as pH 7.4) in an environment having a suitable percentage of $CO_2$, e.g., 3% to 10%, such as 5%).

Also provided are methods of preparing polyclonal antibodies that specifically bind any of the new immunogens set forth in Formula 1. Antiserum containing antibodies is obtained by well-established techniques involving immunization of an animal, such as rabbits and sheep, with an appropriate immunogen set forth in Formula 1 and obtaining antisera from the blood of the immunized animal after an appropriate waiting period. Reviews are provided by Parker, Radioimmunoassay of Biologically Active Compounds, Prentice-Hall (Englewood Cliffs, N.J., U.S., 1976), Butler, J. Immunol. Meth. 7: 1 24 (1975); Broughton and Strong, Clin. Chem. 22: 726 732 (1976); and Playfair, et al., Br. Med. Bull. 30: 24 31 (1974). The immunization procedures are well established in the art and are set forth in numerous treatises and publications including "The Immunoassay Handbook", 2nd Edition, edited by David Wild (Nature Publishing Group, 2000) and the references cited therein. The degree of the antibody purification required depends on the desired application. For many purposes there is no requirement for purification.

Serum harvested may be tested for the presence of antibodies that specifically bind symmetrically dimethylated arginine analyte using a symmetric dimethylarginine protein conjugate or other symmetric dimethylarginine conjugates in either an ELISA format or homogeneous enzyme immunoassay format. This technique is generally applicable to produce polyclonal antibodies to symmetrically dimethylated arginine analyte as described herein and to assess their utility. The specific antibodies prepared are useful as reagents for immunoassays for the detection or determination (optionally including quantification) of symmetric dimethylarginine.

The following procedure may be employed to prepare monoclonal antibodies, in particular for monoclonal antibodies that specifically bind the immunogens of Formula 1. Monoclonal antibodies may be produced according to the standard techniques of Kohler and Milstein, Nature 265:495 497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3 46 (1981). Samples of an appropriate immunogen preparation are injected into an animal such as a rabbit or mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity. Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody may be harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Kohler and Milstein, supra).

The following procedure may be employed to prepare recombinant monoclonal antibodies, in particular monoclonal antibodies that specifically bind the immunogens of Formula 1. Single B-cell screen, cloning and expression was performed. Peripheral blood mononuclear cells (PBMCs) were isolated from whole blood of rabbit and cultured the same day and plating single B-cells onto 40×96 well plates. The 40×96-well plates were incubated at 37° C./5% $CO_2$ for seven days in B cell culturing media and the supernatants were then screened by indirect ELISA against SDMA-SBAP-BSA antigen to determine antigen-positive wells. Antigen-positive wells were preserved in RNA lysis buffer and stored at −80° C. mRNA was isolated from selected B cell well (SDMA-SBAP-BSA antigen-positive wells) by Dynabeads mRNA DIRECT purification kit (Ambion, catalog #61012). cDNA was synthesized and 2 rounds of PCR performed to prepare the antibody variable region cDNA for cloning. Rabbit IgG heavy and kappa light chain variable region cDNAs were cloned into mammalian expression vectors with a rabbit heavy and a light chain constant region, respectively. Expression constructs were co-transfected into HEK 293 cells and cell culture supernatants assayed by indirect ELISA against SDMA-SBAP-BSA antigen. The antibodies were purified according to standard approaches for antibody purification from supernatants. In general, antibodies can be purified by known techniques such as chromatography, e.g., DEAE chromatography, ABx chromatography, and the like, filtration, and so forth. Antibodies may be screened using any of several techniques, for example using a homogeneous enzyme immunoassay format as illustrated in FIG. 10, and considering such properties as, conjugate inhibition, curve size and cross-reactivity, and so forth.

DNA sequencing was performed for selected positive rabbit monoclonal antibodies. The rabbit IgG heavy chain sequence is approximately 1200 bp and can be sequenced from the 5' ends to obtain a reliable full-length variable sequence. The rabbit kappa light chain is approximately 700 bp and full-length variable sequence can be reliably obtained from sequencing in the 5' direction. All heavy chain and kappa chain variable region sequences were translated. The resulting amino acid sequences of the $V_H$ and $V_L$ of example antibodies are provided in Table 1 above.

Compositions

The present disclosure also provides compositions. According to some embodiments, a composition of the present disclosure includes any of the compounds, antibodies, nucleic acids, expression vectors, and/or cells of the present disclosure.

In certain aspects, a composition of the present disclosure includes any of the compounds, antibodies, nucleic acids, expression vectors, and/or cells of the present disclosure present in a liquid medium. The liquid medium may be an aqueous liquid medium, such as water, a buffered solution, or the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, a protease inhibitor, glycerol, a chelating agent, and the like may be present in such compositions.

In certain embodiments, the compositions of the present disclosure find use as reagents in performing any of the immunoassays of the present disclosure, including any of the homogenous enzyme immunoassays described herein. For example, a composition that includes any of the compounds of Formula 1 of the present disclosure, any of the antibodies of the present disclosure, or both, may be employed to perform such immunoassays. According to some embodiments, the reagents are provided in lyophilized form, e.g., to increase stability, convenience, and/or the like. As just one example, a composition that includes any of the compounds of Formula 1 of the present disclosure, any of the antibodies of the present disclosure, or both, may be provided in the form of lyophilized reagent spheres as described in U.S. Pat. No. 5,413,732, the disclosure of which is incorporated herein by reference in its entirety for all purposes. Briefly, such spheres may be made, e.g., by forming a homogeneous solution of a reagent; measuring uniform drops of the solution (e.g., 2 to 50 μL); dispensing the uniform, measured drops into an unagitated cryogenic liquid (e.g., liquid nitrogen), whereby the drops are frozen; collecting the frozen drops from the cryogenic liquid; and lyophilizing the frozen drops, thereby forming a plurality of lyophilized reagent spheres.

Immunoassays

Aspects of the present disclosure further include methods of using any of the compounds of Formula 1 of the present disclosure and/or any of the antibodies of the present disclosure. In certain embodiments, such compounds and/or antibodies may be used for detecting (including determining an amount of) at least one symmetrically dimethylated arginine analyte in a medium, e.g., a medium that includes a biological sample of interest. For example, according to some embodiments, provided are methods for determining an amount of at least one symmetrically dimethylated arginine analyte in a medium, the methods including combining in a medium a sample suspected of containing at least one symmetrically dimethylated arginine analyte, and any of the antibodies of the present disclosure. Such methods further include determining the presence or absence of a complex comprising the symmetrically dimethylated arginine analyte and the antibody, wherein the presence of the complex indicates the presence of the symmetrically dimethylated arginine analyte in the sample. In certain embodiments, the medium further includes any of the compounds of Formula 1 of the present disclosure. For example, the medium may further include a symmetric dimethylarginine conjugate that has a symmetric dimethylarginine moiety and a detectable label (e.g., enzyme, such as G6PDH).

The sample suspected of containing at least one symmetrically dimethylated arginine analyte may be any sample of interest. In certain embodiments, the sample is whole blood, blood serum, blood plasma, urine, sputum, semen, saliva, ocular lens fluid, cerebral fluid, spinal fluid, amniotic fluid, tissue culture media, or the like, and including dilutions thereof.

The present disclosure provides immunoassay methods for assessing the presence or absence of a symmetrically dimethylated arginine analyte in a sample suspected of containing the analyte. Immunoassays of the present disclosure can be of a variety of formats. The immunoassays may be separation immunoassays (also known as heterogeneous immunoassays) or homogeneous immunoassays. Furthermore, the immunoassays may be qualitative or quantitative. Assays of this disclosure include both sandwich and competition assays. The immunoassays may embody other types of assays that are neither sandwich nor competition assays, as in certain assays involving immunoprecipitation. In certain embodiments, the immunoassay is a homogeneous immunoassay, where the assay reagents and sample are mixed together to form a homogeneous assay mixture.

In certain embodiments, the immunoassay is a homogeneous enzyme immunoassay system used for the analysis of a symmetrically dimethylated arginine analyte in a biological fluid sample. In some instances, the immunoassay is based on competition between the symmetrically dimethylated arginine analyte in the sample and labeled Nα-acylated-SDMA and/or Nα-alkylated-SDMA for antibody binding sites. In some embodiments, the label is a protein, such as an enzyme. For example, the label may be an enzyme the activity of which may be measured spectrophotometrically. In one non-limiting example, an assay of the present disclosure employs Nα-acylated-SDMA and/or Nα-alkylated- SDMA labeled with the enzyme glucose-6-phosphate dehydrogenase (G6PDH) for antibody binding sites. In certain embodiments, enzyme activity decreases upon binding to the antibody, such that the concentration of the symmetrically dimethylated arginine analyte in the sample can be measured in terms of enzyme activity. In some cases, active enzyme converts nicotinamide adenine dinucleotide (NAD$^+$) to NADH, resulting in an absorbance change that is measured spectrophotometrically. In certain instances, endogenous serum G6PDH does not interfere with the immunoassay because the coenzyme NAD$^+$ functions only with the bacterial (*Leuconostoc mesenteroides*) enzyme employed in the assay.

In general, the immunoassays of the present disclosure for detecting the presence (or absence) of a symmetrically dimethylated arginine analyte in a sample can be conducted by adding, to a reaction mixture, (i) a sample suspected of containing a symmetrically dimethylated arginine analyte and (ii) an antibody that specifically binds to a symmetrically dimethylated arginine analyte to form a complex between the antibody and symmetrically dimethylated arginine analyte that may be present in the sample. The method also includes detecting the presence or absence of the complex. The presence (or absence) of the complex may be indicative of the presence (or absence) of symmetrically dimethylated arginine analyte in the sample. Moreover, the amount of complex formed can be assessed to determine the concentration of symmetrically dimethylated arginine analyte present in the sample (e.g., to provide an assessment of serum or tissue concentration of symmetrically dimethylated arginine analyte in a subject from whom the sample was obtained). The presence and/or amount of complex can be assessed directly (e.g., by detecting bound antibody in the complex) or indirectly (e.g., by assessing activity of an enzyme in a symmetric dimethylarginine enzyme conjugate, where when the symmetric dimethylarginine enzyme conjugate is not bound to antibody, a detectable signal is generated, indicating that the symmetrically dimethylated arginine analyte antibody in the reaction mixture has been bound by symmetrically dimethylated arginine analyte from the sample) (see, e.g., FIG. 10).

In general, the immunoassays of the present disclosure entail combining in a medium (e.g., assay medium or assay reaction mixture), the sample with a symmetrically dimethylated arginine analyte antibody under conditions that permit the formation of a stable complex between the analyte in the sample and the antibody.

Assays may be performed in solution or may use a solid (insoluble) support (e.g., polystyrene, nitrocellulose, or beads), using any standard methods (e.g., as described in Current Protocols in Immunology, Coligan et al., ed.; John Wiley & Sons, New York, 1992). Such methods include ELISAs (enzyme-linked immunosorbent assays), IRMAs (immunoradiometric assays), and RIAs (radioimmunoassays). In certain embodiments, the assay is performed in solution, e.g., the assay is performed without the assay reagents attached to or associated with a solid support.

Where the assay is performed in solution, the test sample (and, optionally a control sample) may be incubated with an anti-symmetrically dimethylated arginine analyte antibody for a time period sufficient to allow formation of analyte and affinity reagent complexes. As previously noted, the symmetrically dimethylated arginine analyte antibody may include a detectable label, e.g., radionuclide, fluorescer, or enzyme. The sample may then be treated to separate the symmetrically dimethylated arginine analyte antibody complexes from excess, unreacted symmetrically dimethylated arginine analyte antibody (e.g., by addition of a secondary antibody (e.g., anti-immunoglobulin antiserum)) followed by centrifugation to precipitate the secondary complexes, or by binding to an affinity surface such as a second, unlabeled antibody fixed to a solid substrate such as Sepharose® or a plastic well). Detection of symmetrically dimethylated arginine analyte antibody bound to a symmetrically dimethylated arginine analyte may be achieved in a variety of ways. If necessary, a substrate for the detectable label may be added to the sample.

Where the assay uses a solid support, the support can have a symmetrically dimethylated arginine analyte antibody (or conjugate) bound to a support surface. Binding of the assay reagent may facilitate the stable, wash-resistant binding of symmetrically dimethylated arginine analyte which may be present in the sample (or antibody that is not bound to symmetrically dimethylated arginine analyte from the sample, and is present in the reaction mixture, as in a competitive binding assay) to the solid support via specific binding to the antibody. The insoluble support may be any composition to which antibodies or suitable symmetric dimethylarginine conjugates can be bound, which can be separated from soluble material, and which is otherwise compatible with the overall method of detection of symmetrically dimethylated arginine analyte in a sample.

The surface of such supports may be solid or porous and of any convenient shape. Examples of suitable insoluble supports to which the symmetrically dimethylated arginine analyte antibody or symmetrically dimethylarginine conjugate is bound include beads, e.g., magnetic beads, membranes and microtiter plates. These can be composed of glass, plastic (e.g., polystyrene), polysaccharides, nylon or nitrocellulose.

Assay reagents can include the symmetrically dimethylated arginine analyte antibody as disclosed herein, as well as secondary antibodies, which may be optionally detectably labeled. After binding of an assay reagent to the support, the support may be treated with a blocking agent, which binds to the support in areas not occupied by the assay reagent. Suitable blocking agents include non-interfering proteins such as bovine serum albumin, casein, gelatin, and the like. Alternatively, detergents at non-interfering concentrations, such as Tween, NP40, TX100, and the like may be used. Such blocking treatment may reduce nonspecific binding.

Assays of the present disclosure include both qualitative and quantitative assays. Typical quantitative methods involve mixing an analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte can be used to establish the assay result. Unless otherwise stated, the act of "measuring" or "determining" in this disclosure encompasses both qualitative and quantitative determination.

Immunoassay reagents that find use alone or in combination in the assays described herein include, but are not limited to, a symmetrically dimethylated arginine analyte antibody, a symmetric dimethylarginine conjugate, and a symmetrically dimethylated arginine analyte (e.g., as a control or in competitive binding assays). Immunoassay reagents can be provided in a buffered aqueous solution. Such solutions may include additional components such as surface active additives, organic solvents, defoamers, buffers, surfactants, and anti-microbial agents. Surface active additives can be introduced to maintain hydrophobic or low-solubility compounds in solution, and stabilize components in the solution. Examples include bulking agents such as β-lactoglobulin (BLG) or polyethyleneglycol (PEG); defoamers and surfactants such as Tween-20, Plurafac A38, Triton X-100, Pluronic 25R2, rabbit serum albumin (RSA), bovine serum albumin (BSA), and carbohydrates. Examples of organic solvents can include methanol and other alcohols. Various buffers may be used to maintain the pH of the solution during storage. Illustrative buffers include HEPES, borate, phosphate, carbonate, tris, barbital and the like. Anti-microbial agents also extend the storage life of the immunoassay reagent.

The symmetric dimethylarginine conjugates and/or the symmetrically dimethylated arginine analyte antibodies to be used as reagents in an assay can be insolubilized by attachment to a solid support. This can be, for example, a wall of a vessel containing the reagent, to a particulate, or to a large molecular weight carrier that can be kept in suspension but removable by physicochemical means, such as centrifugation or microfiltration. In some cases, the attachment is through one or more covalent bonds. The attachment need not be covalent, but is at least of sufficient strength and/or permanence to withstand a separation technique (including a wash) that may be part of the assay procedure. In some cases, the solid support may be functionalized to include a reactive group to facilitate attachment of the symmetric dimethylarginine conjugate and/or the symmetrically dimethylated arginine analyte antibody to the solid support. Nonlimiting examples of reactive groups that may be used include —COOH, —NH$_2$, —C(O)H, —SH, and the like. In some embodiments, the symmetric dimethylarginine conjugate and/or the symmetrically dimethylated arginine analyte antibody can be conjugated to a protein carrier and the protein carrier can be conjugated to the solid support, thus indirectly attaching the symmetric dimethylarginine conjugate and/or the symmetrically dimethylated arginine analyte antibody to the solid support. Certain particulate materials include, but are not limited to, agarose, polystyrene, cellulose, polyacrylamide, latex particles, magnetic particles, and fixed red cells. Examples of commercially available matrices include, but are not limited to, Sepharose® (Pharmacia), Poros® resins (Roche Molecular Biochemicals), Actigel Superflow™ resins (Sterogene Bioseparations Inc.), and Dynabeads™ (Dynal Inc.). In certain embodiments, the choice of the solid support may depend on one or more of stability, capacity, accessibility of the coupled antibody, flow rate (or the ability to disperse the resin in the reaction mixture), and ease of separation.

As noted above, immunoassays for detection of a symmetrically dimethylated arginine analyte can be of a variety of formats. In general, the immunoassays involve combining one or more immunoassay reagents (e.g., at least an anti-symmetrically dimethylated arginine analyte antibody) with a test sample (i.e., a sample suspected of containing a symmetrically dimethylated arginine analyte) in a medium (e.g., a reaction mixture or an assay mixture). "Reaction mixture" or "assay mixture" generally refers to the combination of a sample suspected of containing a symmetrically dimethylated arginine analyte and one or more immunoassay reagents as exemplified in the present disclosure to facilitate detection of the presence or absence of a symmetrically dimethylated arginine analyte in the sample, where the detection may be qualitative or quantitative. The reaction mixture is usually an aqueous solution, although the immunoassay reagent(s) may be in solution or immobilized on a support (e.g., a substrate, such as a bead). The reaction mixture can include other components compatible with the immunoassay, e.g., buffers, reagents, and the like.

Immunoassays usually are classified in one of several ways. For example, immunoassays can be classified according to the mode of detection used, i.e., enzyme immunoassays, radio immunoassays, fluorescence polarization immunoassays, chemiluminescence immunoassays, turbidimetric assays, etc. Another grouping method is according to the assay procedure used, i.e., competitive assay formats, sandwich-type assay formats as well as assays based on precipitation or agglutination principles. In certain instances, a further distinction is made depending on whether washing steps are included in the procedure (so-called heterogeneous assays) or whether reaction and detection are performed without a washing step (so-called homogeneous assays). Certain assays are described in more detail below.

Immunoassays may be described as heterogeneous or homogeneous. "Homogeneous immunoassay", as used herein, refers to an assay method where the complex is not separated from unreacted reaction components, but instead the presence of the complex is detected by a property which at least one of the reactants acquires or loses as a result of being incorporated into the complex. Homogeneous assays include systems involving fluorochrome and fluorochrome quenching pairs on different reagents; enzyme and enzyme inhibitor pairs on different reagents; chromophore and chromophore modifier pairs on different reagents; and latex agglutination assays.

A certain homogeneous assay is the quantitative homogeneous enzyme immunoassay in which a symmetric methylarginine is conjugated to an active enzyme. In some embodiments, the conjugation is arranged so that the binding of a symmetrically dimethylated arginine analyte antibody to the symmetric methylarginine conjugate affects enzymatic activity of the conjugate in a qualitative or quantitative fashion. If a sample containing symmetrically dimethylated arginine analyte is premixed with the antibody, the antibody may complex with the symmetrically dimethylated arginine analyte and thus be prevented from binding to the enzyme conjugate. In this way, the activity of the enzyme in the conjugate can be correlated with the amount of symmetrically dimethylated arginine analyte present in the sample.

G6PDH is a certain enzyme useful in such assays. In some embodiments, the G6PDH is a variant of a naturally-occurring G6PDH in which one or more lysine residues are deleted or substituted, or one or more cysteine residues are introduced. For example, *Leuconostoc mesenteroides* G6PDH are dimeric enzymes that have the ability to catalyze the oxidation of D-glucose-6-phosphate to D-glucono-delta-lactone-6-phosphate by utilizing either NAD$^+$ or NADP$^+$. This property of using NAD$^+$ differentiates these enzymes from human G6PDH, which utilizes only NADP$^+$ effectively, and allows *L. mesenteroides*-specific G6PDH activity to be measured in the presence of human G6PDH, as for example in human-derived samples. Two certain genera of bacteria from which to select G6PDH are *Leuconostoc* and *Zymomonas*. Within these genera *L. mesenteroides, L. citreum, L. lactis, L. dextranicum*, and *Z. mobilis* are of interest, where *L. mesenteroides, L. citreum*, and *L. lactis* are specific examples. Another example of a homogeneous assay system is the cloned enzyme donor immunoassay.

Symmetric dimethylarginine derivatives with thiol reactive groups can be prepared as described above, and may be allowed to react with a glucose-6-phosphate dehydrogenase (G6PDH) mutant enzyme to form the respective enzyme conjugates (see, e.g., FIG. 7). The mutant enzyme may be obtained by the procedure described in U.S. Pat. Nos. 6,090,567 and 6,033,890, the disclosures of which are incorporated herein by reference.

In some embodiments, the immunoassay further includes adding a symmetric dimethylarginine conjugate that has a symmetric dimethylarginine moiety and a detectable label to the sample. The presence or absence of symmetrically dimethylated arginine analyte in the sample can be detected by detecting the detectable label. The detectable label may include an enzyme and the detecting may be performed by assaying activity of the enzyme. In certain embodiments, the enzyme is a dehydrogenase, such as G6PDH.

Luminescence oxygen channeling assay (LOCI) is a chemilumenescence homogeneous immunoassay whereby a biotinylated antibody to the analyte binds to streptavidin-coated donor beads and a second antibody to the analyte is directly conjugated to LOCI acceptor beads. In the presence of the analyte, the two beads come into close proximity. The excitation of the donor beads at 680 nm generates singlet oxygen molecules that trigger a series of chemical reactions in the LOCI acceptor beads resulting in a detectable peak of light emission at 615 nm (Ullman, E. F. et al. (1996) Clin. Chem. 42, 1518-1526).

In a separation-based or "heterogeneous" assay, the detecting of a complex of a symmetrically dimethylated arginine analyte antibody and an analyte involves a process where the complex formed is physically separated from either unreacted analyte, unreacted antibody, or both.

In a heterogeneous immunoassay, a complex of an antibody and a symmetrically dimethylated arginine analyte may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled derivative or labeled antibody to facilitate detection or quantitation of the complex. Suitable labels include radioisotopes such as $^{125}$I, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

Assays of the present disclosure include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with a derivative of the analyte for binding to another reagent, such as an antibody. An example of a competition assay using EMIT® is described in U.S. Pat. No. 3,817,837.

The compounds and methods of the presently disclosed embodiments also encompass the use of these materials in lateral flow chromatography technologies. Lateral flow chromatography involves a membrane strip which includes a detection device, such as a non-isotopic signal generating moiety, for symmetrically dimethylated arginine analyte. A sample from a patient may then be applied to the membrane strip. The sample may interact with the detection device, producing a result. The results can signify several things, including the absence of the symmetrically dimethylated arginine analyte in the sample, the presence of the symmetrically dimethylated arginine analyte in the sample, and/or the concentration of the symmetrically dimethylated arginine analyte in the sample.

Certain embodiments provide a method of qualitatively determining the presence or absence of a symmetrically dimethylated arginine analyte in a sample, through the use of lateral flow chromatography. In certain embodiments, the basic design of the qualitative lateral flow device is as follows: 1) The sample pad is where the sample is applied. The sample pad is treated with chemicals such as buffers or salts, which, when re-dissolved, optimize the chemistry of the sample for reaction with the conjugate, test, and control reagents; 2) Conjugate release pad is typically a polyester or glass fiber material that is treated with a conjugate reagent such as an antibody colloidal gold conjugate. A typical process for treating a conjugate pad is to use impregnation followed by drying. In use, the liquid sample added to the test will re-dissolve the conjugate so that it will flow into the membrane; 3) The membrane substrate is usually made of nitrocellulose or a similar material whereby antibody capture components are immobilized; 4) A wicking pad is used in tests where blood plasma must be separated from whole blood. An impregnation process is usually used to treat this pad with reagents intended to condition the sample and promote cell separation; 5) The absorbent pad acts as a reservoir for collecting fluids that have flowed through the device; and 6) The above layers and membrane system are laminated onto a plastic backing with adhesive material which serves as a structural member.

Certain embodiments provide a method of qualitatively determining the presence of a symmetrically dimethylated arginine analyte in a sample, through the use of lateral flow chromatography. In these embodiments, the membrane strip includes a sample pad, which is a conjugate release pad that has an antibody that is specific for the symmetrically dimethylated arginine analyte. This antibody may be conjugated to a non-isotopic signal-generating moiety, such as a colloidal gold particle. Other detection moieties useful in a lateral flow chromatography environment include dyes, colored latex particles, fluorescently labeled latex particles, non-isotopic signal generating moieties, etc. In some instances, the membrane strip further includes a capture line, in which the symmetrically dimethylated arginine analyte antigen or symmetrically dimethylarginine conjugate is immobilized on the strip. In some embodiments, this immobilization is through covalent attachment to the membrane strip, optionally through a linking group. In other embodiments, the immobilization is through non-covalent attachment to the membrane strip. In still other embodiments, the immobile symmetrically dimethylated arginine analyte in the capture line is attached to a reactive partner, such as an immunogenic carrier like BSA.

Sample from a patient may be applied to the sample pad, where it can combine with the antibody in the conjugate release pad, thus forming a solution. This solution may then migrate chromatographically by capillary action across the membrane. When symmetrically dimethylated arginine analyte is present in the sample, a symmetrically dimethylated arginine analyte antibody complex may be formed, which migrates across the membrane by capillary action. When the solution reaches the capture line, the symmetrically dimethylated arginine analyte antibody complex may compete with the immobile symmetrically dimethylated arginine analyte for the limited binding sites of the antibody. When a sufficient concentration of symmetrically dimethylated arginine analyte is present in the sample, it may fill the limited antibody binding sites. In certain instances, this will prevent the formation of a colored antibody-immobile symmetrically dimethylated arginine analyte complex in the capture line. Therefore, absence of color in the capture line indicates the presence of symmetrically dimethylated arginine analyte in the sample.

In the absence of symmetrically dimethylated arginine analyte in the sample, a colored antibody-immobile symmetrically dimethylated arginine analyte complex may form once the solution reaches the capture line of the membrane strip. In some instances, the formation of this complex in the capture line is evidence of the absence of symmetrically dimethylated arginine analyte in the sample.

Certain embodiments provide a method of quantitatively determining the amount of a symmetrically dimethylated arginine analyte in a sample, through the use of lateral flow chromatography. This technology is further described in U.S. Pat. Nos. 4,391,904; 4,435,504; 4,959,324; 5,264,180; 5,340,539; and 5,416,000, the disclosures of which are incorporated herein by reference. In some embodiments, the antibody may be immobilized along the entire length of the membrane strip. In general, if the membrane strip is made from paper, the antibody may be covalently bound to the membrane strip. If the membrane strip is made from nitrocellulose, then the antibody can be non-covalently attached to the membrane strip through, for example, hydrophobic and electrostatic interactions. The membrane strip may include a conjugate release pad that includes the symmetrically dimethylated arginine analyte attached to a detector moiety. In certain embodiments, the detector moiety is an enzyme, such as horseradish peroxidase (HRP).

In certain embodiments, sample from a patient is applied to the membrane strip, where it can combine with the symmetrically dimethylated arginine analyte/detector molecule in the conjugate release pad, thus forming a solution. This solution may then be allowed to migrate chromatographically by capillary action across the membrane. When symmetrically dimethylated arginine analyte is present in the sample, both the sample symmetrically dimethylated arginine analyte and the symmetrically dimethylated arginine analyte/detector molecule compete for the limited number of binding sites of the antibody. When a sufficient concentration of symmetrically dimethylated arginine analyte is present in the sample, it may fill the limited antibody binding sites. In some instances, this forces the symmetrically dimethylated arginine analyte/detector molecule to continue to migrate in the membrane strip. The shorter the distance of migration of the symmetrically dimethylated arginine analyte/detector molecule in the membrane strip, the lower the concentration of symmetrically dimethylated arginine analyte in the sample, and vice versa. When the symmetrically dimethylated arginine analyte/detector molecule includes an enzyme, the length of migration of the symmetrically dimethylated arginine analyte/detector molecule can be detected by applying an enzyme substrate to the membrane strip. Detection of the product of the enzyme reaction may then be utilized to determine the concentration of the symmetrically dimethylated arginine analyte in the sample. In certain embodiments, the enzyme's color producing substrate such as a modified N,N-dimethylaniline is immobilized to the membrane strip and 3-methyl-2-benzothiazolinone hydrazone is passively applied to the membrane, thus alleviating the need for a separate reagent to visualize the color producing reaction.

Fluorescence polarization immunoassay (FPIA) technology is based upon competitive binding. FPIA technology is described in, for example, U.S. Pat. Nos. 4,593,089, 4,492,762, 4,668,640, and 4,751,190, the disclosures of which are incorporated herein by reference.

The FPIA technology can be used to identify the presence of symmetrically dimethylated arginine analyte and can be used in assays that quantify the amount of symmetrically dimethylated arginine analyte in a sample. In part, the rotational properties of molecules in solution allow for the degree of polarization to be directly proportional to the size of the molecule. Accordingly, polarization may increase as molecular size increases. That is, when linearly polarized light is used to excite a fluorescent-labeled or other luminescent-labeled symmetrically dimethylated arginine analyte thereof, which is small and rotates rapidly in solution, the emitted light may be significantly depolarized. When the fluorescent-labeled symmetrically dimethylated arginine analyte interacts with or is bound to an antibody, the rotation may be slowed and the emitted light may be highly polarized. In some cases, this is because the antibody significantly and measurably increases the size of the complex. Also, increasing the amount of unlabeled symmetrically dimethylated arginine analyte in the sample can result in decreased binding of the fluorescent-labeled symmetrically dimethylated arginine analyte by the symmetrically dimethylated arginine analyte antibody, and thereby decrease the polarization of light emitted from sample. The quantitative relationship between polarization and concentration of the unlabeled symmetrically dimethylated arginine analyte in the sample can be established by measuring the polarization values of calibrations with known concentrations of symmetrically dimethylated arginine analyte. Thus, FPIA can be used to identify the presence and concentration of symmetrically dimethylated arginine analyte in a sample.

Homogeneous microparticles immunoassay technology, which can be referred to as immunoturbidimetric assays, is based on the agglutination of particles and compounds in solution. When particles and/or chemical compounds agglutinate, particle sizes can increase and increase the turbidity of a solution. Accordingly, symmetrically dimethylated arginine analyte antibodies can be used with microparticles in order to assess the presence, and optionally the amount, of symmetrically dimethylated arginine analyte in a sample. Homogeneous microparticles immunoassay may be useful because the immunoassays can be performed on blood, blood hemolysate, serum, plasma, tissue, and/or other samples. Homogeneous microparticles immunoassay assays can be configured to be performed with symmetrically dimethylated arginine analyte and loaded onto a microparticle, or with a symmetrically dimethylated arginine analyte antibody loaded onto a microparticle. Homogeneous microparticles immunoassay or immunoturbidimetric assays find use for measuring agglutination of substances in a sample. Immunoturbidimetric assay technologies are described in, e.g., U.S. Pat. Nos. 5,571,728, 4,847,209, 6,514,770, and 6,248,597, the disclosures of which are incorporated herein by reference. Such assays involve light attenuation, nephelometric, or turbidimetric methods.

Cloned Enzyme Donor Immunoassays ("CEDIA®", ThermoFisher), as are based upon the competition of symmetrically dimethylated arginine analyte in the biological sample with a symmetric dimethylarginine conjugate containing an inactive genetically engineered enzyme-donor ("ED") fragment such as from β-D-galactoside galactohydrolase or β-galactosidase ("β-gal") from *E. coli*, for binding to an antibody capable of binding symmetrically dimethylated arginine analyte. If symmetrically dimethylated arginine analyte is present in the sample it may bind to the antibody, leaving the ED portion of the ED-derivative conjugate free to restore enzyme activity of β-D-galactoside galactohydrolase or B-gal in the reaction mixture so as to be capable of association with enzyme acceptor ("EA") fragments. The active enzyme, which includes the ED and EA, may then be capable of producing a quantifiable reaction product when exposed to an appropriate substrate. An example of a substrate is chlorophenol red-β-D-galactopyranoside ("CPRG"), which can be cleaved by the active enzyme into galactose and CPR, where CPR is measured by absorbency at about wavelength 570 nm. If symmetrically dimethylated arginine analyte is not present in the sample, the antibody may bind to the ED-derivative conjugate, thereby inhibiting association of the ED fragments with the EA fragments and inhibiting restoration of enzyme activity. The amount of reaction product and resultant absorbance change are proportional to the amount of symmetrically dimethylated arginine analyte in the sample.

A competitive assay using chemiluminescent microparticle immunoassay ("CMIA") technology can also be used to assess whether or not symmetrically dimethylated arginine analyte is present in a sample. Various types of CMIA technologies may be used for determining the presence and/or amount of an analyte in a sample. CMIA assays can include the use of symmetrically dimethylated arginine analyte antibodies, which are capable of binding to symmetrically dimethylated arginine analyte, which are coupled to particles, such as magnetic particles or particles suitable for separation by filtration, sedimentation, and/or other means. Additionally, a tracer, which can include a symmetric dimethylarginine or derivative linked to a suitable chemiluminescent moiety, can be used to compete with free symmetrically dimethylated arginine analyte in the patient's sample for the limited amount of symmetrically dimethylated arginine analyte antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free analyte in the patient's sample and concentration is determined by constructing a standard curve using known values of the analyte.

According to some embodiments, provided is a homogenous enzyme immunoassay for the analysis of SDMA in biological fluids (e.g., whole blood, blood serum, blood plasma, urine, sputum, semen, saliva, ocular lens fluid, cerebral fluid, spinal fluid, amniotic fluid, tissue culture media, or the like, and including dilutions thereof). The assay is based on competition between SDMA present in the biological fluid and Nα-acylated-SDMA or Nα-alkylated-SDMA labeled with an enzyme (e.g., glucose-6-phosphate dehydrogenase (G6PDH)) for antibody binding sites. Enzyme activity decreases upon binding to the antibody, so the SDMA concentration in the biological fluid can be measured in terms of enzyme activity. For example, active G6PDH converts nicotinamide adenine dinucleotide (NAD$^+$) to NADH, resulting in an absorbance change that may be measured spectrophotometrically. A bacterial (*Leuconostoc mesenteroides*) enzyme may be employed in the assay so that endogenous serum G6PDH does not interfere because the coenzyme NAD$^+$ functions only with the bacterial enzyme.

In certain embodiments, in an immunoassay of the present disclosure, including in any of the homogenous enzyme immunoassays described herein, one or more reagents are provided in lyophilized form. As just one example, a composition that includes any of the compounds of Formula 1 of the present disclosure, any of the antibodies of the present disclosure, or both, may be provided in the form of lyophilized reagent spheres (or "beads") as described in U.S. Pat. No. 5,413,732, the disclosure of which is incorporated herein by reference in its entirety for all purposes. Briefly, such spheres may be made, e.g., by forming a homogeneous solution of a reagent; measuring uniform drops of the solution (e.g., 2 to 50 μL); dispensing the uniform, measured drops into an unagitated cryogenic liquid (e.g., liquid nitrogen), whereby the drops are frozen; collecting the frozen drops from the cryogenic liquid; and lyophilizing the frozen drops, thereby forming a plurality of lyophilized reagent spheres.

According to some embodiments, e.g., including embodiments in which one or more reagents are provided in lyophilized form, a centrifugal analyzer that includes a microfluidic rotor (or "disc") is employed in an immunoassay of the present disclosure. For example, an immunoassay of the present disclosure may employ an analyzer that includes a centrifugal rotor for separating plasma from whole blood that includes a plurality of internal chambers and passages for combining blood plasma or serum with one or more reagents (e.g., lyophilized spheres as described above) and distributing the plasma or serum to a plurality of individual test wells. The chambers and passages necessary for separating the whole blood into plasma are located radially outward from metering chambers that deliver precisely measured volumes of blood and/or diluent to a separation chamber. The separation chamber includes a radially-outward cell trap. Spinning of the rotor causes the cellular components of the whole blood to be sequestered in the cell trap. The separated plasma is then delivered to a plurality of test wells or cuvettes. The above separation and aliquoting steps typically occur as a result of centrifugal force generated by the spinning rotor. The lyophilized reagent spheres described above in combination with the rotors described above are particularly suitable for analyzing blood plasma or diluted blood plasma. They are also useful with a wide variety of other biological fluids, such as urine, sputum, semen, saliva, ocular lens fluid, cerebral fluid, spinal fluid, amniotic fluid, and tissue culture media, as well as food and industrial chemicals, and the like. Details regarding such centrifugal analyzers that include a microfluidic rotor may be found, e.g., in U.S. Pat. Nos. 5,061,381, 5,173,193; 5,122,284 and 5,186,844, the disclosures of which are incorporated herein in their entireties for all purposes.

In some embodiments, the immunoassay employs a centrifugal analyzer that includes a microfluidic rotor comprising siphons for delivering a premeasured volume of liquid (e.g., a biological sample such as whole blood, blood serum, or blood plasma) between a first and a second chamber in the rotor. The siphons may include an elbow that is radially inward of the radially most inward point of the fluid in the first chamber. As the rotor is spinning, the fluid does not flow past the elbow. Once the rotor stops, capillary forces "prime" the siphon by pulling fluid just around the elbow. When the rotor is restarted, centrifugal force draws the remaining fluid out of the metering chamber into the receiving chamber until the level of the fluid in the metering chamber is at the same radial distance as the outlet of the siphon. The siphons may be designed such that the inlet of the siphon on the first chamber is radially outward of the siphon outlet on the second chamber. The positioning of the inlets and outlets of the siphons provides certain advantages. For example, the inlet of the siphon may always be positioned radially outward of the final position of the meniscus of the fluid in the first chamber, after fluid has been transferred to the second chamber. Thus, inaccuracy in measurement associated with different shaped menisci in different fluids is minimized since the meniscus is minimized. In addition, as will be appreciated by one of skill in the art, all siphons are semi-stable because the train of fluid in a siphon is stable but easily broken if the rotor is perturbed. When the train of fluid is broken, under centrifugal force, the fluid contained in the siphon will flow to the radially most outward point. In previous siphons, this point is the siphon outlet. Thus, the potential exists for the delivery of unmetered volumes of fluid to the receiving chamber. In the siphons described herein, the radially most outward point in the siphon is the siphon inlet. In this design, the problem of delivering unmetered volumes of fluid is avoided because the fluid flows back into the first chamber when the train of fluid is broken. Further details regarding analyzers that include a centrifugal rotor comprising siphons for delivering premeasured volumes of liquid, which may be employed in any of the methods/immunoassays of the present disclosure, may be found in U.S. Pat. No. 7,998,411, the disclosure of which is incorporated herein by reference in its entirety for all purposes.

The symmetric dimethylarginine derivatives, conjugates, antibodies, immunogens, and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the symmetric dimethylarginine derivatives, conjugates, antibodies, and immunogens, such assays can also be modified. As such, various modifications of steps or acts for performing such immunoassays can be made within the scope of the embodiments described herein. Additional information related to assay format are described, among other places, in David Wild (The Immunoassay Handbook, 4th Edition Published Date: 31 Jan. 2013, Elsevier Science).

Kits

Aspects of the present disclosure further include kits. In some embodiments, the kits find use in determining an amount of at least one symmetrically dimethylated arginine analyte in a sample. Such kits may include any of the compounds of Formula 1 of the present disclosure, any of the antibodies of the present disclosure, or both.

In certain embodiments, provided are kits for determining an amount of at least one symmetrically dimethylated arginine analyte in a sample, such kits including any of the antibodies of the present disclosure, and instructions for using the antibody to determine an amount of at least one symmetrically dimethylated arginine analyte in a sample. According to some embodiments, the antibody specifically binds to a metabolite of symmetric dimethylarginine (non-limiting examples of which include symmetric Nα-acetyl-dimethylarginine (Ac-SDMA)), and the kit may further include instructions for determining an amount of the metabolite of symmetric dimethylarginine. In certain embodiments, the kits that include an antibody of the present disclosure further include any of the compounds of Formula 1 of the present disclosure. In some embodiments, the compound is one where Z is a label, such as an enzyme, e.g., glucose-6-phosphate dehydrogenase (G6PDH).

Also provided are kits for determining an amount of at least one symmetrically dimethylated arginine analyte in a sample, the kits including any of the compounds of Formula 1 of the present disclosure, and instructions for using the compound to determine an amount of at least one symmetrically dimethylated arginine analyte in a sample. In certain aspects, the compound is one where Z is a label, such as an enzyme, e.g., glucose-6-phosphate dehydrogenase (G6PDH). Such kits may further include any of the antibodies of the present disclosure. According to some embodiments, the antibody specifically binds to a metabolite of symmetric dimethylarginine (non-limiting examples of which include symmetric Nα-acetyl-dimethylarginine (Ac-SDMA)), and the kit may further include instructions for determining an amount of the metabolite of symmetric dimethylarginine.

According to some embodiments, the kits of the present disclosure are useful for conveniently performing an assay for the determination of a symmetrically dimethylated arginine analyte in a sample, such as, for example, symmetric dimethylarginine and its analog, symmetric Nα-acetyl-dimethylarginine. The kit may include: (a) an antibody raised that specifically binds to symmetric dimethylarginine and a compound of Formula 1 described herein (e.g., a symmetric dimethylarginine conjugate); and (b) instructions for determining the amount of the symmetrically dimethylated arginine analyte in the sample. In some embodiments, the kit also includes a conjugate of a compound of Formula 1, where the conjugate includes a label (e.g., a detectable label, such as G6PDH). In certain instances, the kit also includes ancillary reagents for determining the analyte. The antibody of the kit may be an antibody raised against a compound of Formula 1 described herein.

To enhance the versatility of the immunoassay, the kit reagents can be provided in packaged combination, in the same or separate containers, in liquid or lyophilized form so that the ratio of the reagents provides for substantial optimization of the method and assay. In certain embodiments, the kits include an antibody of the present disclosure, a compound of the present disclosure, or both, provided as lyophilized reagent spheres as described in U.S. Pat. No. 5,413,732, the disclosure of which is incorporated herein by reference in its entirety for all purposes. The reagents provided in the kits may each be in separate containers or various reagents can be combined in one or more containers, e.g., depending on the cross-reactivity and stability of the reagents. In some embodiments, the compound of Formula 1 described herein (e.g., a symmetric dimethylarginine conjugate) is present in lyophilized form. In some embodiments, the antibody is present in lyophilized form. For example, the compound of Formula 1 can be present in a first lyophilized composition (which may further include one or more excipients, buffers, stabilizers, etc.), and the antibody can be present in a second lyophilized composition (which may further include an enzyme substrate and one or more excipients, buffers, stabilizers, etc.). The first lyophilized composition and the second lyophilized composition may be provided in a single kit, such as for example in a packaging or container for single use.

The kit can further include other separately packaged reagents for conducting an assay such as ancillary reagents such as an ancillary enzyme substrate, and so forth. The relative amounts of the various reagents in the kits can be varied widely to provide for concentrations of the reagents that substantially optimize the reactions that need to occur when performing a method/immunoassay (e.g., homogenous enzyme immunoassay) and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The description of certain exemplary embodiments of kits uses the language "and/or," which means that the kit may or may not contain each item mentioned. This language is used for the sake of brevity. In general, an immunoassay kit will include at least one antibody for an immunogen of an analyte, e.g., symmetric dimethylarginine, and at least one enzyme conjugate (e.g., label conjugate) that corresponds to that analyte, e.g., an enzyme conjugate of a derivative of symmetric dimethylarginine.

In certain embodiments, a kit is provided for an assay for the analyte symmetric dimethylarginine and/or metabolites of symmetric dimethylarginine. The kit may include, in packaged combination: (i) an antibody raised against a compound of Formula 1; and (ii) a conjugate of a derivative of the analyte. Another embodiment of the presently disclosure is a kit for an assay for the analyte symmetric dimethylarginine and/or metabolites of symmetric dimethylarginine that includes, in packaged combination: (i) an antibody raised against a derivative of the analyte; and (ii) a conjugate of a hapten of the analyte, where the hapten is a compound of Formula 1.

The compounds, methods and kits of the present disclosure find use in routine monitoring of symmetrical dimethylarginine by immunoassays. In certain embodiments, these immunoassays provide simple automated tests adapted to standard laboratory equipment with a quick turn-around time. As described herein, in order to provide such immunoassays, antibodies to a symmetrical dimethylated arginine analyte are produced. The derivatives and immunogens are designed to impart, through the corresponding antibodies, specific reactivity to symmetrical dimethylarginine.

The instructions included in the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

In relation to the compounds and conjugates and immunogens, the following abbreviations are used: DCM is dichloromethane; DMF is N,N-dimethylformamide; EDTA is ethylenediaminetetraacetic acid; KLH is keyhole limpet hemocyanin; SATA is N-succinimidyl S-acetylthioacetate; TFA is trifluoroacetic acid; EDCI is 1-ethyl-3(3-dimethylaminopropyl)carbodiimidehydrochloride; NHS is N-hydroxysuccinimide; DTT is dithioerythritol; G6PDH is Glucose-6-Phosphate Dehydrogenase; EtOAc is Ethyl acetate; BSA is bovine serum albumin; DMO is Dess-Martin periodinane; MeCn is Acetonitrile; EA is ethyl acetate; t-Boc is tert-butyloxycarbonyl protecting group; TLC is thin layer chromatography; MeOH is methanol; AcOH is acetic acid; PBST is phosphate buffered saline with Tween-20; TMB is 3,3',5,5'-tetramethylbenzidine; PBMC is peripheral blood mononuclear cell.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Preparation of SDMA-M Hapten

Step 1.

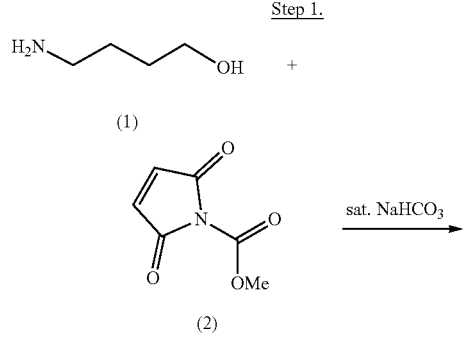

To a solution of (1) (534 mg, 6.0 mmol, 1.0 equiv.) in saturated NaHCO₃ (12 mL) was added (2) (930 g, 6.0 mmol, 1.0 equiv.) in small portions maintaining the temperature at 0° C. Upon completion of addition, the resulting solution was stirred at 0° C. for 1.5 hours. LC-MS showed all starting material was converted to target material. The stirred reaction mixture was allowed to warm to room temperature and extracted with EtOAc. The crude product was purified on silica gel column chromatography (eluting with Petroleum ether/Ethyl acetate=1/1, v/v) to give (3) (0.91 g, 91% yield) as clear oil. The structure was confirmed by ¹H NMR.

Step 2.

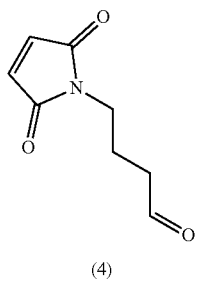

-continued (4)

A mixture of (3) (0.9 g, 5.3 mmol, 1.0 equiv.), Dess-Martin periodinane reagent (4.5 g, 10.6 mmol, 2.0 equiv.) and NaHCO₃ (7.9 g, 94.3 mmol, 18 equiv.) in DCM (40 mL) was stirred at 25° C. for 3 hours. TLC showed most starting material transformed to target material. The reaction mixture was filtered and the resulting filtrate was concentrated under vacuum. The crude product was purified by silica gel column chromatography (Petroleum Ether/Ethyl Acetate=1/1, v/v) to give 0330-04 (0.35 g, 40% yield) as clear oil. The product (4) was extremely sensitive to air, and was immediately used for the next step. The structure was confirmed by LC-MS.

Step 3.

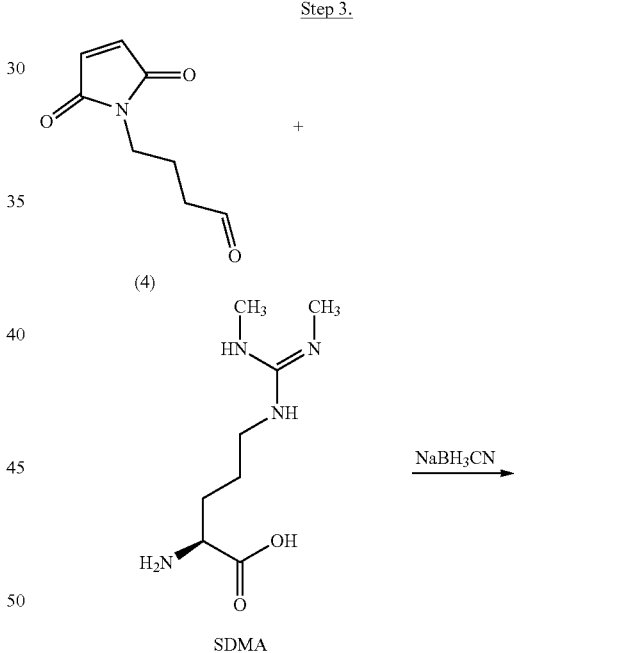

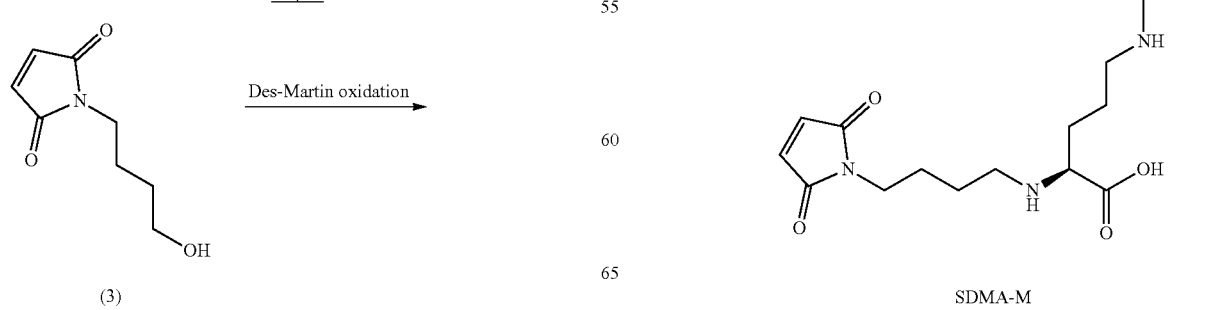

SDMA-M

To a solution of (4) (668 mg, 4 mmol, 2.0 equiv.) and symmetric dimethylarginine (SDMA) (404 mg, 2 mmol, 1.0 equiv.) in MeOH was added AcOH (200 µL) and NaBH₃CN (150 mg, 2.4 mmol, 1.2 equiv.). The resulting mixture was stirred at room temperature for 3 hours. LC-MS showed most starting material transformed to target material. The reaction was quenched with water and immediately purified by Biotage reverse phase chromatography to give SDMA-M (326 mg, 35% yield, as its TFA salt) as clear oil. The structure was confirmed by ¹H NMR. ¹H NMR (400 MHz, D₂O): δ 6.81 (s, 2H), 3.97 (M, 1H), 3.51 (m, 2H), 3.21 (m, 2H), 3.08 (m, 2H), 2.78 (s, 6H), 1.98 (m, 2H), 1.64 (m, 6H). (see FIG. 5).

Example 2

Preparation SDMA-SBAP Hapten

Step 1.

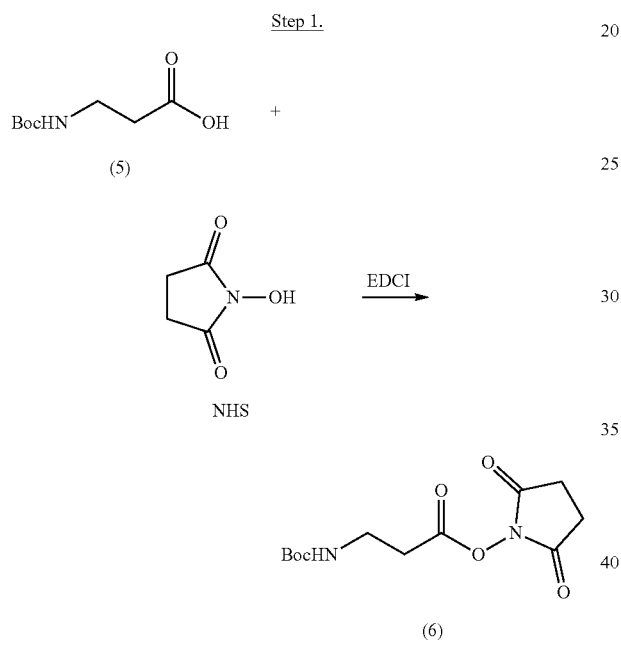

To a solution of (5) (1.4 g, 7.2 mmol, 1.0 equiv.), and N-hydroxysuccinimide (NHS) (Ig, 8.7 mmol, 1.2 equiv.) in DMF (18 mL) was added EDCI (2.78 g, 14.5 mmol, 2.0 equiv.). The resulting mixture was stirred at RT for 12 hours. LC-MS showed all the starting material transformed to target material. The solution was poured into H₂O (100 mL) and extracted with EA (100 mL). The organic phase was washed with H₂O and saturated brine. The organic solvent was removed under reduced pressure and dried in vacuum to give desired product (6) (2.0 g 95.2% yield). The structure was confirmed by ¹H NMR.

Step 2.

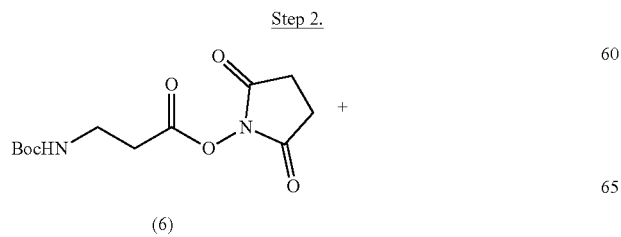

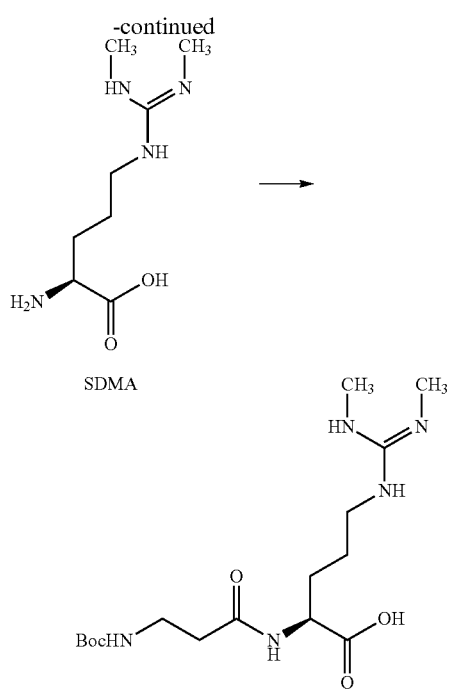

To the solution of symmetric dimethylarginine (SDMA) (400 mg, 2.0 mmol, 1.0 equiv.) in DMF (5 mL) was added (6) (630 mg, 2.2 mmol, 1.1 equiv.). The reaction mixture was stirred at 60° C. for 12 hours. LC-MS showed all the starting material transformed to target material. Solvent was removed under vacuum. The crude product was dissolved in MeCN and water (7.5 mL, 1/1, v/v) and then purified using Biotage reverse phase chromatography (standard method) to give the pure product (7) (650 mg, salt of TFA, 66.7% yield) as a clear oil. The structure was confirmed by ¹H NMR.

Step 3.

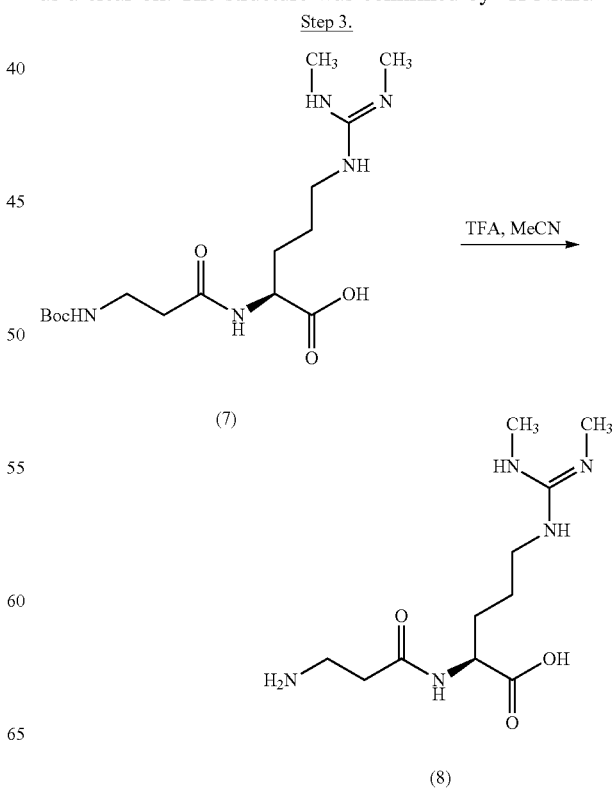

To the solution of (7) (650 mg, 1.33 mmol, 1.0 equiv.) in MeCN (10 mL) was added TFA (4 mL). The reaction mixture was stirred at RT for 30 min. LC-MS showed all the starting material transformed to target material (8). Solvent was removed under reduced pressure and dried in vacuum to give desired product in quantitative yield (as a TFA salt). The structure was confirmed by LC-MS.

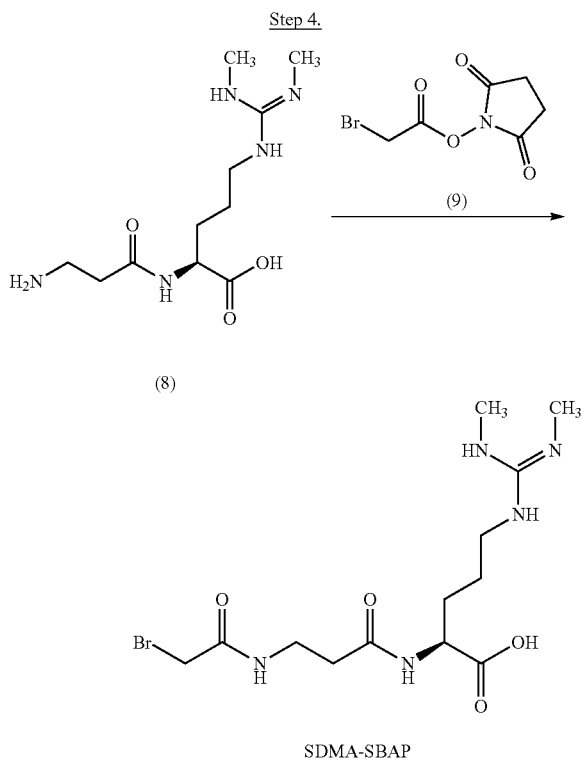

Figure 6:
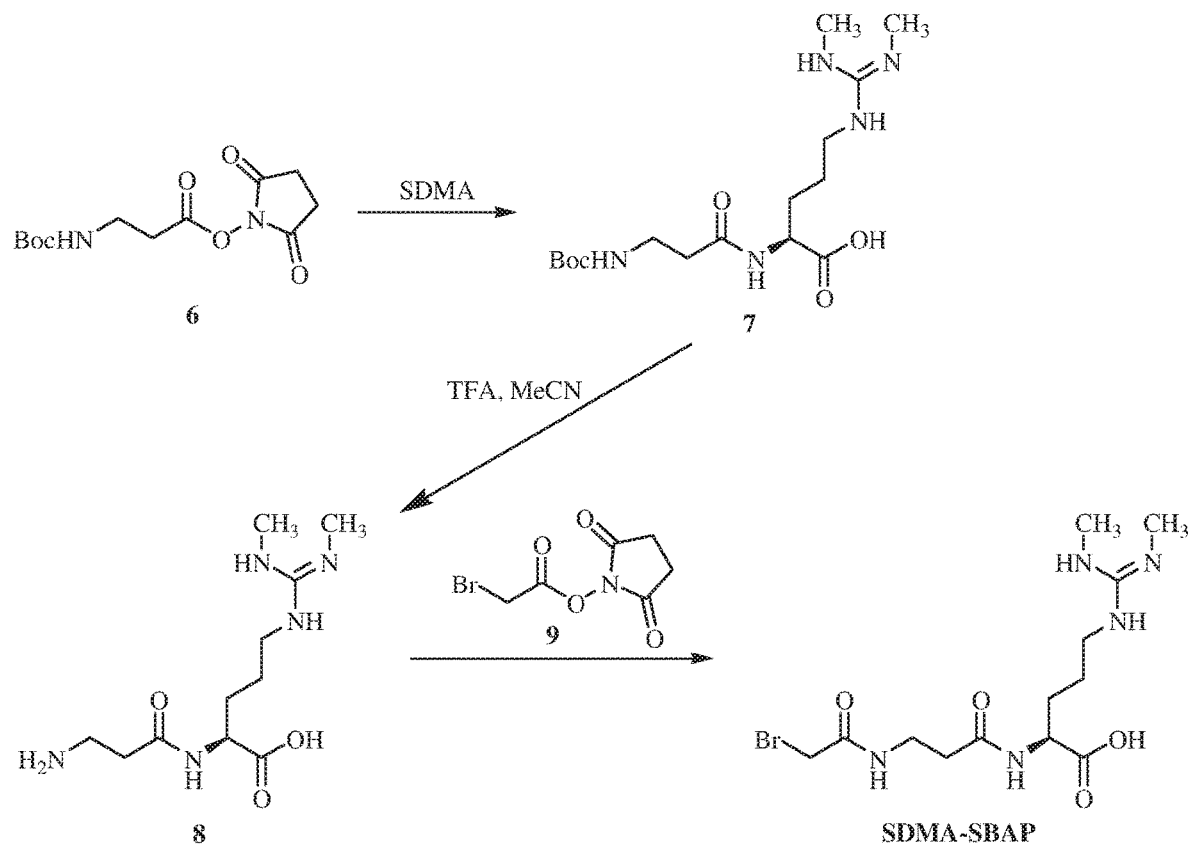
FIG. 6 shows the synthesis scheme for the SDMA-SBAP (Nα-acyl-SDMA) hapten, according to embodiments of the present disclosure.

A mixture of (8) (258 mg, 0.87 mmol, 1.0 equiv.), N-Succinimidyl bromoacetate (9) (205 mg, 0.87 mmol, 1.0 equiv.) and DIPEA (0.3 mL, 1.74 mmol, 2.0 equiv.) in DMF (2 mL) was stirred at 30° C. for 12 hours. LC-MS showed all the starting material transformed to target material. Solvent was removed under vacuum. The crude product was dissolved in MeCN and water (3.5 mL, 1/1, v/v) and then purified with Biotage reverse phase chromatography (standard method) to give the pure product SDMA-SBAP (175 mg, salt of TFA, 39.6% yield) as a clear oil. The structure was confirmed by $^1$H NMR. $^1$H NMR (400 MHz, D$_2$O) δ 4.36-4.32 (m, 1H), 3.83 (s, 2H), 3.45 (t, J=6.4, 2H), 3.18-3.15 (m, 2H), 2.76 (s, 6H), 2.49 (t, J=6.4, 2H), 1.87-1.74 (m, 1H), 1.73-1.58 (m, 3H). The reaction scheme is shown in FIG. 6.

Example 3

Preparation of SDMA-M-SH-KLH Immunogen

Figure 8:
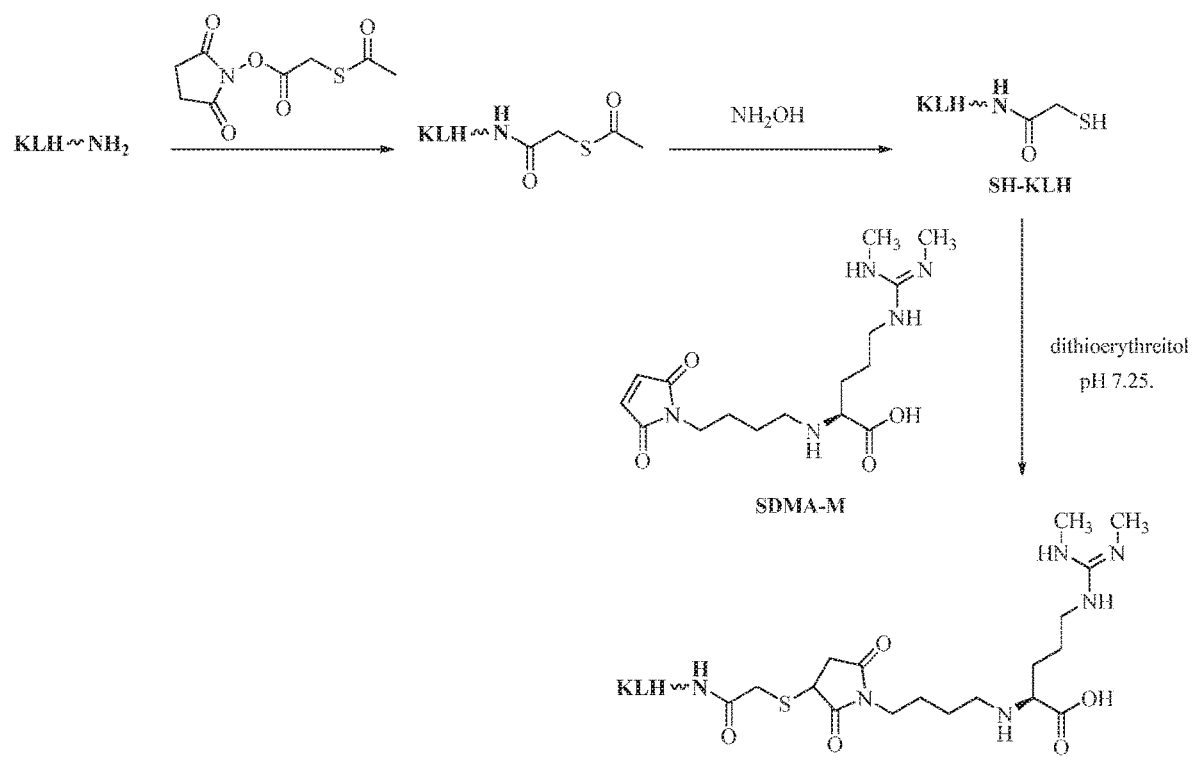
FIG. 8 shows the synthesis scheme for the SDMA-M-SH-KLH immunogen, according to embodiments of the present disclosure.

Hapten SDMA-M was conjugated to KLH where thiol groups were chemically introduced to KLH. N-Succinimidyl-S-acetylthioacetate was reacted with the primary amines of KLH, which added protected sulfhydryls. Deprotection of protected sulfhydryls with hydroxyl amine produced the desired thiolated SH-KLH (FIG. 8). Conjugation of hapten SDMA-M with SH-KLH resulted in immunogen SDMA-M-SH-KLH (see FIG. 8).

a) Preparation of SH-KLH

Lyophilized KLH (20 mg) was reconstituted with deionized water and pH adjusted to 8.6 with 1 M carbonate-bicarbonate buffer. A solution of N-Succinimidyl S-acetylthioacetate was prepared (4.67 mg was dissolved in 92 μL of DMF to a concentration of 220 mM) and slowly added to the KLH solution over 4 hrs. The reaction mixture was stirred at room temperature while N-Succinimidyl S-acetylthioacetate was being added, then stirred in the cold-room (4° C.) for an additional 16 hours.

Deacylation to generate a sulfhydryl for use in crosslinking was accomplished by adding 200 μL of a deacetylation solution (0.7 M hydroxylamine solution in 12.5 mM NaH$_2$PO$_4$—Na$_2$HPO$_4$ buffer, pH 7). Contents were mixed and reaction incubated for 2 hours at room temperature resulting in the product SH-KLH (see FIG. 8). EDTA was added at the end of this reaction to a concentration of 1 mM.

b) Preparation of SDMA-M-SH-KLH Immunogen

Dithiothreitol solution was added to the above SH-KLH solution for a total concentration of 1 mM to minimize disulfide bond formation. The pH was adjusted to 7.2 with 1 M carbonate-bicarbonate buffer. To the SH-KLH solution, 146 μl of maleimide derivative hapten SDMA-M dissolved in DMF (9.6 mg dissolved in 0.2 mL DMF) was added slowly over 4 to 5 hrs. The reaction was continued overnight at 4° C. The mixture was purified by dialysis using a 10,000 MWCO Slide-A-Lyzer® Dialysis Cassette (Pierce) in 4 liter NaH$_2$PO$_4$—Na$_2$HPO$_4$ buffer 12.5 mM, pH 7.0, at 2-8° C. This procedure yielded immunogen SDMA-M-SH-KLH (see FIG. 8).

Example 4

Preparation of SDMA-SBAP-SH-G6PDH Conjugate

Hapten SDMA-SBAP prepared as described in Example 2 is designed for proteins containing cysteine groups such as mutant G6PDH (see U.S. Pat. Nos. 6,455,288, 6,090,567, 6,033,890) or introduction of thiol-groups to G6PDH similarly as described in Example 3 by chemical reactions.

SDMA-SBAP hapten (7 mg, 0.018 mmol) was dissolved in DMF (0.21 mL). The solution was stirred at room temperature for 30 minutes. This SDMA-SBAP solution was used as described below.

Dithiothreitol solution was added to mutant G6PDH at a concentration of 2 mM to reduce cysteine thiol groups connected in disulfide bonds to sulfhydryl groups. The resulting enzyme solution (0.9 mg, 1.5 mL) was adjusted to pH 7.2 with 1 M carbonate bi-carbonate buffer and mixed with approximately 340 fold molar excess (0.07 mL) of SDMA-SBAP hapten. The reaction mixture was allowed to stir gently at 4° C. for 16 hours. Excess SDMA-SBAP hapten was separated from the enzyme-hapten conjugate by passing the reaction mixture over a column of Sephadex G-50 in 12.5 mM NaH$_2$PO$_4$—Na$_2$HPO$_4$ buffer, pH 7.0. The column fractions containing the enzyme-hapten conjugate are pooled by measuring absorption at 280 nm to give conjugate SDMA-SBAP-SH-G6PDH (see FIG. 7).

Hapten SDMA-SBAP was conjugated with BSA using a conjugation procedure similar to that described above. The SDMA-SBAP-SH-BSA conjugate (FIG. 9) was used to screen B-cells and monoclonal antibodies by indirect ELISA as described in Example 6.

Example 5

Preparation of Polyclonal Antibodies to SDMA

Twenty-four female white New Zealand rabbits were immunized by injecting subcutaneously 200 μg/rabbit of SDMA-M-SH-KLH immunogen, as prepared in Example 3, emulsified in Complete Freund's adjuvant. The rabbits were boosted every four weeks after the initial injection with 100 μg/rabbit of the same immunogen emulsified in Incomplete Freund's Adjuvant. One hundred and thirty-four days after the initial immunization, bleeds containing polyclonal antibodies from each rabbit were obtained from the central ear artery. The anti-serum from these bleeds containing SDMA-M-SH-KLH antibodies were evaluated in a homogeneous assay format (FIG. 10) by measuring maximum antibody inhibition of enzyme conjugate SDMA-SBAP-SH-G6PDH and modulation in the presence of symmetric dimethylarginine as described in Examples 7 and 8.

From these experiments rabbits 21342 and 26494 were selected to isolate PBMC's as a source of B-cells for cloning (Example 6) from rabbits immunized with SDMA-M-SH-KLH immunogen. Initial screening results of the 24 rabbit polyclonal antisera immunized with SDMA-M-SH-KLH is shown in Table 1 below.

TABLE 1

| Rabbit ID | Max. Inhibition (%) | Modulation (%) |
|---|---|---|
| #21331 | 32 | 8 |
| #21332 | 39 | 10 |
| #21333 | 17 | 6 |
| #21334 | 39 | 12 |
| #21335 | 32 | 12 |
| #21336 | 31 | 7 |
| #21337 | 27 | 4 |
| #21338 | 52 | 13 |
| #21339 | 51 | 13 |
| #21340 | 11 | 2 |
| #21341 | 32 | 8 |
| #21342 | 48 | 14 |
| #27410 | 45 | 16 |
| #26490 | 23 | 8 |
| #26491 | 4 | 2 |
| #26492 | 26 | 6 |
| #26493 | 11 | 2 |
| #26494 | 36 | 22 |
| #26496 | 31 | 9 |
| #26497 | 14 | 3 |
| #26498 | 4 | 0 |
| #26499 | 6 | 4 |
| #26500 | 31 | 5 |
| #26501 | 25 | 8 |

Example 6

Preparation Rabbit Monoclonal Antibody

Rabbit recombinant monoclonal antibodies were prepared using single B-cell screening strategy for efficiently sampling the natural antibody repertoire of immunized rabbits. This technique is generally applicable to produce monoclonal antibodies to symmetric dimethylarginine as described herein.

Rabbit Peripheral blood mononuclear cells (PBMC's) from immunized animals #21342 and #26494 were used as a source of B-cells. PBMC's were isolated from approximately 40 mL whole blood from each rabbit using standard density gradient centrifugation procedure. The PBMC's were diluted in PBS and theoretically dispensing single cell per well into forty 96-well plates the same day and cultured.

Figure 9:
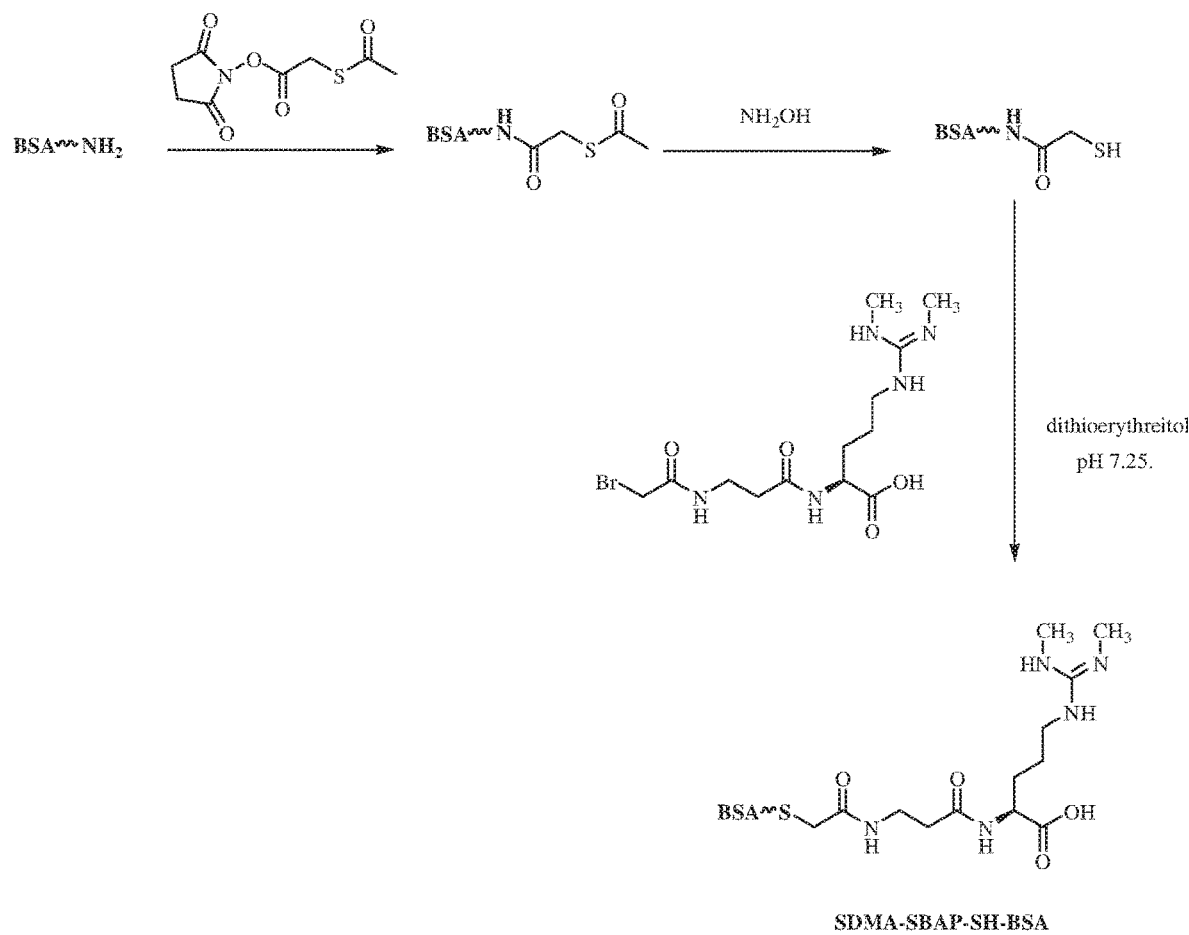
FIG. 9 shows the synthesis scheme for the SDMA-SBAP-SH-BSA immunogen, according to embodiments of the present disclosure.

Resulting supernatants from each well were tested by indirect ELISA against SDMA-SBAP-SH-BSA antigen (FIG. 9). Forty 96-well microtiter plates were coated with 0.1 g/well SDMA-SBAP-SH-BSA in 0.1 M carbonate buffer, pH 9.5 and stored over night at 4° C. The plates were emptied and then blocked with 3% skimmed milk powder in PBST with shaking for 1 hr at RT. After flicking off the blocking solution the plates were rinsed with PBST. Twenty-five μL of PBST were added to each well followed by adding 25 μL of cell supernatant to all the wells and incubated for 1 hr at 37° C. in an incubator. Plates were washed 5× with PBST with a total wash time of 30 min. Afterwards, 100 μL/well secondary antibody 1:10,000 (v/v) goat anti-rabbit IgGFc-HRP conjugate in PBST was added and plates were incubated for 1 hour at 37° C. under constant shaking. Plates were washed 5 times with PBST, total wash time of 30 min. TMB substrate was added at 50 uL/well, plates. After a five minute incubation in the dark for color to develop, the reaction was stopped by the addition of 50 μL of 1 N HCl. Color was read via a microplate reader at 450 nm, and data was transferred to a computer for analysis. Supernatants that bound the SDMA-M-SH-BSA conjugate (produced color in the wells) were considered positives. A total of 32 cells were selected for cloning and expression.

For each ELISA well with an antigen-specific antibody, mRNA was isolated from the corresponding PBMC culture well and divided to separately synthesize cDNA from the variable regions of the rabbit genes, IgH and IgK. After two rounds of PCR to amplify, the cDNA was seamlessly ligated into separate mammalian expression vectors with a constant IgG region of the heavy chain or the constant IgK region of the light chain, respectively. Ligation mixtures were transformed into E. coli to select correct expression constructs and cultured to isolate plasmid. The expression constructs were co-transfected into HEK293 cells. Transfected cells were cultured 2 days to secrete the recombinant antibody. The antigen binding property of the recombinantly expressed antibodies were assessed by indirect ELIA against SDMA-SBAP-BSA antigen as described above. The clones selected were further used for evaluation in the homogeneous enzyme immunoassay format as described on Examples 7 and 8. DNA sequencing was performed for selected rabbit monoclonal antibodies and translated with a standard code to provide protein sequence data for all heavy chain and kappa chain variable region sequences. The Table below summarizes the development phases resulting in monoclonal antibodies.

TABLE 2

| Immunization Phase | | | Enrichment & Selection Phase No. B cells | | Cloning & Expression Phase | |
|---|---|---|---|---|---|---|
| No. rabbits immunized | Immunogen | Rabbit ID no. selected for cloning | positive by indirect ELISA against SDMA-SBAP-BSA antigen | | No. of cells cloned and expressed | ID of clones selected for testing and sequencing |
| 24 | KLH-SH-SDMA-M | #21342 | 190 | | 23 | 1H4/1K4 8H1/8K3 18H1/18K2 |
| | | #26494 | 58 | | 29 | 1H2/1K4 3H1/3K3 5H1/5K1 |

Example 7

Preparation of SDMA Standards and Calibration Protocol

Symmetric dimethylarginine di(p-hydroxyazobenzene-p'-sulfonate) salt (Sigma) was dissolved in DMF:H$_2$O (1:1), and diluted in a synthetic matrix to a final concentration of SDMA of 4 µg/ml stock solution. SDMA stock solution was transferred into aliquots of synthetic matrix to achieve levels of 0, 15, 50, 100, 150, 200 µg/dL. The synthetic matrix consisted of a proteinaceous solution buffered with HEPES (6.5 mM, pH 6.7), and EDTA (0.25 mM), surfactant, defoaming agent and a preservative. The standards were validated by LC/MS (see FIG. 17).

A six-point calibration curve was used to quantify symmetrically dimethylated arginine in samples. Calibration curves were generated on the Beckman Coulter AU480 automated clinical chemistry analyzer (see Examples 7 and 8) by measuring each calibrator level in duplicate.

Nα-acetyl-dimethylarginine (Ac-SDMA) calibrators were prepared in a similar manner as described above. Nα-acetyl-dimethylarginine was synthesized by SYNthesis med chem (Australia).

Example 8

Reagents and Assays

Symmetric dimethylarginine antibodies and enzyme conjugates may be advantageously used in accordance with the present disclosure in a homogeneous assay format to detect a symmetric dimethylated arginine analyte in samples. Antibodies may be evaluated by known methods, such as, conjugate inhibition, conjugate modulation, calibration, cross-reactivity and spike-recovery. For these purposes, antibody (polyclonal antibodies rabbit #21342, rabbit #26494, or rabbit #27420, or cloned antibodies 1H4/1K4, 8H1/8K3, 18H1/18K2, 1H2/1K4, 3H1/3K3, or 5H1/5K1) is added into the antibody diluent to prepare the antibody reagent. The antibody reagent includes antibody as prepared above, buffer, salts, stabilizers, preservatives, NAD$^+$, and glucose-6-phosphate. Enzyme conjugate SDMA-SBAP-SH-G6PDH is added into the conjugate diluent to prepare the enzyme conjugate reagent. The enzyme conjugate reagent includes the conjugate, buffer, stabilizers, salts, and preservatives.

A clinical chemistry analyzer useful to evaluate antibodies and enzyme conjugates in a homogeneous enzyme immunoassay format is the Beckman Coulter AU480 (Beckman Coulter, Brea, Calif.). The Beckman AU480 is an automated biochemistry spectrophotometer analyzer used by medical laboratories to process biological fluid specimens, such as urine, cerebrospinal fluid, oral fluids, plasma and serum. The analyzer is capable of maintaining a constant temperature, pipetting samples, mixing reagents, measuring light absorbance and timing the reaction accurately.

A homogeneous enzyme immunoassay is conducted using a liquid, ready-to-use, two reagent assay as described above. Typically, 2-15 µL symmetrically dimethylated arginine analyte-containing sample is incubated with 75-150 µL antibody reagent followed by the addition of the 50-100 µL enzyme conjugate reagent.

The assay is a homogeneous enzyme immunoassay technique used for the analysis of SDMA in biological fluids. The assay is based on competition between SDMA in the specimen and Nα-acylated-SDMA or Nα-alkylated-SDMA labeled with the enzyme glucose-6-phosphate dehydrogenase (G6PDH) for antibody binding sites. Enzyme activity decreases upon binding to the antibody, so the drug concentration in the sample can be measured in terms of enzyme activity. Active enzyme converts nicotinamide adenine dinucleotide (NAD$^+$) to NADH, resulting in an absorbance change that is measured spectrophotometrically at 340 nm. Endogenous serum G6PDH does not interfere because the coenzyme NAD$^+$ functions only with the bacterial (*Leuconostoc mesenteroides*) enzyme employed in the assay. The change in the absorbance at 340 nm can be measured spectrophotometrically and is proportional to the enzyme conjugate activity which in turn is related to analyte concentration (see FIG. 10).

Example 9

Antibodies and Calibration using Symmetric Dimethylarginine Analyte

Figure 11:
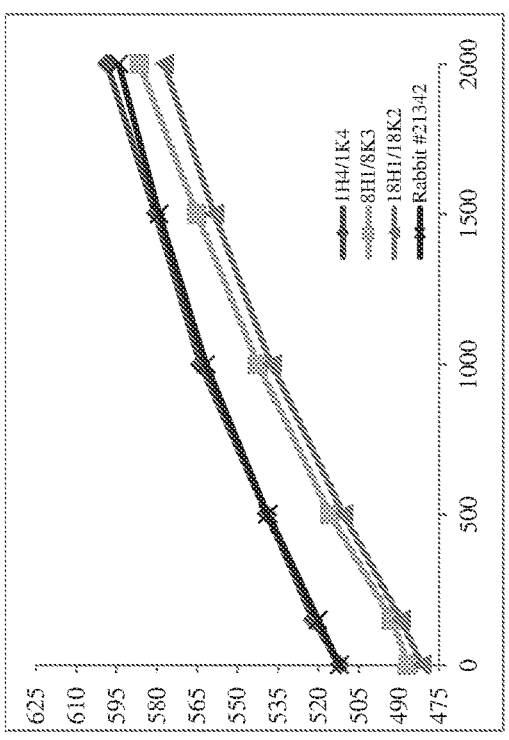
FIG. 11 shows a graph of a symmetric dimethylarginine calibration curve using rabbit polyclonal antibody #26494, monoclonal antibody 1H2/1K4, monoclonal antibody 3H1/

Symmetric dimethylated arginine analyte antibodies and enzyme conjugate (SDMA-SBAP-SH-G6PDH) were used in a homogeneous assay format to generate calibration curves using symmetric dimethylarginine standards as described in Example 7. Antibody reagents were prepared as described in Example 8 using symmetric dimethylated arginine analyte polyclonal antibodies rabbit #21342, rabbit #26494, rabbit #27420 and cloned antibodies 1H4/1K4, 8H1/8K3, 18H1/18K2, 1H2/1K4, 3H1/3K3, or 5H1/5K1. Enzyme conjugate SDMA-SBAP-SH-G6PDH was used to prepare the conjugate reagent. A 6-point calibration curve was generated on the Beckman AU480 clinical chemistry analyzer as described in Examples 7 and 8. Typical calibration curves are shown in the table below and dose-response curves shown in FIG. 11 and FIG. 12. These experiments demonstrated that polyclonal antibodies rabbit #21342, rabbit #26494, rabbit #27420 and cloned monoclonal antibodies 1H4/1K4, 8H1/8K3, 18H1/18K2, 1H2/1K4, 3H1/3K3, or 5H1/5K1 have antibody binding reaction to symmetric dimethylarginine demonstrating a dose-response relationship.

TABLE 3

| SDMA Conc. | Rabbit Polyclonal Antibody Reaction Rate (mA/min) Average of Duplicates | | |
|---|---|---|---|
| (µg/dL) | Rabbit #21342 | Rabbit #26494 | Rabbit #27420 |
| 0 | 528 | 585 | 576 |
| 15 | 559 | 634 | 624 |
| 50 | 607 | 703 | 690 |
| 100 | 656 | 755 | 734 |
| 150 | 685 | 783 | 753 |
| 200 | 705 | 798 | 765 |

| SDMA Conc. | Rabbit Recombinant Antibody Reaction Rate (mA/min) Average of Duplicates | | |
|---|---|---|---|
| (µg/dL) | 1H4/1K4 | 8H1/8K3 | 18H1/18K2 |
| 0 | 535 | 497 | 492 |
| 15 | 564 | 534 | 531 |
| 50 | 617 | 598 | 595 |
| 100 | 669 | 652 | 649 |
| 150 | 698 | 686 | 681 |
| 200 | 714 | 708 | 702 |

TABLE 3-continued

| SDMA Conc. | Rabbit Recombinant Antibody Reaction Rate (mA/min) Average of Duplicates | | |
|---|---|---|---|
| (μg/dL) | 1H2/1K4 | 3H1/3K3 | 5H1/5K1 |
| 0 | 592 | 523 | 574 |
| 15 | 630 | 595 | 617 |
| 50 | 687 | 704 | 671 |
| 100 | 736 | 767 | 710 |
| 150 | 756 | 794 | 730 |
| 200 | 767 | 807 | 743 |

Example 10

Antibodies and Calibration Using Nα-Acetyl-Symmetric Dimethylarginine Analyte Symmetric dimethylated arginine analyte antibodies and enzyme conjugate (SDMA-SBAP-SH-G6PDH) were used in a homogeneous assay format to generate calibration curves using standards prepared using Nα-Acetyl-symmetric dimethylarginine as described in Example 7. Antibody reagents were prepared as described in Example 8 using symmetric dimethylated arginine analyte polyclonal antibodies rabbit #21342, rabbit #26494, rabbit #27420 and cloned antibodies 1H4/1K4, 8H1/8K3, 18H1/18K2, 1H2/1K4, 3H1/3K3, or 5H1/5K1. Enzyme conjugate SDMA-SBAP-SH-G6PDH was used to prepare the conjugate reagent. A 6-point calibration curve was generated on the Beckman AU480 clinical chemistry analyzer as described in Example 8. Typical calibration curves are shown in the table below and dose-response curves shown in FIG. 13 and FIG. 14. These experiments demonstrated that polyclonal antibodies rabbit #21342, rabbit #26494, rabbit #27420 and cloned monoclonal antibodies 1H4/1K4, 8H1/8K3, 18H1/18K2, 1H2/1K4, 3H1/3K3, or 5H1/5K1 have an antibody binding reaction to Nα-Acetyl-symmetric dimethylarginine demonstrating a dose-response relationship.

TABLE 4

| Ac-SDMA Conc. | Rabbit Polyclonal Antibody Reaction Rate (mA/min) Average of Duplicates | | |
|---|---|---|---|
| (μg/dL) | Rabbit #21342 | Rabbit #26494 | Rabbit #27420 |
| 0 | 519 | 542 | 571 |
| 15 | 533 | 551 | 576 |
| 50 | 559 | 561 | 578 |
| 100 | 591 | 581 | 589 |
| 150 | 612 | 595 | 598 |
| 200 | 632 | 608 | 605 |

| Ac-SDMA Conc. | Rabbit Recombinant Antibody Reaction Rate (mA/min) Average of Duplicates | | |
|---|---|---|---|
| (μg/dL) | 1H4/1K4 | 8H1/8K3 | 18H1/18K2 |
| 0 | 521 | 481 | 480 |
| 15 | 538 | 501 | 498 |
| 50 | 569 | 537 | 535 |
| 100 | 603 | 577 | 575 |
| 150 | 628 | 605 | 601 |
| 200 | 647 | 626 | 622 |

| Ac-SDMA Conc. | Rabbit Recombinant Antibody Reaction Rate (mA/min) Average of Duplicates | | |
|---|---|---|---|
| (μg/dL) | 1H2/1K4 | 3H1/3K3 | 5H1/5K1 |
| 0 | 589 | 483 | 572 |
| 15 | 592 | 488 | 578 |
| 50 | 594 | 502 | 587 |
| 100 | 606 | 519 | 602 |
| 150 | 612 | 529 | 611 |
| 200 | 620 | 546 | 623 |

Example 11

Spike-Recovery

Known amounts of symmetrically methylated arginine analyte stock solution (4 μg/mL) were added (spike) into synthetic matrix as described in Example 7 to achieve concentrations of 0, 15, 50, 100, 150, 200 μg/dL. These samples were quantified in triplicate by the homogeneous enzyme immunoassay to confirm concentration (recovery) of the spiked samples on the Beckman AU480 as described in Example 8. The samples were quantified using a separately prepared set of standards by generating a 6-point calibration curve. Calibration curve was generated using standards prepared using the same analyte as the analyte being quantified in the sample being tested. The Enzyme Conjugate Reagent contained conjugate SDMA-SBAP-SH-G6PDH and the Antibody Reagents were prepared containing polyclonal antibody from rabbit #21342, rabbit #26494, rabbit #27420 and antibody clones 1H4/1K4, 8H1/8K3, 18H1/18K2, 1H2/1K4, 3H1/3K3, or 5H1/5K1. The symmetrically methylated arginine analyte concentration recovered in the spike-recovery experiments were compared to the known concentration and plotted (FIGS. 15-18). These experiments demonstrated that polyclonal antibodies rabbit #21342, rabbit #26494, rabbit #27420 and cloned antibodies 1H4/1K4, 8H1/8K3, 18H1/18K2, 1H2/1K4, 3H1/3K3, or 5H1/5K1 have antibody reaction to symmetric dimethylarginine and Nα-acetyl-SDMA.

In another experiment, the same samples as above were quantified in triplicate by the homogeneous enzyme immunoassay (see Example 8) and by LC-MS-MS in duplicate. Deuterated asymmetric dimethylarginine an internal standard was used for the LC-MS-MS method. The homogeneous enzyme immunoassay was prepared using clone 3H1/3K3 in the antibody reagent and enzyme conjugate SDMA-SBAP-SH-G6PDH in the enzyme conjugate reagent. Results show that the homogeneous enzyme immunoassay quantifies SDMA levels in agreement with LC-MS-MS.

In another experiment, known amounts of SDMA-Gly-Gly dipeptide were analyzed in the homogeneous enzyme immunoassay to confirm concentration (recovery) of the spiked samples on the Beckman AU480 as described in Example 8. Calibration curve was generated using standards prepared using the same analyte as the analyte being quantified in the sample being tested. The Enzyme Conjugate Reagent contained conjugate SDMA-SBAP-SH-G6PDH and the Antibody Reagents were prepared containing antibody clone 8H1/8K3 or 3H1/3K3. The SDMA-Gly-Gly dipeptide analyte concentration recovered in the spike-recovery experiments were compared to the known concentration and plotted (FIG. 19).

Example 12

Antibody and Calibration Using Symmetric Dimethylarginine and Nα-Acetyl-Symmetric Dimethylarginine Analytes Polyclonal antibody from rabbit #27410 and SDMA-SBAP-SH-G6PDH were used to prepare reagents and used in homogeneous assay format to detect symmetric dimethylated arginine and Nα-Ac-SDMA analytes as described in Example 8. The SDMA and Nα-Ac-SDMA samples were prepared as described in Example 7 and were quantified from a calibration curve generated from standards prepared using SDMA. Spike-recovery experiments were performed as described in Example 11 using the polyclonal antibody from rabbit #27410. FIG. 20 shows that polyclonal antibody from rabbit #27410 substantially binds both SDMA and Nα-Ac-SDMA. The maximum inhibition (%) and modulation (%) for the polyclonal antibody from rabbit #27410 is shown in Table 1 above.

The preceding merely illustrates the principles of the embodiments of the present disclosure. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the embodiments and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

What is claimed is:

1. A compound of Formula 1:

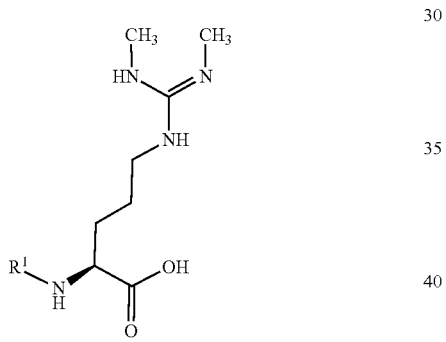

wherein:
$R^1$ is —Y—Z;
Y is a linking group; and
Z is a label enzyme.

2. The compound of claim 1, wherein the linking group is selected from the group consisting of —(CH$_2$)$_n$C(O)—, —C(O)(CH$_2$)$_n$—, —C(O)(CH$_2$)$_n$NHC(O)—, —C(O)(CH$_2$)$_n$NHC(O)(CH$_2$)$_n$—, —(CH$_2$)$_n$SCH$_2$C(O)—, —(CH$_2$)$_n$C(O)NH(CH$_2$)$_n$—, —(CH$_2$)$_n$NHC(O)—, —(CH$_2$)$_n$NHC(O)(CH$_2$)$_n$—, —NH(CH$_2$)$_n$C(O)—, —(CH$_2$)$_n$—, —(CH$_2$)$_n$(heterocyclyl)S(CH$_2$)$_n$C(O)—, and n is an integer from 1 to 10.

3. The compound of claim 1, wherein the label enzyme is glucose-6-phosphate dehydrogenase (G6PDH).

4. A compound of Formula 1:

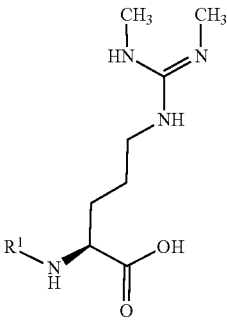

wherein:
$R^1$ is —Y—Z;
Y is a linking group selected from the group consisting of —(CH$_2$)$_n$C(O)—, —C(O)(CH$_2$)$_n$—, —C(O)(CH$_2$)$_n$NHC(O)—, —C(O)(CH$_2$)$_n$NHC(O)(CH$_2$)$_n$—, —(CH$_2$)$_n$SCH$_2$C(O)—, —(CH$_2$)$_n$C(O)NH(CH$_2$)$_n$—, —(CH$_2$)$_n$NHC(O)—, —(CH$_2$)$_n$NHC(O)(CH$_2$)$_n$—, —NH(CH$_2$)$_n$C(O)—, —(CH$_2$)$_n$—, —(CH$_2$)$_n$(heterocyclyl)S(CH$_2$)$_n$C(O)—, and n is an integer from 1 to 10; and
Z is a label enzyme,
and acid salts thereof.

5. The compound of claim 4, wherein the label enzyme is glucose-6-phosphate dehydrogenase (G6PDH).

* * * * *

SEQUENCE LISTING

```
<160> NUMBER OF SEQ ID NOS: 41

<210> SEQ ID NO 1
<211> LENGTH: 135
<212> TYPE: PRT
<213> ORGANISM: Artificial sequence
<220> FEATURE:
<223> OTHER INFORMATION: synthetic sequence

<400> SEQUENCE: 1

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Thr Met Gly Trp Val Arg Gln Ala Pro Gly Lys Gly Leu Glu
    50                  55                  60

Trp Ile Gly Asp Ile Lys Thr Gly Asp Arg Thr Tyr Tyr Ala Asn Trp
65                  70                  75                  80

Ala Lys Gly Arg Phe Thr Ile Ser Arg Thr Ser Thr Thr Val Asp Leu
                85                  90                  95

Lys Met Thr Ser Leu Thr Thr Glu Asp Thr Ala Thr Tyr Phe Cys Ala
            100                 105                 110

Arg Val Tyr Val Ser Gly Asn Asp His Tyr Asp Leu Trp Gly Gln Gly
        115                 120                 125

Thr Leu Val Thr Val Ser Ser
    130                 135

<210> SEQ ID NO 2
<211> LENGTH: 7
<212> TYPE: PRT
<213> ORGANISM: Artificial sequence
<220> FEATURE:
<223> OTHER INFORMATION: synthetic sequence

<400> SEQUENCE: 2

Gly Phe Ser Leu Ser Ser Tyr
1               5

<210> SEQ ID NO 3
<211> LENGTH: 7
<212> TYPE: PRT
<213> ORGANISM: Artificial sequence
```

```
<220> FEATURE:
<223> OTHER INFORMATION: synthetic sequence

<400> SEQUENCE: 3

Asp Ile Lys Thr Gly Asp Arg
1               5

<210> SEQ ID NO 4
<211> LENGTH: 13
<212> TYPE: PRT
<213> ORGANISM: Artificial sequence
<220> FEATURE:
<223> OTHER INFORMATION: synthetic sequence

<400> SEQUENCE: 4

Ala Arg Val Tyr Val Ser Gly Asn Asp His Tyr Asp Leu
1               5                   10

<210> SEQ ID NO 5
<211> LENGTH: 132
<212> TYPE: PRT
<213> ORGANISM: Artificial sequence
<220> FEATURE:
<223> OTHER INFORMATION: synthetic sequence

<400> SEQUENCE: 5

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
                20                  25                  30

Val Glu Val Ala Val Gly Gly Thr Val Thr Ile Lys Cys Gln Ala Ser
            35                  40                  45

Gln Ser Ile Ser Asn Tyr Leu Ala Trp Tyr Gln Gln Lys Pro Gly Gln
        50                  55                  60

Pro Pro Lys Leu Leu Ile Tyr Arg Ala Ser Thr Leu Ala Ser Gly Val
65                  70                  75                  80

Pro Ser Arg Phe Lys Gly Ser Gly Arg Gly Thr Glu Phe Thr Leu Thr
                85                  90                  95

Ile Ser Gly Val Glu Cys Ala Asp Ala Ala Thr Tyr Tyr Cys Gln Leu
            100                 105                 110

Gly Tyr Thr Tyr Ser Asn Val Glu Asn Ala Phe Gly Gly Gly Thr Glu
        115                 120                 125

Val Val Val Lys
        130

<210> SEQ ID NO 6
<211> LENGTH: 6
<212> TYPE: PRT
<213> ORGANISM: Artificial sequence
<220> FEATURE:
<223> OTHER INFORMATION: synthetic sequence

<400> SEQUENCE: 6

Gln Ser Ile Ser Asn Tyr
1               5

<210> SEQ ID NO 7
<211> LENGTH: 3
<212> TYPE: PRT
<213> ORGANISM: Artificial sequence
<220> FEATURE:
<223> OTHER INFORMATION: synthetic sequence
```

```
<400> SEQUENCE: 7

Arg Ala Ser
1

<210> SEQ ID NO 8
<211> LENGTH: 12
<212> TYPE: PRT
<213> ORGANISM: Artificial sequence
<220> FEATURE:
<223> OTHER INFORMATION: synthetic sequence

<400> SEQUENCE: 8

Gln Leu Gly Tyr Thr Tyr Ser Asn Val Glu Asn Ala
1               5                   10

<210> SEQ ID NO 9
<211> LENGTH: 132
<212> TYPE: PRT
<213> ORGANISM: Artificial sequence
<220> FEATURE:
<223> OTHER INFORMATION: synthetic sequence

<400> SEQUENCE: 9

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
                20                  25                  30

Val Glu Val Ala Val Gly Gly Thr Val Thr Ile Lys Cys Gln Ala Ser
            35                  40                  45

Gln Ser Ile Ser Asn Tyr Leu Ala Trp Tyr Gln Gln Lys Pro Gly Gln
        50                  55                  60

Pro Pro Lys Leu Leu Ile Tyr Arg Ala Ser Asn Leu Ala Ser Gly Val
65                  70                  75                  80

Ser Ser Arg Phe Lys Gly Ser Gly Arg Gly Thr Glu Phe Thr Leu Thr
                85                  90                  95

Ile Ser Gly Val Glu Cys Ala Asp Ala Ala Thr Tyr Tyr Cys Gln Leu
            100                 105                 110

Gly Tyr Thr Tyr Thr Asn Val Glu Asn Ala Phe Gly Gly Gly Thr Glu
        115                 120                 125

Val Val Val Lys
        130

<210> SEQ ID NO 10
<211> LENGTH: 12
<212> TYPE: PRT
<213> ORGANISM: Artificial sequence
<220> FEATURE:
<223> OTHER INFORMATION: synthetic sequence

<400> SEQUENCE: 10

Gln Leu Gly Tyr Thr Tyr Thr Asn Val Glu Asn Ala
1               5                   10

<210> SEQ ID NO 11
<211> LENGTH: 135
<212> TYPE: PRT
<213> ORGANISM: Artificial sequence
<220> FEATURE:
<223> OTHER INFORMATION: synthetic sequence
```

```
<400> SEQUENCE: 11

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Ser Glu Gly Ser Leu Thr Leu Thr Cys Thr Ala Ser Gly Phe Ser Phe
        35                  40                  45

Ser Ser Thr Lys Tyr Met Cys Trp Val Arg Gln Ala Pro Gly Lys Arg
    50                  55                  60

Pro Glu Trp Ile Ala Cys Ile Gly Thr Asp Thr Thr Tyr Tyr Ala Ser
65                  70                  75                  80

Trp Ala Lys Gly Arg Phe Thr Ile Ser Arg Thr Ser Thr Thr Val
                85                  90                  95

Thr Leu Gln Met Thr Ser Leu Thr Ala Ala Asp Thr Ala Thr Tyr Phe
                100                 105                 110

Cys Ala Arg Ser Ser Ser Thr Gly Tyr Tyr Asn Leu Trp Gly Gln Gly
            115                 120                 125

Thr Leu Val Thr Val Ser Ser
        130                 135

<210> SEQ ID NO 12
<211> LENGTH: 8
<212> TYPE: PRT
<213> ORGANISM: Artificial sequence
<220> FEATURE:
<223> OTHER INFORMATION: synthetic sequence

<400> SEQUENCE: 12

Gly Phe Ser Phe Ser Ser Thr Lys
1               5

<210> SEQ ID NO 13
<211> LENGTH: 6
<212> TYPE: PRT
<213> ORGANISM: Artificial sequence
<220> FEATURE:
<223> OTHER INFORMATION: synthetic sequence

<400> SEQUENCE: 13

Cys Ile Gly Thr Asp Thr
1               5

<210> SEQ ID NO 14
<211> LENGTH: 11
<212> TYPE: PRT
<213> ORGANISM: Artificial sequence
<220> FEATURE:
<223> OTHER INFORMATION: synthetic sequence

<400> SEQUENCE: 14

Ala Arg Ser Ser Ser Thr Gly Tyr Tyr Asn Leu
1               5                   10

<210> SEQ ID NO 15
<211> LENGTH: 131
<212> TYPE: PRT
<213> ORGANISM: Artificial sequence
<220> FEATURE:
<223> OTHER INFORMATION: synthetic sequence
```

```
<400> SEQUENCE: 15

Met Asp Thr Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Pro Ala
            20                  25                  30

Ser Val Ser Glu Pro Val Gly Gly Thr Val Thr Ile Lys Cys Gln Ala
        35                  40                  45

Ser Gln Ser Ile Arg Ser Tyr Leu Ala Trp Tyr Gln Gln Lys Pro Gly
    50                  55                  60

Gln Pro Pro Lys Leu Leu Ile Tyr Tyr Ala Ser Thr Leu Ala Ser Gly
65                  70                  75                  80

Val Ser Ser Arg Phe Lys Gly Ser Gly Ser Gly Thr Glu Phe Thr Leu
                85                  90                  95

Thr Ile Asn Gly Val Gln Cys Asp Asp Ala Ala Thr Tyr Tyr Cys His
            100                 105                 110

Asp Tyr Tyr Thr Phe Thr Asp Asn Asp Phe Gly Gly Gly Thr Glu Val
        115                 120                 125

Val Val Lys
    130

<210> SEQ ID NO 16
<211> LENGTH: 6
<212> TYPE: PRT
<213> ORGANISM: Artificial sequence
<220> FEATURE:
<223> OTHER INFORMATION: synthetic sequence

<400> SEQUENCE: 16

Gln Ser Ile Arg Ser Tyr
1               5

<210> SEQ ID NO 17
<211> LENGTH: 3
<212> TYPE: PRT
<213> ORGANISM: Artificial sequence
<220> FEATURE:
<223> OTHER INFORMATION: synthetic sequence

<400> SEQUENCE: 17

Tyr Ala Ser
1

<210> SEQ ID NO 18
<211> LENGTH: 10
<212> TYPE: PRT
<213> ORGANISM: Artificial sequence
<220> FEATURE:
<223> OTHER INFORMATION: synthetic sequence

<400> SEQUENCE: 18

His Asp Tyr Tyr Thr Phe Thr Asp Asn Asp
1               5                   10

<210> SEQ ID NO 19
<211> LENGTH: 138
<212> TYPE: PRT
<213> ORGANISM: Artificial sequence
<220> FEATURE:
<223> OTHER INFORMATION: synthetic sequence
```

<400> SEQUENCE: 19

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Ser Phe
        35                  40                  45

Ser Ser Thr Lys Tyr Met Cys Trp Val Arg Gln Ala Pro Gly Arg Gly
    50                  55                  60

Pro Glu Trp Val Ala Cys Ile Gly Val Gly Ser Arg Gly Ser Thr Tyr
65                  70                  75                  80

Tyr Ala Ser Arg Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Ser Ser Thr Thr Gly Tyr Tyr Ile Leu Trp
        115                 120                 125

Gly Gln Gly Thr Leu Val Thr Val Ser Ser
    130                 135

<210> SEQ ID NO 20
<211> LENGTH: 9
<212> TYPE: PRT
<213> ORGANISM: Artificial sequence
<220> FEATURE:
<223> OTHER INFORMATION: synthetic sequence

<400> SEQUENCE: 20

Cys Ile Gly Val Gly Ser Arg Gly Ser
1               5

<210> SEQ ID NO 21
<211> LENGTH: 11
<212> TYPE: PRT
<213> ORGANISM: Artificial sequence
<220> FEATURE:
<223> OTHER INFORMATION: synthetic sequence

<400> SEQUENCE: 21

Ala Arg Ser Ser Thr Thr Gly Tyr Tyr Ile Leu
1               5                   10

<210> SEQ ID NO 22
<211> LENGTH: 130
<212> TYPE: PRT
<213> ORGANISM: Artificial sequence
<220> FEATURE:
<223> OTHER INFORMATION: synthetic sequence

<400> SEQUENCE: 22

Met Asp Thr Arg Ala Pro Thr Gln Leu Leu Gly Leu Leu Leu Leu Trp
1               5                   10                  15

Leu Pro Gly Ala Arg Cys Ala Phe Glu Met Thr Gln Thr Pro Ser Ser
            20                  25                  30

Val Ser Ala Ala Val Gly Gly Thr Val Thr Ile Lys Cys Gln Ala Ser
        35                  40                  45

Glu Ser Ile Tyr Ser Tyr Leu Ala Trp Tyr Gln Gln Lys Pro Gly Gln
    50                  55                  60

Pro Pro Lys Leu Leu Ile Tyr Lys Ala Ser Thr Leu Ala Ser Gly Val
65                  70                  75                  80

Ser Ser Arg Phe Lys Gly Ser Gly Ser Gly Thr Glu Phe Thr Leu Thr
            85                  90                  95

Ile Ser Gly Val Gln Cys Asp Asp Ala Ala Thr Tyr Tyr Cys Gln Asn
                100                 105                 110

Tyr Tyr Thr Phe Thr Glu Asn Asp Val Gly Gly Gly Thr Glu Val Val
            115                 120                 125

Val Lys
    130

<210> SEQ ID NO 23
<211> LENGTH: 6
<212> TYPE: PRT
<213> ORGANISM: Artificial sequence
<220> FEATURE:
<223> OTHER INFORMATION: synthetic sequence

<400> SEQUENCE: 23

Glu Ser Ile Tyr Ser Tyr
1               5

<210> SEQ ID NO 24
<211> LENGTH: 3
<212> TYPE: PRT
<213> ORGANISM: Artificial sequence
<220> FEATURE:
<223> OTHER INFORMATION: synthetic sequence

<400> SEQUENCE: 24

Lys Ala Ser
1

<210> SEQ ID NO 25
<211> LENGTH: 10
<212> TYPE: PRT
<213> ORGANISM: Artificial sequence
<220> FEATURE:
<223> OTHER INFORMATION: synthetic sequence

<400> SEQUENCE: 25

Gln Asn Tyr Tyr Thr Phe Thr Glu Asn Asp
1               5                   10

<210> SEQ ID NO 26
<211> LENGTH: 138
<212> TYPE: PRT
<213> ORGANISM: Artificial sequence
<220> FEATURE:
<223> OTHER INFORMATION: synthetic sequence

<400> SEQUENCE: 26

Met Glu Thr Gly Pro Arg Trp Leu Leu Leu Val Ala Val Leu Lys Gly
1               5                   10                  15

Val Gln Cys Gln Glu Gln Leu Ala Glu Ser Gly Gly Gly Leu Val Gln
            20                  25                  30

Pro Glu Gly Ser Leu Thr Leu Thr Cys Thr Ala Ser Gly Phe Ser Phe
            35                  40                  45

Trp Arg Tyr Met Cys Trp Val Arg Gln Ala Pro Gly Lys Gly Leu Glu
    50                  55                  60

Trp Val Ala Cys Ile Asp Gly Gly Asn Thr Asn Arg Leu Tyr Tyr Ala
65                  70                  75                  80

Ser Trp Ala Lys Gly Arg Phe Thr Ile Ser Lys Thr Ser Ser Thr Thr
                85                  90                  95

Val Thr Leu His Met Thr Ser Leu Thr Val Ala Asp Thr Ala Thr Tyr
            100                 105                 110

Phe Ser Ala Arg Val Arg Leu Gly Asn Asn Asp Tyr Ile Asp Leu Trp
        115                 120                 125

Gly Gln Gly Thr Leu Val Thr Val Ser Ser
    130                 135

<210> SEQ ID NO 27
<211> LENGTH: 6
<212> TYPE: PRT
<213> ORGANISM: Artificial sequence
<220> FEATURE:
<223> OTHER INFORMATION: synthetic sequence

<400> SEQUENCE: 27

Gly Phe Ser Phe Trp Arg
1               5

<210> SEQ ID NO 28
<211> LENGTH: 9
<212> TYPE: PRT
<213> ORGANISM: Artificial sequence
<220> FEATURE:
<223> OTHER INFORMATION: synthetic sequence

<400> SEQUENCE: 28

Cys Ile Asp Gly Gly Asn Thr Asn Arg
1               5

<210> SEQ ID NO 29
<211> LENGTH: 13
<212> TYPE: PRT
<213> ORGANISM: Artificial sequence
<220> FEATURE:
<223> OTHER INFORMATION: synthetic sequence

<400> SEQUENCE: 29

Ala Arg Val Arg Leu Gly Asn Asn Asp Tyr Ile Asp Leu
1               5                   10

<210> SEQ ID NO 30
<211> LENGTH: 131
<212> TYPE: PRT
<213> ORGANISM: Artificial sequence
<220> FEATURE:
<223> OTHER INFORMATION: synthetic sequence

<400> SEQUENCE: 30

Met Asp Thr Arg Ala Pro Thr Gln Leu Leu Gly Leu Leu Leu Leu Trp
1               5                   10                  15

Leu Pro Gly Ala Arg Cys Asp Val Val Leu Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Ile Ser Asn Tyr Leu Ala Trp Tyr Gln Gln Lys Pro Gly Gln
    50                  55                  60

Pro Pro Lys Leu Leu Ile Tyr Arg Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Asn Trp Asp Leu Asp Gly Ala Phe Gly Gly Thr Glu Val
        115                 120                 125

Val Val Lys
    130

<210> SEQ ID NO 31
<211> LENGTH: 11
<212> TYPE: PRT
<213> ORGANISM: Artificial sequence
<220> FEATURE:
<223> OTHER INFORMATION: synthetic sequence

<400> SEQUENCE: 31

Gln Gln Gly Tyr Asn Trp Asp Leu Asp Gly Ala
1               5                   10

<210> SEQ ID NO 32
<211> LENGTH: 417
<212> TYPE: DNA
<213> ORGANISM: Artificial sequence
<220> FEATURE:
<223> OTHER INFORMATION: synthetic sequence

<400> SEQUENCE: 32

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | caccctgac | actcacctgc | 120 |
| acagtctctg | gattctccct | cagtagctat | acaatgggct | gggtccgcca | ggctccaggg | 180 |
| aaggggctgg | agtggatcgg | agacattaag | actggtgata | ggacatacta | cgcgaactgg | 240 |
| gcaaaaggcc | gattcaccat | ctccagaacc | tcgaccacgg | tggatctgaa | aatgaccagt | 300 |
| ctgacaaccg | aggacacggc | cacctatttc | tgtgcccgag | tgtatgttag | tggtaatgat | 360 |
| cactatgact | tgtggggcca | gggcaccctg | gtcaccgtct | cgagcggaca | gccgaaa | 417 |

<210> SEQ ID NO 33
<211> LENGTH: 408
<212> TYPE: DNA
<213> ORGANISM: Artificial sequence
<220> FEATURE:
<223> OTHER INFORMATION: synthetic sequence

<400> SEQUENCE: 33

| | | | | | |
|---|---|---|---|---|---|
| atggacacga | gggcccccac | tcagctgctg | gggctcctgc | tgctctggct | cccaggtgcc | 60 |
| agatgtgcct | atgatatgac | ccagactcca | gcctctgtgg | aggtagctgt | gggaggcaca | 120 |
| gtcaccatca | gtgccaggc | cagtcagagt | attagtaact | acttagcctg | gtatcagcag | 180 |
| aaaccagggc | agcctcccaa | gctcctgatc | tacagggcat | ccactctggc | atctggggtc | 240 |
| ccatcgcggt | tcaaaggcag | tggacgtggg | acagagttca | ctctcaccat | cagcggcgtg | 300 |
| gagtgtgccg | atgctgccac | ttactactgt | caactgggtt | atacttatag | taatgttgag | 360 |
| aatgctttcg | gcggagggac | cgaggtggtg | gtcaaaggtg | atcccgtg | | 408 |

<210> SEQ ID NO 34
<211> LENGTH: 417
<212> TYPE: DNA
<213> ORGANISM: Artificial sequence
<220> FEATURE:
<223> OTHER INFORMATION: synthetic sequence

<400> SEQUENCE: 34

```
atggagaccg gctgcgctg gcttctcctg gtcgctgtgc tcaaaggtgt ccagtgtcag      60
tcggtggagg agtccggggg tcgcctggtc acgcctggga cacccctgac actcacctgc    120
acagtctctg gattctccct cagtagctat acaatgggct gggtccgcca ggctccaggg    180
aaggggctgg agtggatcgg agacattaag actggtgata ggacatacta cgcgaactgg    240
gcaaaaggcc gattcaccat ctccagaacc tcgaccacgg tggatctgaa aatgaccagt    300
ctgacaaccg aggacacggc cacctatttc tgtgcccgag tgtatgttag tggtaatgat    360
cactatgact tgtggggcca gggcaccctg gtcaccgtct cgagcggaca gccgaaa       417
```

<210> SEQ ID NO 35
<211> LENGTH: 408
<212> TYPE: DNA
<213> ORGANISM: Artificial sequence
<220> FEATURE:
<223> OTHER INFORMATION: synthetic sequence

<400> SEQUENCE: 35

```
atggacacga gggcccccac tcagctgctg gggctcctgc tgctctggct cccaggtgcc     60
agatgtgcct atgatatgac ccagactcca gcctctgtgg aggtagctgt gggaggcaca    120
gtcaccatca agtgccaggc cagtcagagc attagtaact acttagcctg gtatcagcag    180
aaaccagggc agcctcccaa gctcctgatc tacagggcat ccaatctggc atctggggtc    240
tcatcgcggt tcaaaggcag tggacgtggg acagagttca ctctcaccat cagcggcgtg    300
gagtgtgccg atgctgccac ttactactgt caactgggtt atacttatac taatgttgag    360
aatgctttcg gcggagggac cgaggtggtg gtcaaaggtg atcccgtg              408
```

<210> SEQ ID NO 36
<211> LENGTH: 417
<212> TYPE: DNA
<213> ORGANISM: Artificial sequence
<220> FEATURE:
<223> OTHER INFORMATION: synthetic sequence

<400> SEQUENCE: 36

```
atggagactg gctgcgctg gcttctcctg gtcgctgtgc tcaaaggtgt ccagtgtcag      60
gagcagctgg tggagtccgg gggaggcctg gtccagtctg agggatccct gacactcacc    120
tgcacagctt ctggattctc cttcagcagc accaagtaca tgtgctgggt ccgccaggct    180
ccagggaaga ggcctgagtg gatcgcatgc attggtactg ataccactta ctacgcgagc    240
tgggcgaaag gccgattcac catctccaga acctcgtcga ccacggtgac tctgcaaatg    300
accagtctga cagccgcgga cacggccacc tatttctgtg cgagaagtag tagtactggt    360
tattataatt tgtggggcca gggcaccctg gtcaccgtct cgagcggaca gccgaaa       417
```

<210> SEQ ID NO 37
<211> LENGTH: 405
<212> TYPE: DNA
<213> ORGANISM: Artificial sequence
<220> FEATURE:
<223> OTHER INFORMATION: synthetic sequence

<400> SEQUENCE: 37

```
atggacacga gggcccccac tcagctgctg gggctcctgc tgctctggct cccaggtgcc     60
agatgtgccg acgtcgtgat gacccagact ccagcctccg tgtctgaacc tgtgggaggc    120
acagtcacca tcaagtgcca ggccagtcag agcattcgta gctacttagc ctggtatcag    180
```

| | |
|---|---|
| cagaaaccag ggcagcctcc caagctcctg atctattatg catccactct ggcatctggg | 240 |
| gtctcatcgc ggttcaaagg cagtggatct gggacagagt tcactctcac catcaacggc | 300 |
| gtgcagtgtg acgatgctgc cacttactac tgtcacgact attatacttt tactgataat | 360 |
| gatttcggcg agggaccga ggtggtggtc aaaggtgatc ccgtg | 405 |

<210> SEQ ID NO 38
<211> LENGTH: 426
<212> TYPE: DNA
<213> ORGANISM: Artificial sequence
<220> FEATURE:
<223> OTHER INFORMATION: synthetic sequence

<400> SEQUENCE: 38

| | |
|---|---|
| atggagactg ggctgcgctg gcttctcctg gtcgctgtgc tcaaaggtgt ccagtgtcag | 60 |
| gagcagctgg tggagtccgg gggaggcctg gtccagcctg agggatccct gacactcacc | 120 |
| tgcacagctt ctggattctc cttcagcagc accaagtaca tgtgctgggt ccgccaggct | 180 |
| ccagggaggg ggcctgagtg ggtcgcatgt attggtgttg gtagtcgtgg tagcacttac | 240 |
| tacgcgagcc gggcgaaagg ccgattcacc atctccaaaa cctcgtcgac acggtgact | 300 |
| ctgcaaatga ccagtctgac agccgcggac acggccacct atttctgtgc gaggagtagt | 360 |
| actactggtt attatatttt atggggccag ggcaccctgg tcaccgtctc gagcggacag | 420 |
| ccgaaa | 426 |

<210> SEQ ID NO 39
<211> LENGTH: 402
<212> TYPE: DNA
<213> ORGANISM: Artificial sequence
<220> FEATURE:
<223> OTHER INFORMATION: synthetic sequence

<400> SEQUENCE: 39

| | |
|---|---|
| atggacacga gggcccccac tcagctgctg gggctcctgc tgctctggct cccaggtgcc | 60 |
| aggtgtgcat tcgagatgac ccagactcca tcctccgtgt ctgcagctgt gggaggcaca | 120 |
| gtcaccatca gtgccaggc cagtgagagc atttacagct acttagcctg gtatcagcag | 180 |
| aaaccagggc agcctcccaa gctcctgatc tacaaggcat ccactctggc atctggggtc | 240 |
| tcatcgcggt tcaaaggaag tggatctggg acagagttca ctctcaccat cagcggcgtg | 300 |
| cagtgtgacg atgctgccac ttactactgt caaaactatt atacttttac tgagaatgat | 360 |
| gtcggcggag ggaccgaggt ggtggtcaaa ggtgatcccg tg | 402 |

<210> SEQ ID NO 40
<211> LENGTH: 426
<212> TYPE: DNA
<213> ORGANISM: Artificial sequence
<220> FEATURE:
<223> OTHER INFORMATION: synthetic sequence

<400> SEQUENCE: 40

| | |
|---|---|
| atggagactg ggccgcgctg gcttctcctg gtcgctgtgc tcaaaggtgt ccagtgtcag | 60 |
| gagcagctgg cggagtccgg gggaggcctg gtccagcctg agggatccct gacactcacc | 120 |
| tgcacagcct ctggattctc cttctggcgc tacatgtgct gggtccgcca ggctccaggg | 180 |
| aagggctgg agtgggtcgc atgtattgat ggtggcaata ctaataggct ctattacgcg | 240 |
| agctgggcga aaggccgatt caccatctcc aaaacctcgt cgaccacggt gactctgcac | 300 |
| atgaccagtc tgacagtcgc ggacacggcc acctatttca gtgcgagagt tcggcttggt | 360 |

```
aataatgatt atatagactt gtggggccag ggcaccctgg tcaccgtctc gagcggacag    420
ccgaaa                                                               426

<210> SEQ ID NO 41
<211> LENGTH: 405
<212> TYPE: DNA
<213> ORGANISM: Artificial sequence
<220> FEATURE:
<223> OTHER INFORMATION: synthetic sequence

<400> SEQUENCE: 41
atggacacga gggcccccac tcagctgctg gggctcctgc tgctctggct cccaggtgcc     60
agatgtgatg ttgtgctgac ccagactcca gcctccgtgg aggcagctgt gggaggcaca   120
gtcaccatca agtgccaggc cagtcagagc attagtaact acttagcctg gtatcagcag   180
aaaccagggc agcctcccaa gctcctgatc tacagggcat ccactctggc atctggggtc   240
ccatcgcggt tcaaaggcag tggatctggg acacagttca ctctcaccat cagcgacctg   300
gagtgtgccg atgctgccac ttactactgt caacagggtt ataattggga tcttgatggt   360
gctttcggcg gagggaccga ggtggtggtc aaaggtgatc ccgtg                   405
```